United States Patent
Serizawa et al.

(10) Patent No.: US 10,659,756 B2
(45) Date of Patent: *May 19, 2020

(54) IMAGE PROCESSING APPARATUS, CAMERA APPARATUS, AND IMAGE PROCESSING METHOD

(71) Applicant: PANASONIC I-PRO SENSING SOLUTIONS CO., LTD., Fukuoka (JP)

(72) Inventors: Masayuki Serizawa, Fukuoka (JP); Yuji Kiniwa, Fukuoka (JP); Akira Yamaguchi, Fukuoka (JP); Haruo Kogane, Fukuoka (JP); Tetsushi Hirano, Fukuoka (JP)

(73) Assignee: PANASONIC I-PRO SENSING SOLUTIONS CO., LTD., Fukuoka (JP)

(*) Notice: Subject to any disclaimer, the term of this patent is extended or adjusted under 35 U.S.C. 154(b) by 23 days.

This patent is subject to a terminal disclaimer.

(21) Appl. No.: 16/038,345

(22) Filed: Jul. 18, 2018

(65) Prior Publication Data

US 2019/0037201 A1 Jan. 31, 2019

(30) Foreign Application Priority Data

Jul. 31, 2017 (JP) .................... 2017-148678

(51) Int. Cl.
  *H04N 13/128* (2018.01)
  *A61B 34/20* (2016.01)
  (Continued)

(52) U.S. Cl.
  CPC ....... *H04N 13/128* (2018.05); *A61B 1/00009* (2013.01); *A61B 1/00193* (2013.01);
  (Continued)

(58) Field of Classification Search
  CPC .... H04N 13/128; H04N 13/189; H04N 13/15; H04N 13/194; H04N 13/122; H04N 13/289; A61B 34/20; A61B 1/00193
  (Continued)

(56) References Cited

U.S. PATENT DOCUMENTS

2014/0210975 A1* 7/2014 Hirakawa .......... G02B 23/2423
  348/68
2014/0350338 A1* 11/2014 Tanaka ............... A61B 1/00009
  600/111

(Continued)

FOREIGN PATENT DOCUMENTS

JP 2011-206425 A 10/2011

OTHER PUBLICATIONS

U.S. Appl. No. 16/038,358 to Kenji Kobayashi et al., filed Jul. 18, 2018.

(Continued)

*Primary Examiner* — Patricia I Young
(74) *Attorney, Agent, or Firm* — Greenblum & Bernstein, P.L.C.

(57) ABSTRACT

There is provided an image processing apparatus which is connected to a camera head capable of imaging a left eye image and a right eye image having parallax on one screen based on light at a target site incident on an optical instrument, the apparatus including: an image processor that performs the signal processing of the left eye image and the right eye image which are imaged by the camera head; and an output controller that outputs the left eye image and the right eye image on which the signal processing is performed to a monitor, in which the image processor adjusts an extraction position of at least one of the left eye image and (Continued)

the right eye image in accordance with a user operation based on the left eye image and the right eye image which are displayed on the monitor.

8 Claims, 31 Drawing Sheets

(51) Int. Cl.
| | |
|---|---|
| *A61B 90/00* | (2016.01) |
| *H04N 13/189* | (2018.01) |
| *H04N 13/15* | (2018.01) |
| *H04N 13/194* | (2018.01) |
| *H04N 13/239* | (2018.01) |
| *H04N 13/122* | (2018.01) |
| *H04N 13/289* | (2018.01) |
| *A61B 1/00* | (2006.01) |
| *G02B 21/12* | (2006.01) |
| *H04N 5/235* | (2006.01) |
| *G02B 21/00* | (2006.01) |
| *H04N 13/106* | (2018.01) |
| *H04N 13/00* | (2018.01) |
| *H04N 5/225* | (2006.01) |

(52) U.S. Cl.
CPC .............. *A61B 34/20* (2016.02); *A61B 90/37* (2016.02); *G02B 21/0012* (2013.01); *H04N 5/2353* (2013.01); *H04N 13/122* (2018.05); *H04N 13/15* (2018.05); *H04N 13/158* (2018.05); *H04N 13/189* (2018.05); *H04N 13/194* (2018.05); *H04N 13/239* (2018.05); *H04N 13/289* (2018.05); *A61B 2034/2057* (2016.02); *A61B 2090/371* (2016.02); *H04N 2005/2255* (2013.01); *H04N 2013/0081* (2013.01)

(58) Field of Classification Search
USPC ......................................................... 348/48
See application file for complete search history.

(56) References Cited

U.S. PATENT DOCUMENTS

| | | | |
|---|---|---|---|
| 2017/0046842 A1* | 2/2017 | Yamaguchi | ........ A61B 1/00009 |
| 2017/0168309 A1 | 6/2017 | Kasazumi et al. | |
| 2017/0251196 A1 | 8/2017 | Kiniwa et al. | |

OTHER PUBLICATIONS

U.S. Appl. No. 16/039,424 to Kenji Kobayashi et al., filed Jul. 19, 2018.

* cited by examiner

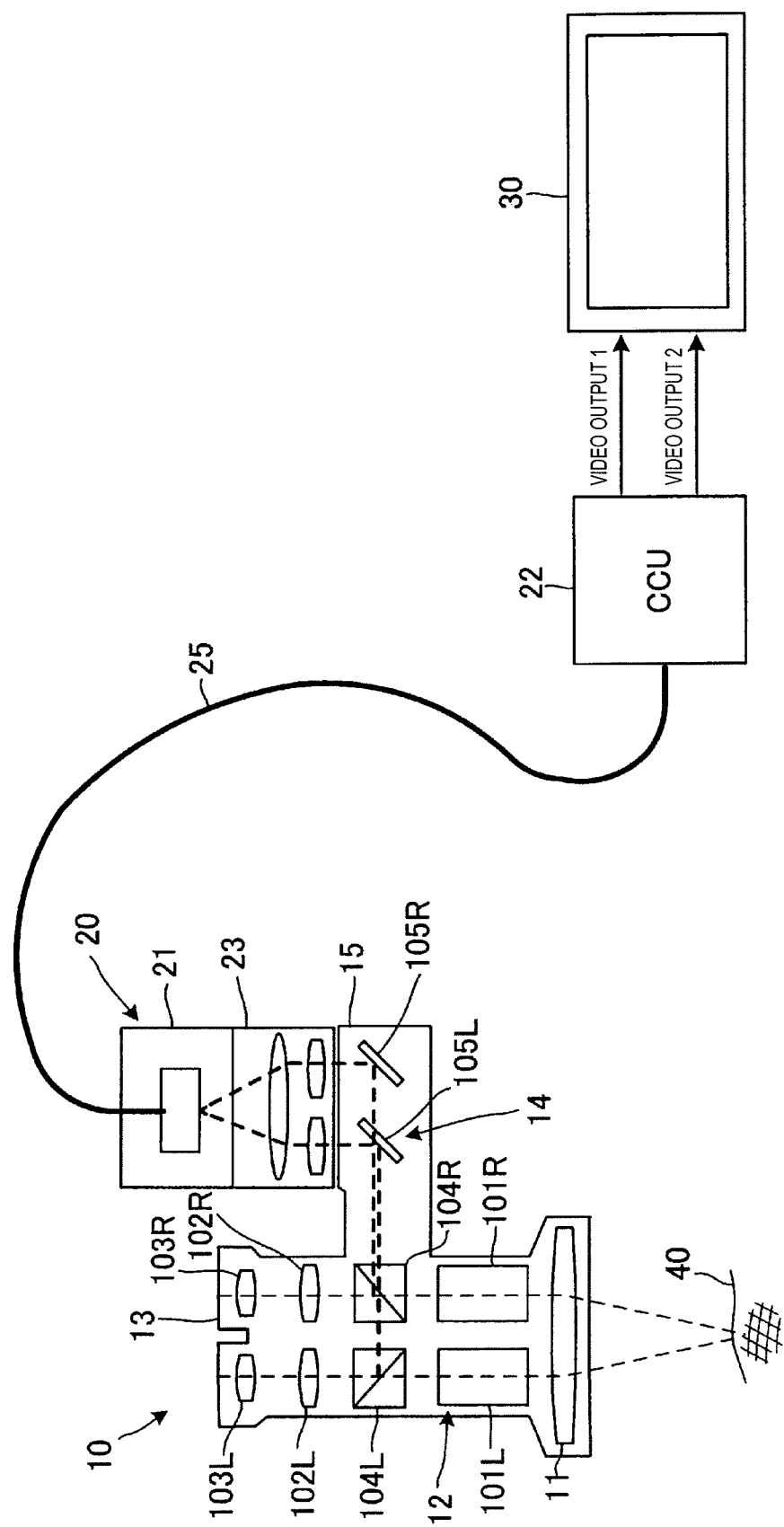

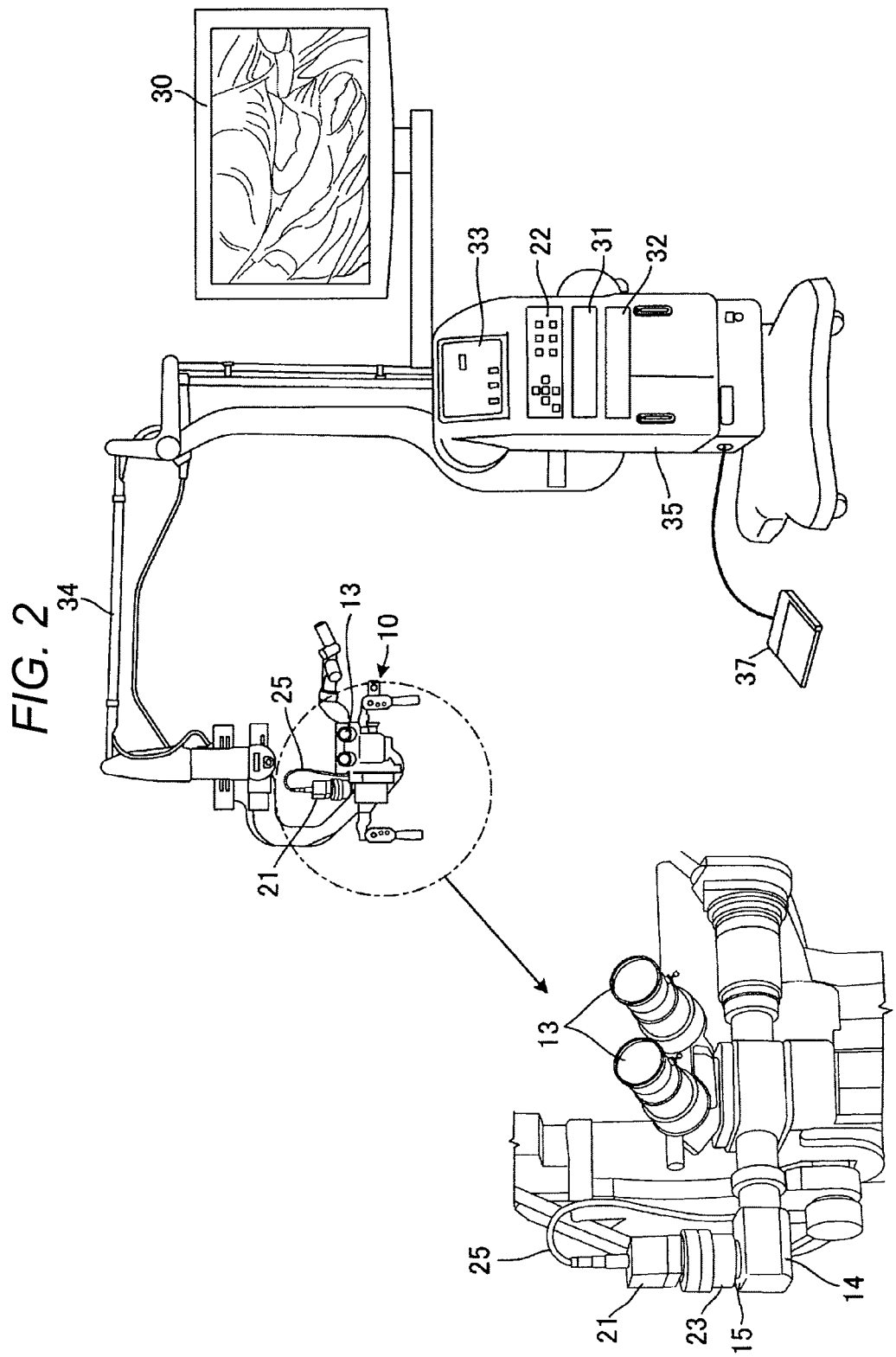

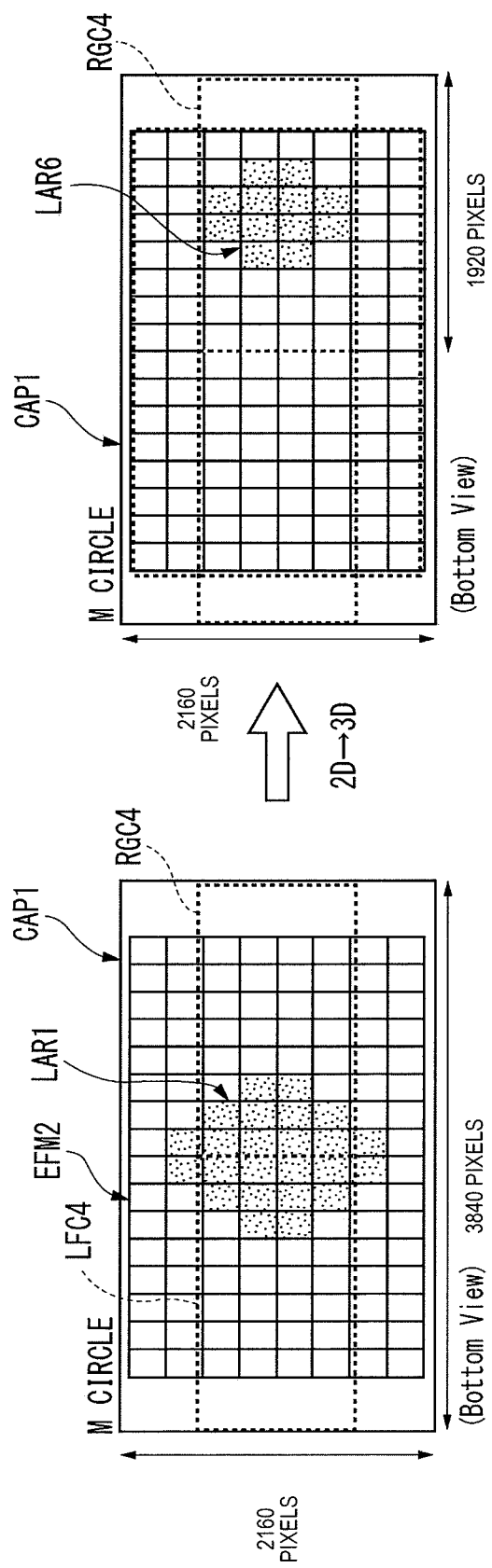

IMAGE PROCESSING APPARATUS, CAMERA APPARATUS, AND IMAGE PROCESSING METHOD

BACKGROUND

1. Technical Field

The present disclosure relates to an image processing apparatus, a camera apparatus, and an image processing method for processing a captured image obtained during a medical practice, for example.

2. Description of the Related Art

For example, in microscopic surgery in which a microscope for surgery is used while observing a fine surgical target site (such as an affected part of a human body) or an endoscopic surgical operation in which an endoscope is used while observing a surgical target site in the body, an observation image including the surgical target site is imaged and displayed on a monitor. By displaying the observation image on the monitor, it is possible to easily and finely recognize the surgical target site, and it is possible for a plurality of persons involved in surgery to observe the details of the site, and it is possible to grasp the situation in real time while observing an image of the surgical site.

As a related art of the kind of camera apparatus, for example, a stereoscopic endoscope apparatus of Japanese Patent Unexamined Publication No. 2011-206425 (PTL 1) is known. In the stereoscopic endoscope apparatus, an endoscope acquires a wide-angle side captured image (2D image), a stereoscopic viewing image (3D image) and a navigation image (whole image), a 3D image is displayed at a part of a 2D image, and the display region of the 3D image is controlled. Accordingly, it is possible to alleviate fatigue or tension of the reference person of the image.

In the above-described medical camera system, in order to ensure a clear field of view of a target site at which surgery or treatment is performed, a display video with high definition and excellent visibility is desired. In addition, since the size or state of an observation target can be grasped more accurately and easily by stereoscopic viewing of a target site, there is an increasing demand for a 3D video that provides a stereoscopic observed video to the observer. Particularly, in a surgical application of a fine site, a high-definition 3D video is required, but in the related art, such as PTL 1, there was a problem that it is difficult to visually recognize the details of the observed video clearly. In addition, in order to generate a high-definition 3D video required in the medical field, it is necessary to use two different cameras for imaging an image for a left eye (hereinafter referred to as "left eye image") and an image for a right eye (hereinafter referred to as "right eye image") which have parallax.

In addition, in order to display a highly accurate 3D video on a monitor, it is necessary to generate the left eye image and the right eye image which form the 3D image with high accuracy. However, it is not always easy to generate a highly accurate left eye image and right eye image due to the design of the actual imaging optical system. For example, due to the positioning (for example, whether lenses are disposed in parallel or the like) of each of a left eye lens for imaging the left eye image and a right eye lens of the right eye image, or manufacturing variations of the lens itself, there is a case where it is difficult to generate the highly accurate left eye image and the right eye image. It is practically difficult to completely eliminate the causes of such positioning and manufacturing variations. In the related art disclosed in the above-described PTL 1, in a case where the left eye lens and the right eye lens are not appropriately disposed due to positioning or manufacturing variations, the image quality of a part of the left eye image and the right eye image deteriorates and influences the image quality of the 3D video, and it is difficult to grasp the detailed target site (for example, an affected part) for an observer.

SUMMARY

In view of the above-described conventional circumstances, an object of the disclosure is to provide an image processing apparatus, a camera apparatus, and an image processing method which are capable of electronically extracting a part with excellent image quality from each of the left eye image and the right eye image which configure the 3D video by a simple user operation, and imaging and outputting a high-definition 3D video with one camera.

The disclosure provides an image processing apparatus which is connected to a camera head capable of imaging a left eye image and a right eye image having parallax on one screen based on light at a target site incident on an optical instrument, the apparatus including: an image processor that performs the signal processing of the left eye image and the right eye image which are imaged by the camera head; and an output controller that outputs the left eye image and the right eye image on which the signal processing is performed to a monitor, in which the image processor adjusts an extraction position of at least one of the left eye image and the right eye image in accordance with a user operation based on the left eye image and the right eye image which are displayed on the monitor.

In addition, the disclosure provides a camera apparatus including: a camera head that is capable of imaging a left eye image and a right eye image having parallax on one screen based on light at a target site incident on an optical instrument; an image processor that performs the signal processing of the left eye image and the right eye image which are imaged by the camera head; and an output controller that outputs the left eye image and the right eye image on which the signal processing is performed to a monitor, in which the image processor adjusts an extraction position of at least one of the left eye image and the right eye image in accordance with a user operation based on the left eye image and the right eye image which are displayed on the monitor.

In addition, the disclosure provides an image processing method in which an image processing apparatus which is connected to a camera head capable of imaging a left eye image and a right eye image having parallax on one screen based on light at a target site incident on an optical instrument is used, the method including: performing signal processing of the left eye image and the right eye image which are imaged by the camera head; outputting the left eye image and the right eye image on which the signal processing is performed to a monitor; and adjusting an extraction position of at least one of the left eye image and the right eye image in accordance with a user operation based on the left eye image and the right eye image which are displayed on the monitor.

According to the present disclosure, it is possible to electronically extract a part with excellent image quality from each of the left eye image and the right eye image which configure the 3D video by a simple user operation, and image and output a high-definition 3D video with one camera.

BRIEF DESCRIPTION OF THE DRAWINGS

FIG. 1 is a system configuration view illustrating a configuration example in which a medical camera system including a camera apparatus of each embodiment is applied to a surgical microscope system;

FIG. 2 is a view illustrating an external appearance example of the surgical microscope system of each of the embodiments;

FIG. 11C is an explanatory view illustrating an adjustment example of a photometric area of automatic exposure with respect to a third subject in accordance with switching from the 2D mode to the 3D mode;

Figure 3A:
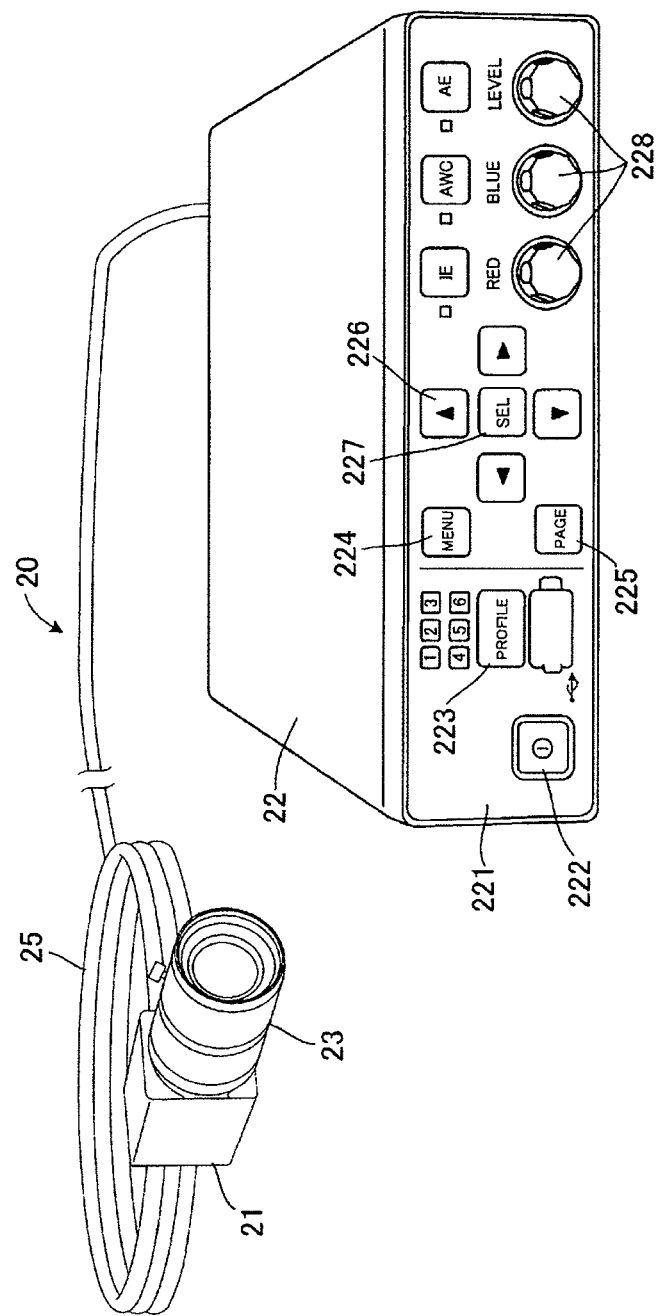
FIG. 3A is a view illustrating an external appearance example of a front side of a camera head and a CCU of the camera apparatus of each of the embodiments.

DETAILED DESCRIPTION (Background of Contents of Embodiment 1)

In the above-described medical camera system, in order to ensure a clear field of view of a target site at which surgery or treatment is performed, a display video with high definition and excellent visibility is desired. In addition, since the size or state of an observation target can be grasped more accurately and easily by stereoscopic viewing of a target site, there is an increasing demand for a 3D video that provides a stereoscopic observed video to the observer. Particularly, in a surgical application of a fine site, a high-definition 3D video is required, but in the related art, such as PTL 1, there was a problem that it is difficult to visually recognize the details of the observed video clearly. In addition, in order to generate a high-definition 3D video required in the medical field, it is necessary to use two different cameras for imaging an image for a left eye (left eye image) and an image for a right eye (right eye image) which have parallax.

In addition, in order to display a highly accurate 3D video on a monitor, it is necessary to generate the left eye image and the right eye image which configure the 3D video with high accuracy. However, it is not always easy to generate the highly accurate left eye image and right eye image due to the design of an actual imaging optical system. For example, due to the positioning (for example, whether lenses are disposed in parallel or the like) of each of a left eye lens for imaging the left eye image and a right eye lens of the right eye image, or manufacturing variations of the lens itself, there is a case where it is difficult to generate the highly accurate left eye image and the right eye image. It is practically difficult to completely eliminate the causes of such positioning and manufacturing variations. In the related art disclosed in the above-described PTL 1, in a case where the left eye lens and the right eye lens are not appropriately disposed due to positioning or manufacturing variations, the image quality of a part of the left eye image and the right eye image deteriorates and influences the image quality of the 3D video, and it is difficult to grasp the detailed target site (for example, an affected part) for an observer.

Here, in the following Embodiment 1, in consideration of the above-described situation of the related art, an example of an image processing apparatus, a camera apparatus, and an image processing method which can electronically extract a part with excellent image quality from each of the left eye image and the right eye image which configure the 3D video by a simple user operation, and images and outputs a high-definition 3D video with one camera, will be described.

Embodiment 1

Hereinafter, each of the embodiments specifically disclosing the image processing apparatus, the camera apparatus, and the image processing method according to the disclosure will be appropriately described in detail with reference to the drawings. However, there is a case where description detailed more than necessary is omitted. For example, there is a case where detailed descriptions of already well-known matters and redundant descriptions on substantially the same configuration is omitted. This is to avoid the unnecessary redundancy of the following description and to make it easy to understand the disclosure for those skilled in the art. In addition, the attached drawings and the following description are provided to enable those skilled in the art to fully understand the disclosure, and are not intended to limit the subject matter described in the claims.

In addition, in each of the following embodiments, a configuration example of a medical camera system including the image processing apparatus or the camera apparatus according to each of the embodiments will be described. As a specific application example of each of the embodiments, the configuration of the camera apparatus in the surgical microscope system will be exemplified. However, the embodiments of the camera apparatus according to the disclosure are not limited to the contents of each of the embodiments which will described later.

The camera apparatus according to each of the embodiments is configured to be capable of imaging and outputting, for example, an observed video (hereinafter, referred to as "2D video") capable of planar viewing of 4K resolution (that is, for example, "2160 pixels×3840 pixels" that corresponds to 4K pixels, for example) and an observed video (hereinafter, referred to as "3D video") capable of stereoscopic viewing of full high definition (FHD) resolution (that is, for example, "1080 pixels×1920 pixels" that corresponds to 2K pixels), as a high-definition observed video. In addition, the resolution equivalent to full high vision (FHD) is referred to as "2K pixels".

FIG. 1 is a system configuration view illustrating a configuration example in which a medical camera system including a camera apparatus of each of the embodiments is applied to a surgical microscope system. The surgical microscope system includes surgical microscope 10 (an example of an optical instrument), camera apparatus 20, and monitor 30. Camera apparatus 20 includes: camera head 21 for imaging an observed image of a target site obtained by surgical microscope 10; and camera control unit (CCU) 22 for performing signal processing of the observed video imaged by controlling camera head 21. In camera apparatus 20, camera head 21 and CCU 22 are connected to each other by signal cable 25. Camera head 21 is installed in camera installer 15 of surgical microscope 10 and connected thereto. Monitor 30 for displaying the observed video is connected to an output terminal of CCU 22.

Surgical microscope 10 is a binocular microscope and includes objective lens 11, observation optical system 12 provided so as to correspond to the left and right eyes of the observer, eyepiece portion 13, optical system 14 for camera imaging, and camera installer 15. Observation optical system 12 includes zoom optical systems 101R and 101L, image forming lenses 102R and 102L, and eyepiece lenses 103R and 103L so as to correspond to the left and right eyes of the observer. Zoom optical systems 101R and 101L, image forming lenses 102R and 102L, and eyepiece lenses 103R and 103L are respectively disposed with an optical axis of objective lens 11 therebetween. Light from the subject (for example, light from the observation target site) becomes incident on the objective lens 11, and then guides the left and right observed images having parallax through zoom optical systems 101R and 101L, imaging lenses 102R and 102L, and eyepiece lenses 103R and 103L, to eyepiece portion 13. The observer can visually recognize subject 40 at the observation target site stereographically by looking at eyepiece portion 13 with both eyes.

Camera imaging optical system 14 includes beam splitters 104R and 104L and mirrors 105R and 105L. Camera imaging optical system 14 deflects and separates the lights of the left and right observed images which passes through observation optical system 12 by beam splitters 104R and 104L, reflects left and right observed images by mirrors 105R and 105L, and guides the left and right observed images having parallax to camera installer 15. By installing and imaging camera head 21 of camera apparatus 20 to camera installer 15, camera apparatus 20 can acquire an observed video capable of stereoscopic viewing for 3D display.

FIG. 2 is a view illustrating an external appearance example of the surgical microscope system of each of the embodiments. Surgical microscope 10 includes eyepiece 13 at the top of the microscope main body, a housing of camera imaging optical system 14 extends to the side from a base end portion of eyepiece 13, camera installer 15 is provided. Camera installer 15 opens upward and is formed such that imaging lens portion 23 of camera head 21 can be installed thereto. Imaging lens portion 23 is attachable to and detachable from the main body of camera head 21 and can be exchanged, and is configured so that an imaging optical system having different optical characteristics can be used depending on the application. Camera head 21 is configured with a three-plate type capture having, for example, a spectral prism that separates a subject image into each color of red green blue (RGB) and three image sensors that respectively image subject images of each color of RGB. In addition, a single plate type capture having one image sensor may be used.

The surgical microscope system includes light source device 31 for illuminating a target site, recorder 32 for recording the observed video imaged by camera apparatus 20, operation unit 33 for operating the surgical microscope system, and foot switch 37 by which the observer performs an operation input with a foot. Operation unit 33, CCU 22 (one example of the image processing apparatus), light source device 31, and recorder 32 are stored in control unit housing 35. Monitor 30 is disposed in the vicinity of control unit housing 35. Surgical microscope 10 is attached to displaceable support arm 34 and is linked to control unit housing 35 via support arm 34.

Figure 3B:
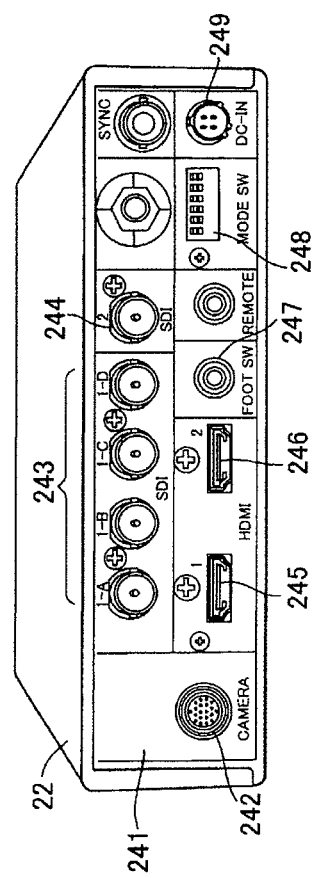
FIG. 3B is a view illustrating an external appearance example of a rear side of the CCU of the camera apparatus of each of the embodiments.

FIGS. 3(A) and 3(B) are views illustrating the external appearance configuration of the camera apparatus of each of the embodiments. FIG. 3A is a view illustrating an external appearance example of a front side of the camera head and the CCU of the camera apparatus of each of the embodiments. FIG. 3B is a view illustrating an external appearance example of a rear side of the CCU of the camera apparatus of each of the embodiments. Camera head 21 is connected to the rear surface of the housing of CCU 22 via signal cable 25. Camera head 21 is configured to be capable of imaging a high-definition observed video, and imaging the left eye image and the right eye image which have parallax on one screen, for example, by a three-plate type or a single-plate type capture, in a case of imaging the 3D video.

On front panel 221, CCU 22 is provided with power switch 222, profile selection switch 223, menu switch 224, page changeover switch 225, upward-and-downward and leftward-and-rightward movement switches 226, selection switch 227, and image quality adjustment switch 228. On rear surface panel 241, CCU 22 has camera terminal 242, serial digital interface (SDI) video output terminals 243 and 244, HDMI (registered trademark) (high-definition multimedia interface) video output terminals 245 and 246, foot switch terminal 247, mode switch 248, and DC power input terminal 249.

CCU 22 (one example of the image processing apparatus) can output the 2D video of 4K pixels or the 3D video of 2K pixels by switching modes. Profile selection switch 223 is a switch for selecting a preset profile in which the mode of CCU 22 is set. A profile is a set value of a parameter related to display of a video displayed on monitors 30 and 130 (refer to the description below), for example, and is provided for each user. The switching setting between a mode in which the 2D video can be output (hereinafter, referred to as "2D mode") and a mode in which the 3D video can be output (hereinafter, referred to as "3D mode") is possible, for example, by selecting the profile by profile selection switch 223, selecting the mode by menu switch 224 and selection switch 227, or setting the mode by mode switch 248 on the rear surface, by the operation of the user, such as an observer.

SDI video output terminals 243 and 244 correspond to the output terminals of two systems of channel CH1 (one example of a first channel) and channel CH2 (one example of a second channel) that correspond to the 3G-SDI standard. SDI video output terminal 243 of channel CH1 has four terminals and can output both 4K video and FHD video. SDI video output terminal 244 of channel CH2 is capable of outputting the FHD video. HDMI (registered trademark) video output terminals 245 and 246 correspond to the output terminals of two systems of channel CH1 (one example of the first channel) and channel CH2 (one example of the second channel). HDMI (registered trademark) video output terminal 245 of the channel CH1 corresponds to the HDMI (registered trademark) 2.0 standard and can output both 4K video and FHD video. HDMI (registered trademark) video output terminal 246 of channel CH2 corresponds to the HDMI (registered trademark) 1.4 standard and can output the FHD video. In addition, the video output terminal may be configured to be capable of outputting both the 4K video and the FHD video at any of the output terminals of the two systems. Further, the form and the number of the video output terminals are not limited to that illustrated in the drawing, and the disclosure is equally applicable even when corresponding to other standards.

Signal cable 25 of camera head 21 is connected to camera terminal 242. Monitor 30 is connected to at least one of SDI video output terminals 243 and 244 and HDMI (registered trademark) video output terminals 245 and 246 via a video signal cable (not illustrated). A power supply device for supplying DC power via a power cable (not illustrated) is connected to DC power input terminal 249. Foot switch 37 is connected to foot switch terminal 247.

Figure 4:
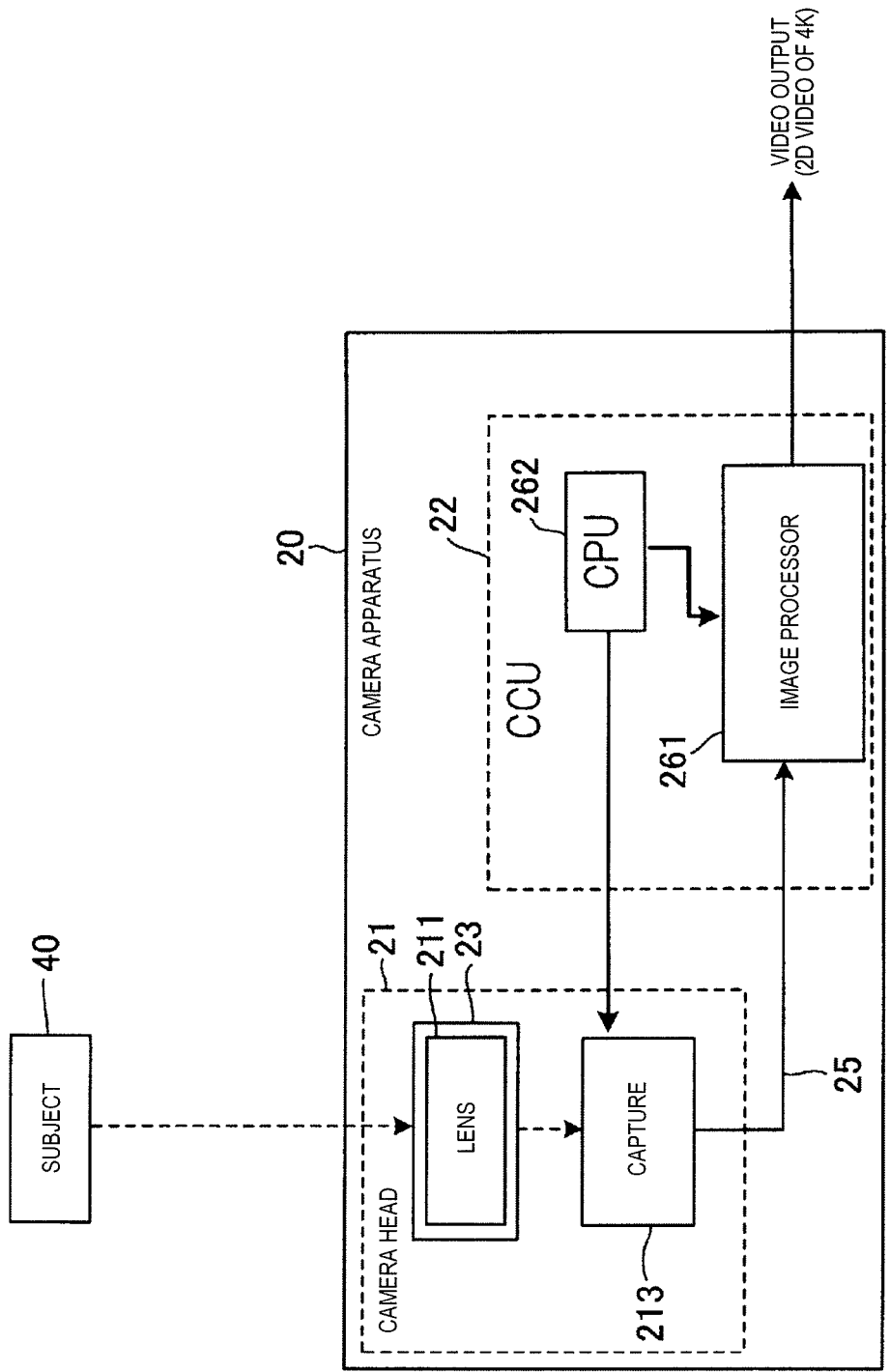
FIG. 4 is a block diagram illustrating a functional configuration example at the time of imaging a 2D video in the camera apparatus of each of the embodiments.

FIG. 4 is a block diagram illustrating a functional configuration example at the time of imaging the 2D video in the camera apparatus of each of the embodiments. In a case of imaging the 2D video of 4K pixels by camera apparatus 20, for example, in a state where monocular lens 211 for forming a subject image is installed in imaging lens portion 23 of camera head 21, camera head 21 is attached to camera installer 15 of surgical microscope 10. The light from subject 40 passes through lens 211 and forms an image on the imaging surface of the three image sensors of three-plate type capture 213, and the RGB subject image is imaged. In other words, camera head 21 includes capture 213 which images the observed image from surgical microscope 10 and obtains the high-definition observed video of high definition (for example, 2K pixels). Capture 213 is capable of acquiring a high-definition captured image and is configured with a three-plate FHD image sensor that images a video of 2K pixels in each color of RGB. The FHD image sensor is configured with an imaging element, such as a charged-coupled device (CCD) or a complementary metal oxide semiconductor (CMOS). In addition, in a case of using a single plate type capture, the capture may be configured with a 4K image sensor capable of imaging a video of 4K pixels and a color filter. The video signal of the imaged video of the subject imaged by camera head 21 is transmitted to CCU 22 via signal cable 25.

CCU 22 (one example of the image processing apparatus) includes: image processor 261 including a signal processing circuit that processes a video signal imaged by camera head 21; and central processing unit (CPU) 262 (one example of the processor) that configures the controller that performs setting mode related to the operations of image processor 261 and capture 213 and control of each operation. Image processor 261 is configured using, for example, a field-programmable gate array (FPGA), and can set and change the circuit configuration and operation by a program. Image processor 261 generates high-definition (here, 4K resolution) 2D video (2D video of 4K) from the 2K video R, G, and B (4K video R, G, and B) of each color of R, G, and B transmitted from camera head 21, and outputs the 2D video to monitor 30 as a video output.

Figure 5:
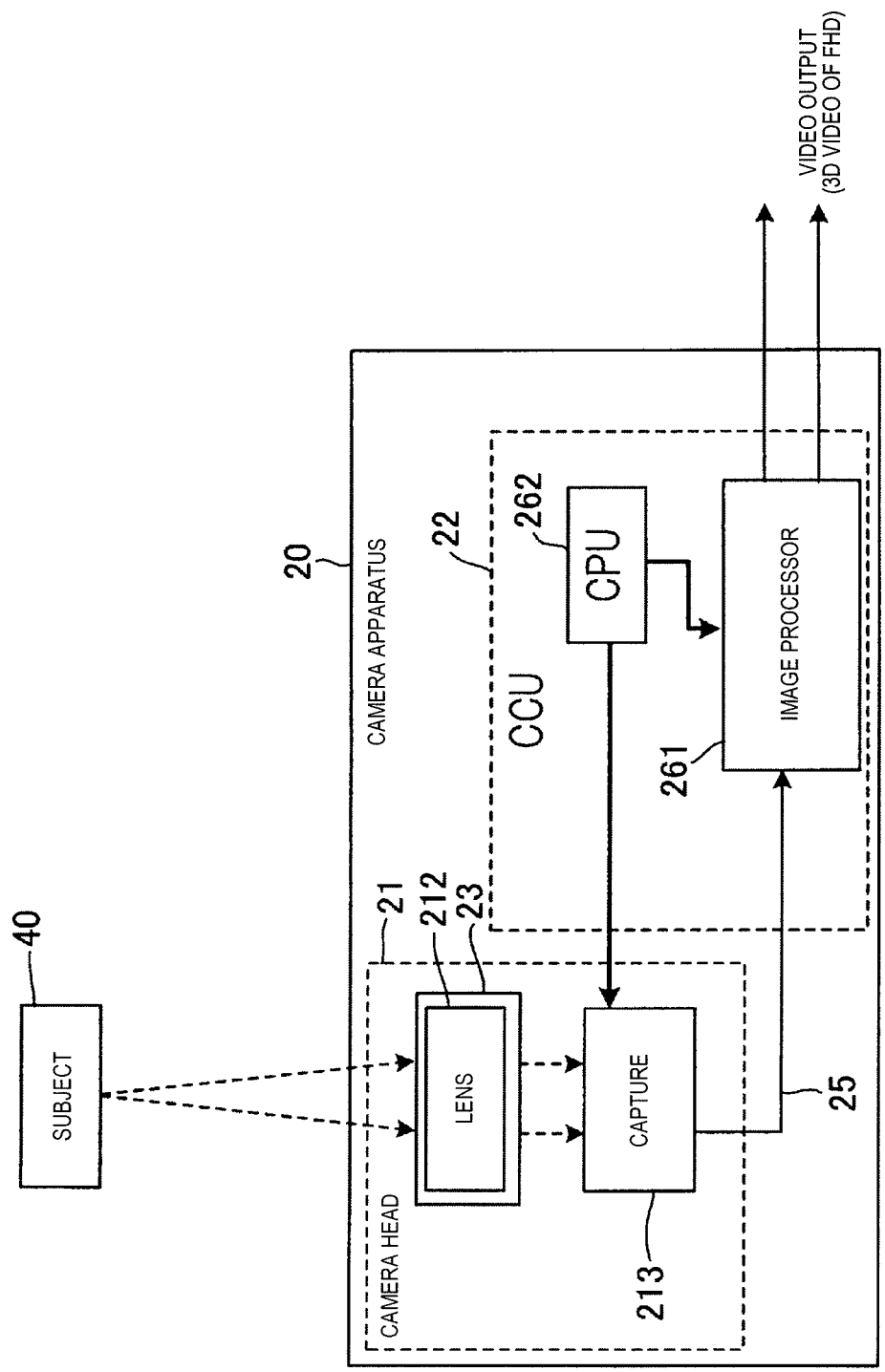
FIG. 5 is a block diagram illustrating a functional configuration example at the time of imaging a 3D video in the camera apparatus of each of the embodiments.

FIG. 5 is a block diagram illustrating a functional configuration example at the time of imaging the 3D video in the camera apparatus of each of the embodiments. In a case of imaging the 3D video of 2 K pixels (that is, 2K left parallax video and 2K right parallax video) by camera apparatus 20, for example, in a state where binocular lens 212 which forms each of left and right subject images having parallax is installed in imaging lens portion 23 of camera head 21, camera head 21 is attached to camera installer 15 of surgical microscope 10. In addition, it is possible to image a video of the subject having left and right parallax using the monocular lens. The light from object 40 passes through lens 212 and forms left and right images adjacent to each other respectively on the imaging surfaces of three image sensors of three-plate type capture 213 as two left and right subjects having parallax, and the subject image of the left and right RGB subject images for 3D video are imaged. In other words, camera head 21 includes capture 213 which images left and right observed images having parallax from surgical microscope 10 and obtains a high definition (for example, 2K pixels) observed video including left and right parallax video on one screen. The video signal for 3D video of the subject imaged by camera head 21 is transmitted to CCU 22 via signal cable 25.

In addition, in a case of imaging a 3D video with camera head 21, instead of exchanging the lens of imaging lens portion 23 for 2D to 3D, an adapter may be provided in camera installer 15 of surgical microscope 10, and the optical system of the adapter may be exchanged for 2D to 3D and used. Otherwise, the optical instrument itself, such as surgical microscope 10 which connects camera head 21 is replaced and used, the 2D video is imaged by installing the optical instrument in the instrument having an observation optical system for 2D, and the 3D video can also be imaged by installing the optical instrument in the instrument having the observation optical system for 3D.

Image processor 261 of CCU 22 generates the high-definition (for example, 2K image) 3D video from left and right 2K video R, G, and B (specifically, the 3D left and 3D right 2K video R, G, and B) for 3D display of each of RGB colors transmitted from camera head 21, and outputs the 3D video as two left and right video outputs 1 and 2 for 3D display to monitor 30. Details of the configuration and operation of image processor 261 for generating 2D video of 4K pixels or 3D video of 2K pixels will be described later. In a case of performing stereoscopic viewing of the observed video, for example, in a state where the observer wears 3D observation glasses, the 3D video is displayed on monitor 30 such that the left parallax video and the right parallax video can be observed with respective eyes.

Figure 6:
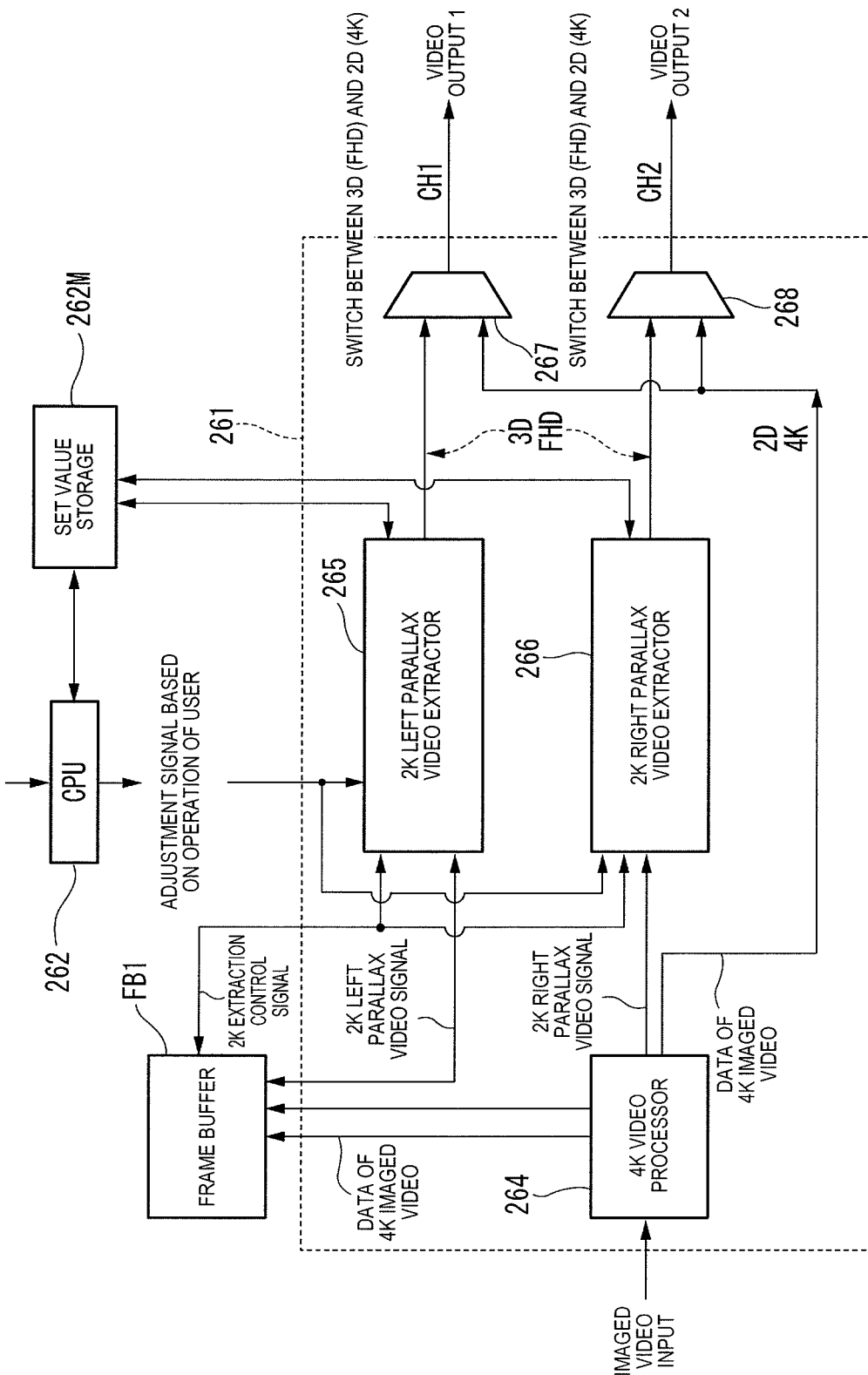
FIG. 6 is a block diagram illustrating a functional configuration example of an image processor of the camera apparatus of Embodiment E

FIG. 6 is a block diagram illustrating a functional configuration example of image processor 261 of camera apparatus 20 of Embodiment 1. The image processor 261 includes 4K video processor 264, 2K left parallax video extractor 265, 2K right parallax video extractor 266, and video output switchers 267 and 268. In addition, when frame buffer FB1 (memory) and set value storage 262M are provided in CCU 22, frame buffer FB1 (memory) and set value storage 262M may be provided either on the inside or on the outside of image processor 261.

4K video processor 264 inputs the 2K video R, G, and B of each color of R, G, and B imaged by three-plate camera head 21 as the resolution enhancement processing of the imaged video, and generates the video of 4K pixels. 4K video processor 264 saves the generated video of 4K pixels in frame buffer FB1 and outputs the video to the video output switchers 267 and 268. In addition, frame buffer FB1 outputs the 2K left parallax video and the 2K right parallax video which are extracted from the saved video of 4K pixels by a control signal extracted from 2K left parallax video extractor 265 and 2K right parallax video extractor 266, to each of video output switchers 267 and 268, respectively. In addition, the extraction of each of the 2K left parallax video and the 2K right parallax video from the saved video of 4K pixels, is performed similar to 2K left parallax video extractor 265 and 2K right parallax video extractor 266. As a method of 4K visualization, for example, a known "pixel shifting" processing is used. For each pixel of the 2K image G, 4K video processor 264 performs processing of shifting pixels of 2K video R and 2K video B by ½ in a horizontal and vertical directions, and generates a color video of 4K pixels. In a case of imaging the 2D video of 4K pixels, 4K video of 2D color is generated from the 2K video R, G, and B for 2D display. In a case of capturing the 3D video of 2K pixels, the 4K video (3D left parallax video and 3D right parallax video) including the left and right parallax videos of 2K pixels from the imaged 2K videos R, G, and B for the left eye and the right eye for 3D display which are left and right adjacent to each other in an image sensor, is generated. In addition, in a case of using a single-plate type capture, the 4K video processor 264 is not provided in image processor 261, and the video signal of the color 4K pixels imaged with camera head 21 is input to image processor 261 and processed.

2K left parallax video extractor 265 (one example of the image processor) performs predetermined signal processing with respect to the left eye image which is imaged by camera head 21. For example, 2K left parallax video extractor 265 extracts a 2K left parallax video that corresponds to a region for half the left eye video from the 4K video including the left and right parallax video of 2K pixels output from 4K video processor 264, and generates an FHD video (3D left parallax video) for the left eye video for 3D display. Further, 2K left parallax video extractor 265 adjusts an extraction range for extracting the 2K left parallax video (that is, a left eye image on the imaging surface) from the 4K video in accordance with an adjustment signal (refer to the description below) based on the operation of the user by moving in any direction of each of the upward-and-downward and leftward-and-downward directions. 2K left parallax video extractor 265 saves the adjustment result in set value storage 262M, and also extracts and outputs 2K left parallax image (left eye image) that corresponds to the adjustment result.

2K right parallax video extractor 266 (one example of the image processor) performs predetermined signal processing with respect to the right eye image which is imaged by camera head 21. For example, 2K right parallax video extractor 266 extracts a 2K right parallax video that corresponds to a region for the remaining half the right eye video from the 4K video including the left and right parallax video of 2K pixels output from 4K video processor 264, and generates an FHD video (3D right parallax video) for the right eye video for 3D display. Further, 2K right parallax video extractor 266 adjusts an extraction range for extracting the 2K right parallax video (that is, a right eye image on the imaging surface) from the 4K video in accordance with an adjustment signal (refer to the description below) based on the operation of the user by moving in any direction of each of the upward-and-downward and leftward-and-downward directions. 2K right parallax video extractor 266 saves the adjustment result of an extraction range in set value storage 262M, and also extracts and outputs 2K right parallax video (right eye image) that corresponds to the adjustment result.

2K left parallax video extractor 265 and 2K right parallax video extractor 266 may respectively move and adjust in a same direction or the extraction ranges of each of the 2K left parallax video (left eye image) and the 2K right parallax video (right eye image) in accordance with an adjustment signal (refer to the description below) based on the operation of the user, and may individually adjust the extraction ranges by moving in different directions.

Video output switcher 267 (one example of the output controller) switches the video signal output and outputs the 2D left parallax video of 2K pixels from the 2K left parallax video extractor 265 or the video signal of the 2D video of 4K pixels from 4K video processor 264 via channel CH1 (one example of the first channel). Video output switcher 268 (one example of the output controller) switches the video signal output and outputs the 2D right parallax video of 2K pixels from the 2K right parallax video extractor 266 or the video signal of the 2D video of 4K pixels from 4K video processor 264 via channel CH2 (one example of the second channel). In a case of outputting the 2D video of 4K pixels, the video signal may be output to both of video output 1 of channel CH1 and video output 2 of channel CH2, or the video signal may be output to only one of video output 1 and video output 2. Further, the 2D video of 4K pixels may be output to either one of channel CH1 and channel CH2, and 2D video of 2K pixels may be output to the other.

Frame buffer FB1 is configured using a semiconductor memory, such as dynamic random access memory (DRAM) or static random access memory (SRAM), and holds video data. For example, frame buffer FB1 saves the data of the 2D video of 4K pixels generated by 4K video processor 264.

Set value storage 262M is configured using a semiconductor memory, such as an electrically erasable programmable read-only memory (EEPROM), and saves the data of the adjustment result of the extraction ranges of the 2K left parallax video and the 2K right parallax video which are adjusted by 2K left parallax video extractor 265 and 2K right parallax video extractor 266. In addition, 2K left parallax video extractor 265 and 2K right parallax video extractor 266 read out the data of the 2D video of 4K pixels saved in frame buffer FB1, and may further adjust the extraction ranges of the 2K left parallax video and the 2K right parallax video by using the adjustment result of the extraction ranges saved in set value storage 262M.

Figure 7:
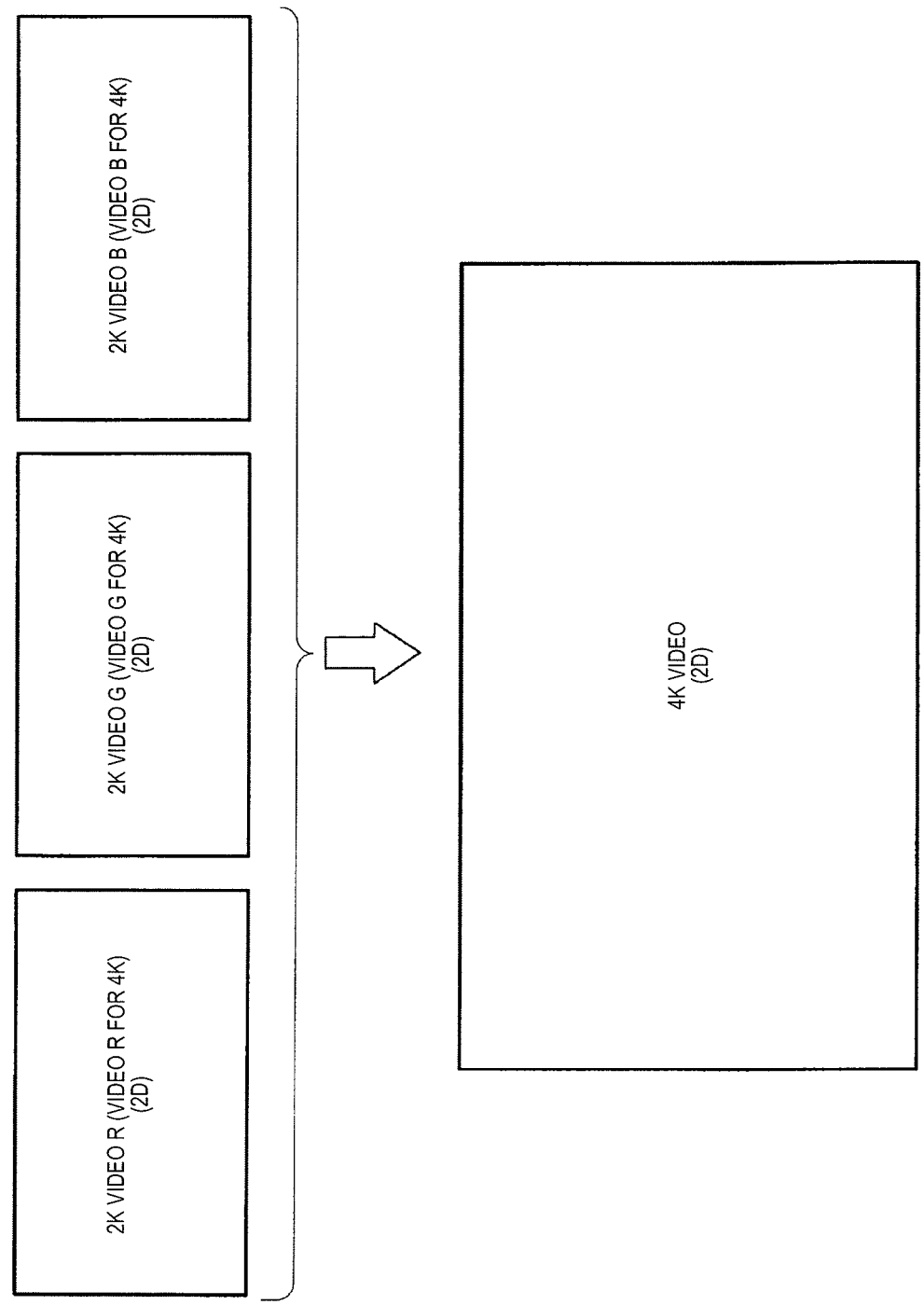
FIG. 7 is an explanatory view illustrating a schematic example of a generation operation of the 2D video in each of the embodiments.

FIG. 7 is an explanatory view showing a schematic example of the generation operation of the 2D video in each of the embodiments, and schematically illustrates processing for generating the 2D video of 4K pixels. In a case of imaging the 2D video of 4K pixels by camera apparatus 20, 2K video R, G, and B of each of the RGB colors are imaged as videos R, G, and B for 4K of 2D by three-plate camera head 21. Next, 4K video processor 264 of image processor 261 performs 4K visualization by performing pixel shifting processing with respect to the video signals of the 2K videos R, G, and B to generate the 2D color 4K video.

Figure 8:
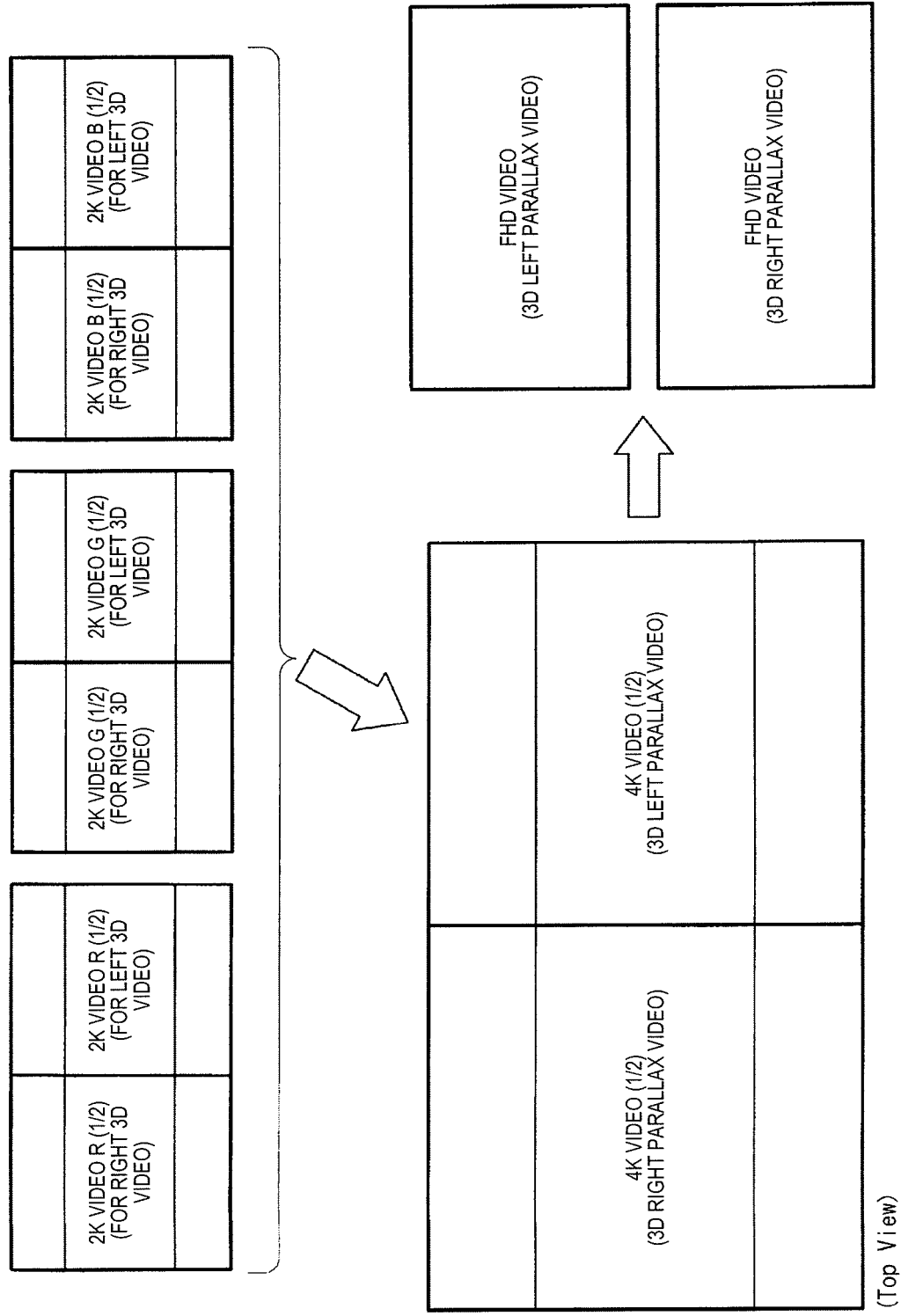
FIG. 8 is an explanatory view illustrating a schematic example of a generation operation of the 3D video in each of the embodiments.

FIG. 8 is an explanatory view illustrating a schematic example of the generation operation of the 3D video in each of the embodiments, and schematically illustrates processing for generating the 3D video of 2K pixels. In a case of imaging the 3D video of 2K pixels by camera apparatus 20, a three-plate type camera head 21 images the 2K videos R, G, and B (for 3D left eye and 3D right eye) of each of RGB colors for the left eye and the right eye for the 3D display in the ½ regions left and right adjacent to each other of the image sensor. Next, 4K video processor 264 of image processor 261 performs 4K visualization by performing the pixel shifting processing with respect to the video signals of the 2K videos R, G, and B including the left and right parallax video to generate the 3D display color 4K video (the 2K left parallax video for 3D and the 2K right parallax video for 3D). Subsequently, 2K left parallax video extractor 265 and 2K right parallax video extractor 266 respectively perform extraction processing of the 2K parallax video and the 2K right parallax video, and generates the FHD video (2K left parallax video for 3D and 2K right parallax video for 3D) for the 3D display.

Here, as described above, in order to display a highly accurate 3D video on monitor 30, it is necessary to generate the 2K left parallax video (left eye image) and the 2K right parallax video (right eye image) which configure the 3D video with high accuracy. However, it is not always easy to generate a highly accurate 2K left parallax video and a 2K right parallax video due to the design of actual observation optical system 12. For example, due to the positioning (for example, parallel disposition) of each of zoom optical system 101R for forming an image of the subject light for obtaining the 2K left parallax video and zoom optical system 101L for forming an image of the subject light for obtaining the 2K right parallax video and manufacturing variations of the lens itself, there is a case where it is difficult to generate highly accurate 2K left parallax video and 2K right parallax video. It is practically difficult to completely eliminate the causes of such positioning and manufacturing variations.

Here, in Embodiment 1, for example, at the time of initial setting of the surgical microscope system, the user (for example, an observer, such as a doctor) reads the 3D video based on the 2K left parallax video and the 2K right parallax video which are displayed (output to a screen) on monitor 30 in a state where the user wears the glasses for 3D observation in the 3D mode (that is, a mode for displaying the 3D video on monitor 30). At this time, image processor 261 of CCU 22 adjusts at least one extraction position of the 2K left parallax video (left eye image) and the 2K right parallax video (right eye image) in accordance with the adjustment signal (one example of the adjustment signal based on the operation of the user) generated by the operation of the user (for example, an operation of movement switch 226 by the user) based on the 3D video displayed (output to the screen) on monitor 30. In addition, the imaging surface (imaging surface at the lower left part of the page of FIG. 8) on which the 4K video of FIG. 8 is imaged, is an imaging surface of a so-called top view (that is, when the imaging surface side is viewed from an object side).

(First Adjustment Example of Extraction Range)

Figure 9A:
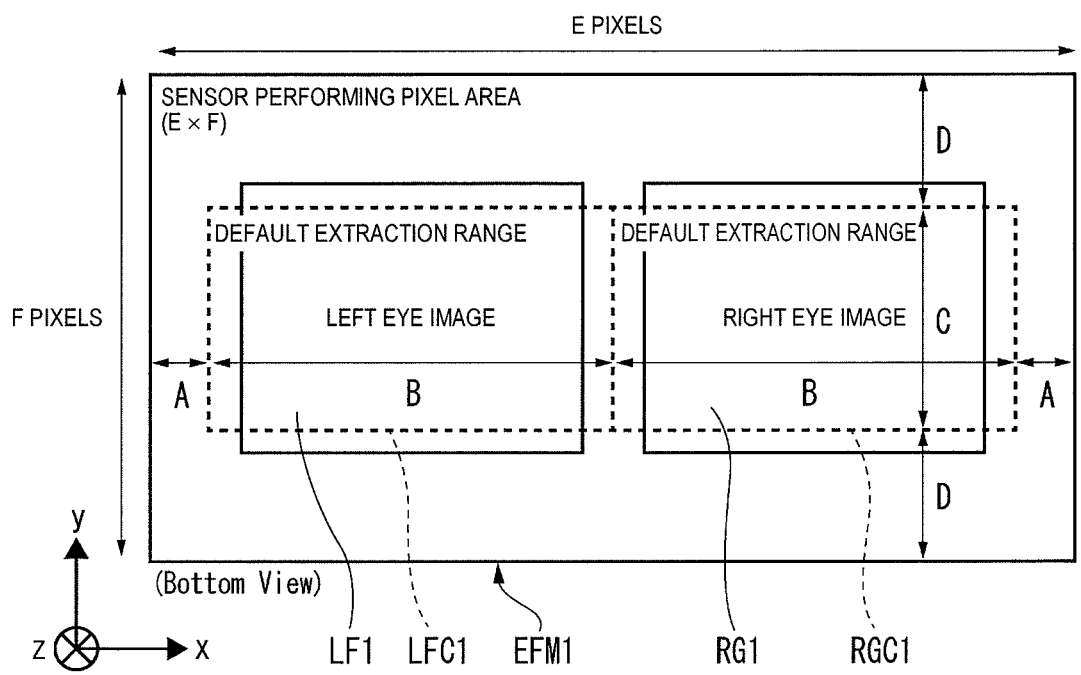
FIG. 9A is an explanatory view of one example of extraction positions of a left eye image and a right eye image under an ideal observation optical system.
Figure 9B:
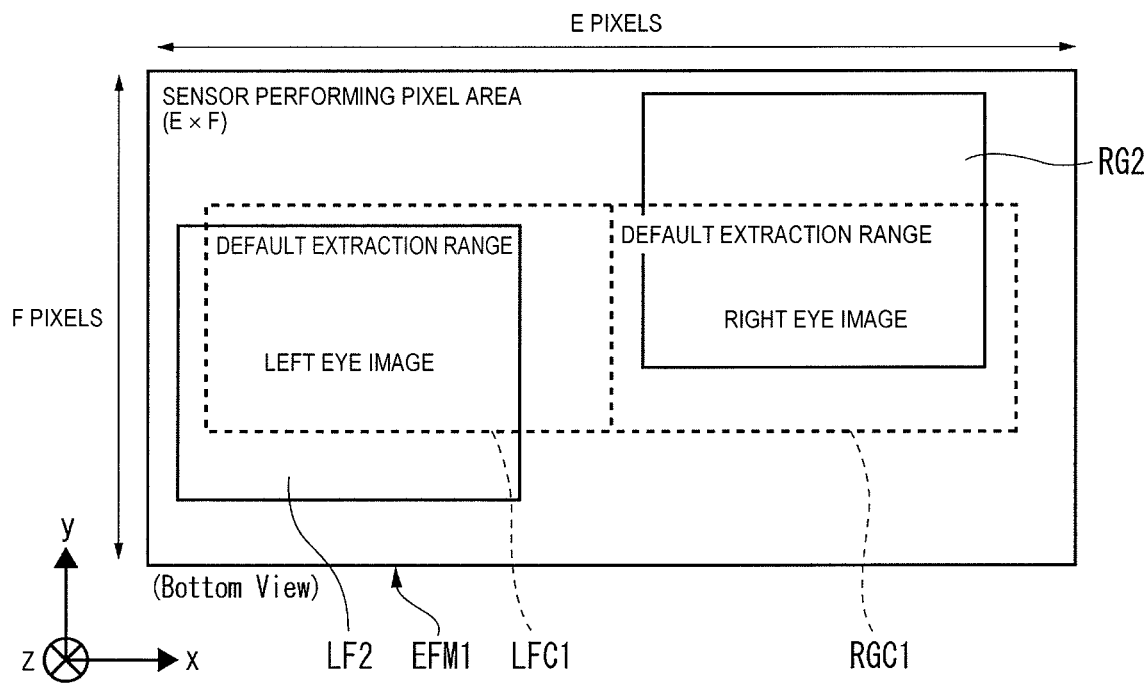
FIG. 9B is an explanatory view of a first example of default extraction positions of a left eye image and a right eye image under a realistic observation optical system.
Figure 9C:
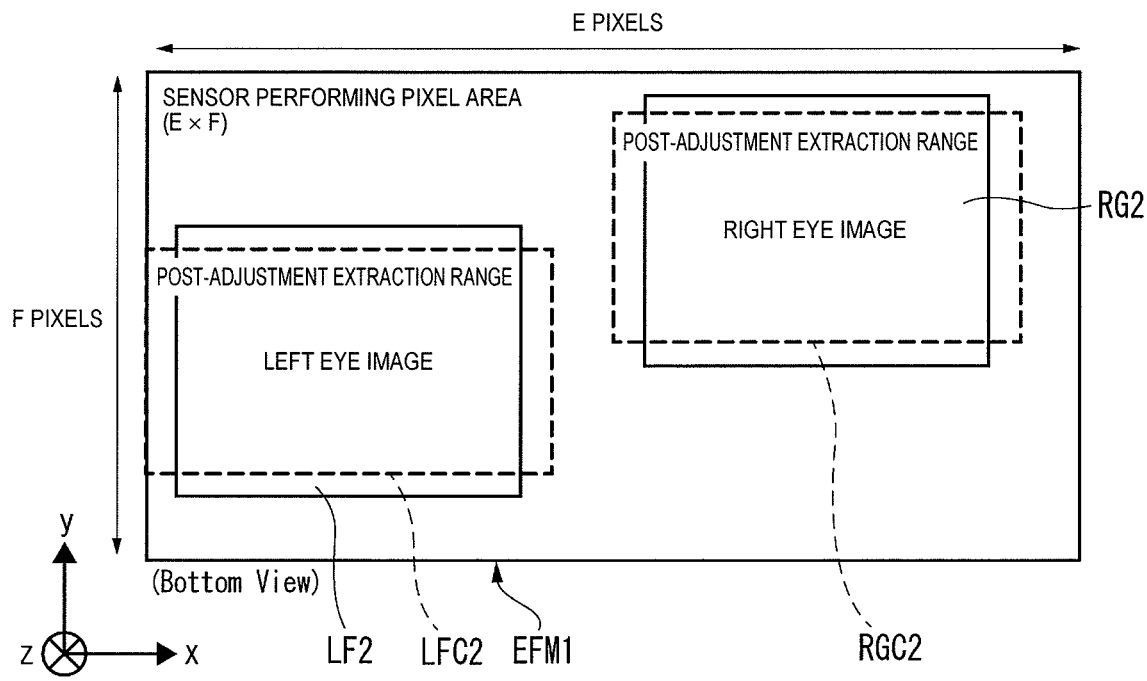
FIG. 9C is an explanatory view of an adjustment example of the extraction position based on an operation of a user with respect to an imaging region of the left eye image and the right eye image illustrated in FIG. 9B.

FIG. 9A is an explanatory view of one example of an extraction position of the left eye image and the right eye image under an ideal observation optical system. FIG. 9B is an explanatory view of a first example of default extraction positions of the left eye image and the right eye image under realistic observation optical system 12. FIG. 9C is an explanatory view of an adjustment example of the extraction position based on the operation of the user with respect to the imaging region of the left eye image and the right eye image illustrated in FIG. 9B.

In FIGS. 9A, 9B, and 9C, sensor effective pixel area EFM1 of the image sensor in camera head 21 is "E pixels×F pixels" (E, F: default value of F<E), the horizontal direction and the vertical direction of sensor effective pixel area EFM1 are defined as an x-axis direction and a y-axis direction, respectively, and the optical axis direction of the observation optical system is defined as the z-axis direction which is perpendicular to the x-axis direction and the y-axis direction. In addition, sensor effective pixel area EFM1 illustrated in FIGS. 9A, 9B, and 9C is a sensor effective pixel area of a so-called bottom view (that is, when the object side is viewed from the imaging surface side). The definitions of the x-axis direction, the y-axis direction, the z-axis direction and the sensor effective pixel area of the bottom view are similarly applied to the descriptions of FIGS. 9D and 9E.

In FIG. 9A, an ideal observation optical system is disposed, and each of a zoom optical system for forming an image of the subject light for obtaining the 2K left parallax video and a zoom optical system for forming an image of the subject light for obtaining the 2K right parallax video is appropriately positioned, and there are no manufacturing variations of the lens itself. Therefore, both 2K left parallax video LF1 (left eye image) and 2K right parallax video RG1 (right eye image) which are obtained by the imaging of the image sensor are extracted by extracting a video as much as default extraction ranges LFC1 and RGC1 which is an initial extraction range. Both default extraction ranges LFC1 and RGC1 are "B pixel×C pixel" (B, C: default value of C<B, smaller than E and F).

In other words, in FIG. 9A, 2K left parallax video LF1 and 2K right parallax video RG1 having the same size (image area) imaged on sensor effective pixel area EFM1 based on the same subject light are extracted so as to have an equivalent size (image area) by default extraction ranges LFC1 and RGC1. This is apparent from the viewpoint that a D pixel (D: default value) that corresponds to a distance between the upper end of default extraction ranges LFC1 and RGC1 and the upper end of sensor effective pixel area EFM1 and a D pixel (D: default value) that corresponds to a distance between the lower end of default extraction ranges LFC1 and RGC1 and the lower end of sensor effective pixel area EFM1, match each other, and that an A pixel (A: default value) that corresponds to a distance between the left end of default extraction range LFC1 and the left end of sensor effective pixel area EFM1 and an A pixel that corresponds to a distance between the right end of default extraction range RGC1 and the right end of sensor effective pixel area EFM1 match each other.

Therefore, the image quality of 2K left parallax video LF1 and 2K right parallax video RG1 of the extracted default extraction ranges LFC1 and RGC1 becomes excellent, and when the observer reads monitor 30 on which the 3D video is displayed based on 2K left parallax video LF1 and 2K right parallax video RG1, camera apparatus 20 can grasp the detailed situation of the observation target site without giving the observer a feeling of strangeness as a 3D video.

Next, in FIG. 9B, each of zoom optical system 101L for forming an image of the subject light for obtaining the 2K left parallax video and zoom optical system 101R for forming an image of the subject light for obtaining the 2K right parallax video is not appropriately positioned, and there are manufacturing variations of the lens itself. Therefore, the 2K left parallax video LF2 (left eye image) and the 2K right parallax video RG2 (right eye image) obtained by imaging of the image sensor are somewhat displaced in the upward-and-downward direction (y-axis direction) and the leftward-and-rightward direction (x-axis direction) as illustrated in FIG. 9B when comparing each position of 2K left parallax video LF1 and 2K right parallax video RG1 which are illustrated in FIG. 9A. Therefore, when 2K left parallax video LF2 and 2K right parallax video RG2 are extracted with default extraction ranges LFC1 and RGC1 at the same positions as in FIG. 9A, extracted 2K left parallax video LF2 and 2K right parallax video RG2 are lack of appropriateness as the video of the same subject, the image quality of each of the upper and right portion of the 2K left parallax video LF2 and the lower portion of the 2K right parallax video RG2 deteriorates. Therefore, when projected on monitor 30, a feeling of strangeness as a 3D video is given to the observer, which is inconvenient.

Here, as illustrated in FIG. 9C, CCU 22 of camera apparatus 20 moves in default extraction range LFC1 in the x-axis direction (horizontal direction) and in the y-axis direction (vertical direction) in accordance with the adjustment signal based on the operation (for example, movement switch 226) of the user (for example, an observer, such as a doctor) who reads 2K left parallax video LF2 and 2K right parallax video RG2 displayed (output to the screen) on monitor 30. Accordingly, CCU 22 saves the position information (coordinate information) of post-adjustment extraction range LFC2 obtained by the movement (adjustment) of the default extraction range LFC1 in set value storage unit 262M, and extracts and outputs 2K left parallax video LC2 of the post-adjustment extraction range LFC2.

Similarly, CCU 22 of camera apparatus 20 moves in default extraction range RGC1 in the y-axis direction (vertical direction) in accordance with the adjustment signal based on the operation (for example, movement switch 226) of the user (for example, an observer, such as a doctor) who reads 2K left parallax video LF2 and 2K right parallax video RG2 displayed (output to the screen) on monitor 30. Accordingly, CCU 22 saves the position information (coordinate information) of post-adjustment extraction range RGC2 obtained by the movement (adjustment) of the default extraction range RGC1 in set value storage unit 262M, and extracts and outputs 2K right parallax video RG2 of the post-adjustment extraction range RGC2. In addition, CCU 22 saves each piece of the position information (coordinate information) of post-adjustment extraction ranges LFC2 and RGC2 in association with each other in set value storage 262M. Accordingly, even in a case where each of the zoom optical system 101L and zoom optical system 101R is not appropriately positioned and there are manufacturing variations of the lens itself, CCU 22 can save the position information of post-adjustment extraction ranges LFC2 and RGC2 which are appropriately determined based on the operation of the user, and thus, it is possible to use the position information as a reference of the extraction range of the subsequent imaged video, and to appropriately manage the imaged video of 2K having left and right parallax.

(Second Adjustment Example of Extraction Range)

Figure 9D:
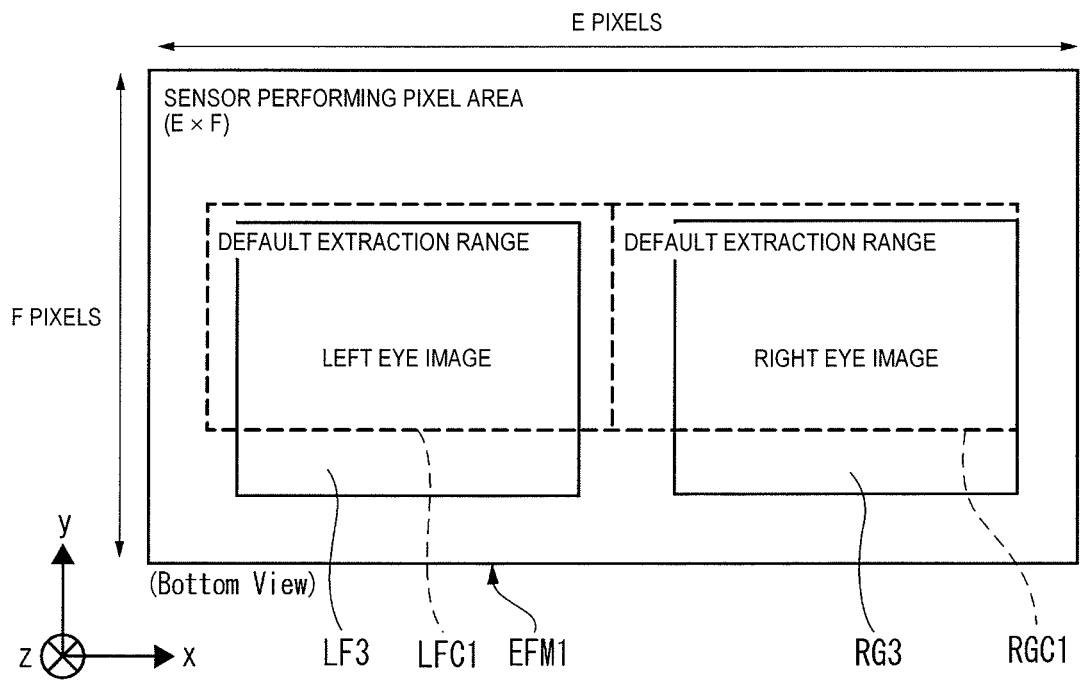
FIG. 9D is an explanatory view of a second example of default extraction positions of a left eye image and a right eye image under the realistic observation optical system.
Figure 9E:
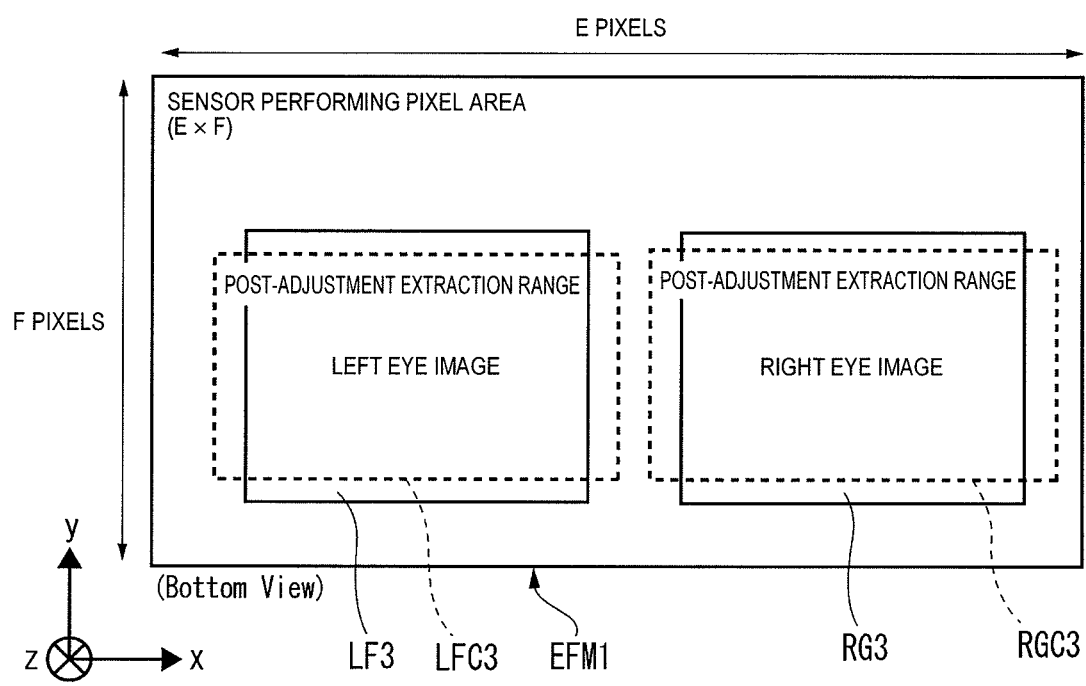
FIG. 9E is an explanatory view of the adjustment example of the extraction position based on the operation of the user with respect to the imaging region of the left eye image and the right eye image illustrated in FIG. 9D.

FIG. 9D is an explanatory view of a second example of default extraction positions of the left eye image and the right eye image under realistic observation optical system 12. FIG. 9E is an explanatory view of the adjustment example of the extraction position based on the operation of the user with respect to the imaging region of the left eye image and the right eye image illustrated in FIG. 9D.

Next, in FIG. 9D, each of zoom optical system 101L for forming an image of the subject light for obtaining the 2K left parallax video and zoom optical system 101R for forming an image of the subject light for obtaining the 2K right parallax video is not appropriately positioned, and there are manufacturing variations of the lens itself. Therefore, 2K left parallax video LF3 (left eye image) and 2K right parallax video RG3 (right eye image) obtained by imaging of the image sensor are somewhat displaced in the upward-and-downward direction (y-axis direction) and the leftward-and-rightward direction (x-axis direction) as illustrated in FIG. 9D when comparing each position of 2K left parallax video LF1 and 2K right parallax video RG1 which are illustrated in FIG. 9A. Therefore, when 2K left parallax video LF3 and 2K right parallax video RG3 are extracted with default extraction ranges LFC1 and RGC1 at the same positions as in FIG. 9A, extracted 2K left parallax video LF3 and 2K right parallax video RG3 are lack of appropriateness as the video of the same subject, the image quality of each of the upper and right portion of the 2K left parallax video LF3 and the lower portion of the 2K right parallax video RG3 deteriorates. Therefore, when projected on monitor 30, a feeling of strangeness as a 3D video is given to the observer, which is inconvenient.

Here, as illustrated in FIG. 9E, CCU 22 of camera apparatus 20 moves in default extraction range LFC1 in the y-axis direction (vertical direction) in accordance with the adjustment signal based on the operation (for example, movement switch 226) of the user (for example, an observer, such as a doctor) who reads 2K left parallax video LF3 and 2K right parallax video RG3 displayed (output to the screen) on monitor 30. Accordingly, CCU 22 saves the position information (coordinate information) of post-adjustment extraction range LFC3 obtained by the movement (adjustment) of the default extraction range LFC1 in set value storage unit 262M and extracts and outputs 2K left parallax video LC3 of the post-adjustment extraction range LFC3.

Similarly, CCU 22 of camera apparatus 20 moves in default extraction range RGC1 in the y-axis direction (vertical direction) in accordance with the adjustment signal based on the operation (for example, movement switch 226) of the user (for example, an observer, such as a doctor) who reads 2K left parallax video LF3 and 2K right parallax video RG3 displayed (output to the screen) on monitor 30. Accordingly, CCU 22 saves the position information (coordinate information) of post-adjustment extraction range RGC3 obtained by the movement (adjustment) of the default extraction range RGC1 in set value storage unit 262M and extracts and outputs 2K right parallax video RG3 of the post-adjustment extraction range RGC3. Further, CCU 22 saves each piece of the position information (coordinate information) of post-adjustment extraction ranges LFC3 and RGC3 in association with each other in set value storage unit 262M. Accordingly, even in a case where each of the zoom optical system 101L and zoom optical system 101R is not appropriately positioned and there are manufacturing variations of the lens itself, CCU 22 can save the position information of post-adjustment extraction ranges LFC3 and RGC3 which are appropriately determined based on the operation of the user, and thus, it is possible to use the position information as a reference of the extraction range of the subsequent imaged video, and to appropriately manage the imaged video of 2K having left and right parallax.

Above, in the medical camera system of Embodiment 1, CCU 22 is connected to the camera head which can perform the imaging on the imaging surface of one screen of the 2K left parallax video (one example of the left eye image) and 2K right parallax video (one example of the right eye image) having parallax based on the light of the target site incident on surgical microscope 10 (one example of the optical instrument). CCU 22 or camera apparatus 20 including CCU 22 performs the signal processing of the left eye image and the right eye image which are imaged by camera head 21, and outputs the left eye image and the right eye image to which the signal processing is performed to monitor 30. In addition, CCU 22 or camera apparatus 20 including CCU 22 adjusts the extraction position of at least one of the left eye image and the right eye image in accordance with the operation of the user based on the left eye image and the right eye image displayed on monitor 30.

Accordingly, CCU 22 or camera apparatus 20 including CCU 22 can electronically extract parts having excellent image quality from each of the left eye image and the right eye image which configure the 3D video by a simple operation of the user who reads the left eye image and the right eye image displayed on monitor 30, and can image and output a high definition 3D video with one camera. In addition, it is possible to image and output a high definition 3D video of 2K pixels with one camera head 21 and CCU 22, and to project the target site stereographically and with high definition. In particular, for surgical applications, clearer 3D video can be acquired, and operability at the time of surgery and visibility of the target site can be improved.

In addition, since one CCU 22 can cope with imaging output of 2D video of 4K pixels and imaging output of 3D video of 2K pixels, the disclosure can be applied to various observation video applications.

In addition, CCU 22 or camera apparatus 20 including CCU 22 saves the adjustment result of the extraction position of at least one of the left eye image and the right eye image in set value storage 262M. Accordingly, even in a case where each of zoom optical system 101L and zoom optical system 101R is not appropriately positioned and there are manufacturing variations of the lens itself, CCU 22 or camera apparatus 20 including CCU 22 can save the position information of the post-adjustment extraction range which are appropriately determined based on the operation of the user, and thus, it is possible to use the position information as a reference of the extraction range of the subsequent imaged video, and to appropriately manage the imaged video of 2K having left and right parallax.

In addition, CCU 22 or camera apparatus 20 including CCU 22 adjusts the extraction position in the horizontal direction of at least one of the left eye image and the right eye image by camera head 21 in accordance with the operation of the user who reads the left eye image and the right eye image displayed on monitor 30. Accordingly, CCU 22 or camera apparatus 20 including CCU 22 can extract a video of the post-adjustment extraction range which is appropriately determined based on the operation of the user even in a case where at least one of the 2K left parallax video and the 2K right parallax video is imaged in the horizontal direction being shifted from the default extraction range, can appropriately adjust the depth feeling (stereoscopic feeling) of 3D, and can acquire a video having excellent image quality.

In addition, CCU 22 or camera apparatus 20 including CCU 22 adjusts the extraction position in the vertical direction of at least one of the left eye image and the right eye image by camera head 21 in accordance with the operation of the user who reads the left eye image and the right eye image displayed on monitor 30. Accordingly, CCU 22 or camera apparatus 20 including CCU 22 can extract a video of the post-adjustment extraction range which is appropriately determined based on the operation of the user even in a case where at least one of the 2K left parallax video and the 2K right parallax video is imaged in the vertical direction being shifted from the default extraction range, can appropriately perform adjustment so as to have the qualification as a 3D video, and can acquire a video having excellent image quality.

In addition, CCU 22 or camera apparatus 20 including CCU 22 adjusts the extraction position in the horizontal direction or in the vertical direction of both of the left eye image and the right eye image by camera head 21 in accordance with the operation of the user who reads the left eye image and the right eye image displayed on monitor 30. Accordingly, CCU 22 or camera apparatus 20 including CCU 22 can extract a video of the post-adjustment extraction range which is appropriately determined based on the operation of the user even in a case where both of the 2K left parallax video and the 2K right parallax video are imaged in the horizontal direction or in the vertical direction being shifted from the default extraction range, can appropriately perform adjustment so as to have the depth feeling (stereoscopic feeling) of 3D and the qualification as a 3D video, and can acquire a video having excellent image quality.

Further, in the 3D mode, CCU 22 or camera apparatus 20 including CCU 22 includes distance measuring circuit 291 (one example of distance measurer) which measures distance L (refer to FIG. 19) from surgical endoscope 110 (one example of optical instrument) to an observation target site based on the parallax Δ (refer to FIG. 23) appearing in the left eye image and the right eye image which are imaged by camera head 21. CCU 22 or camera apparatus 20 outputs the result measured by distance measuring circuit 291 (that is, information on the distance) to monitor 130 (refer to FIG. 19) together with the left eye image and the right eye image to which the signal processing is performed. Accordingly, the user (for example, an observer, such as a doctor) can visually grasp the situation of the observation target site projected to monitor 130, can grasp the specific distance information from surgical endoscope 110 (refer to FIG. 19) to the observation target site, and can support the guidance of the next medical practice by the user at the time of surgery or examination.

In addition, in response to the switching from the 3D mode to the 2D mode, CCU 22 or camera apparatus 20 including CCU 22 interrupts the output of the information on the distance to monitor 130. Accordingly, in the 2D mode, neither the left and right 2K left parallax video having parallax nor the 2K right parallax video is input to distance measuring circuit 291, and thus, the information on the distance is not displayed on monitor 130. Therefore, the user (for example, an observer, such as a doctor) can easily recognize that the present is the 2D mode by the fact that the information on the distance is not displayed on monitor 130, and on the other hand, the user can easily recognize that the present is the 3D mode by the fact that the information on the distance is displayed on monitor 130.

(Background of Contents of Embodiment 2)

In the above-described medical camera system, in order to ensure a clear field of view of a target site at which surgery or treatment is performed, a display video with high definition and excellent visibility is desired. In addition, since the size or state of an observation target can be grasped more accurately and easily by stereoscopic viewing of a target site, there is an increasing demand for a 3D video that provides a stereoscopic observed video to the observer. Particularly, in a surgical application of a fine site, a high-definition 3D video is required, but in the related art, such as PTL 1, there was a problem that it is difficult to visually recognize the details of the observed video clearly. In addition, in order to generate a high-definition 3D video required in the medical field, it is necessary to use two different cameras for imaging an image for a left eye (left eye image) and an image for a right eye (right eye image) which have parallax.

In addition, for example, in a medical camera system, visibility of video displayed on a monitor is particularly important for a doctor or the like to grasp the details of the situation of a target site (for example, an affected part of a human body). The video displayed on the monitor at the time of surgery or examination is appropriately switched between the 2D video capable of planar viewing and the 3D video capable of stereoscopic viewing. Here, in the related art as in PTL 1, since it is not considered to switch from 2D video to 3D video as the video displayed on the monitor, the following problems are caused when switching from the display of the 2D video to the display of the 3D video. First, in order to improve the image quality (that is, visibility) of the video, various types of signal processing (for example, automatic exposure processing, such as auto exposure (AE)) or adjustment processing of white balance (WB), are performed with respect to the imaged video. However, at the time of switching from the display of 2D video to the display of 3D video, when an area on an imaging surface used for deriving parameters of the signal processing of the 2D video is used as it is as an area used for deriving parameters of the signal processing of the 3D video, there is a case where the 3D video having appropriate image quality cannot be obtained.

Here, in Embodiment 2 which will be described below, considering the above-described situation of the related art, an example of the image processing apparatus, the camera apparatus, and the image processing method which are capable of adaptively adjusting the area on the imaging surface used for deriving parameters of signal processing with respect to the imaged 3D video when switching from display of the 2D video to display of the 3D video, and imaging and outputting a high-definition 3D video with one camera will be described.

Embodiment 2

Since the internal configuration of each of the medical camera system and the camera apparatus or the CCU of Embodiment 2 is the same as the internal configuration of each of the medical camera system and camera apparatus 20 or CCU 22 of Embodiment 1, the same configuration will be given the same reference numerals and the description thereof will be simplified or omitted, and different contents will be described.

First, in Embodiment 2, as an example of signal processing performed with respect to an imaged video in order to improve the image quality of the video, an automatic exposure processing, such as auto exposure (AE), is exemplified, and an example in which, in a case of switching from the 2D mode to the 3D mode, an area used for used for deriving parameters (for example, brightness or light amount) of the automatic exposure processing is determined, will be described. In addition, the configuration of the CCU of Embodiment 2 is combined with the configuration of the CCU of Embodiment 1, and after the extraction range of the left eye image and the right eye image is adjusted by the configuration of the CCU of Embodiment 1, it is needless to say that various controls of automatic exposure processing, such as AE and adjustment processing of WB may be performed according to the configuration of the CCU of Embodiment 2.

Figure 10:
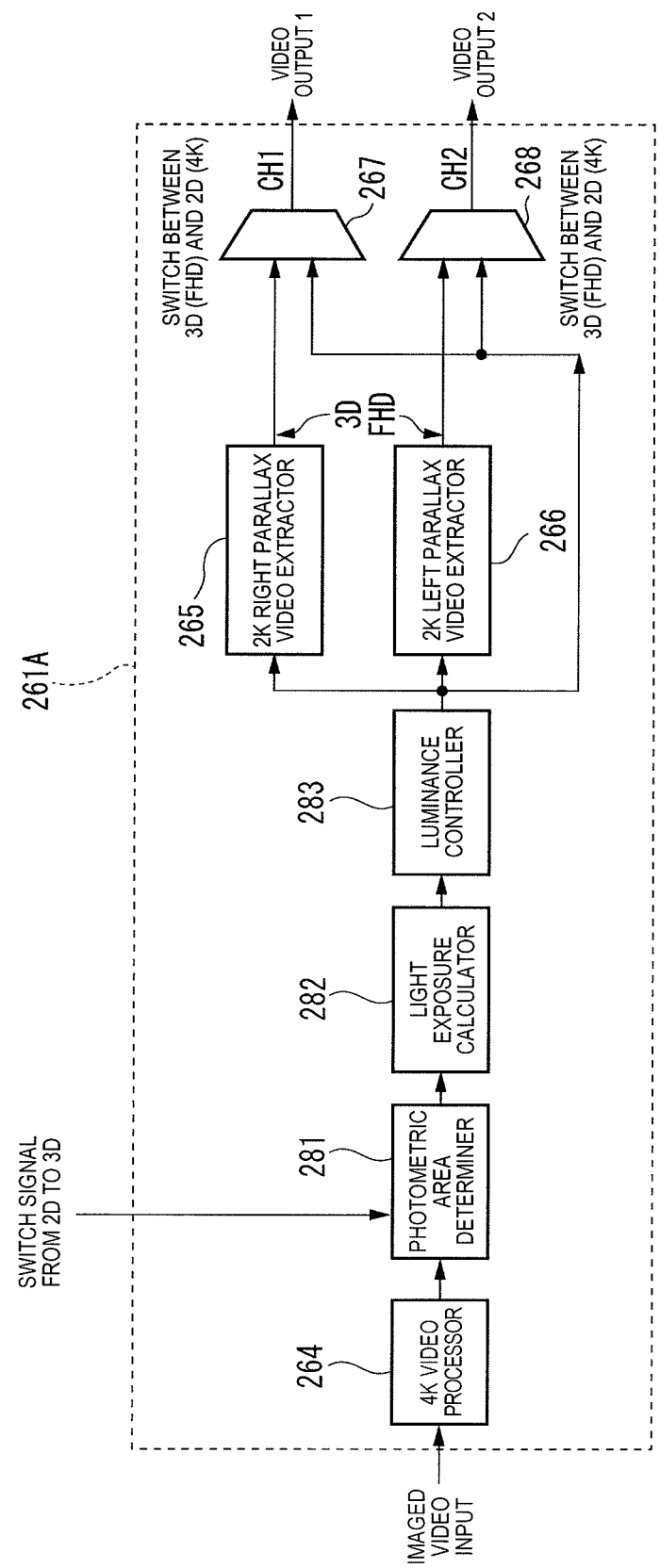
FIG. 10 is a block diagram illustrating a first example of a functional configuration of an image processor of a camera apparatus of Embodiment 2.

FIG. 10 is a block diagram illustrating a first example of a functional configuration of the image processor of camera apparatus 20 of Embodiment 2. Image processor 261A includes 4K video processor 264, photometric area determiner 281, light exposure calculator 282, luminance controller 283, 2K left parallax video extractor 265, 2K right parallax video extractor 266, and video output switchers 267 and 268. In addition, although frame buffer FB1 (memory) is not illustrated and omitted in FIG. 10, when frame buffer FB1 is provided in CCU 22, frame buffer FB1 may be provided either on the inside or on the outside of image processor 261A.

The video data of 4K pixels generated by 4K video processor 264 is input to photometric area determiner 281.

In accordance with a switching signal from the 2D mode to the 3D mode, photometric area determiner 281 (one example of a determiner) determines an area used for deriving parameters (for example, brightness or light amount) of the signal processing (for example, automatic exposure processing, such as AE) with respect to the left eye image and the right eye image (for example, video data of 4K pixels generated by 4K video processor 264) which are imaged by camera head 21 (refer to FIGS. 11A, 11B, 11C, and 11D). Further, in accordance with a switching signal from the 3D mode to the 2D mode, photometric area determiner 281 determines an area used for deriving parameters (for example, brightness or light amount) of the signal processing (for example, automatic exposure processing, such as AE) with respect to the left eye image and the right eye image (for example, video data of 4K pixels generated by 4K video processor 264) which are imaged by camera head 21. In addition, even when the switching from the 2D mode to the 3D mode or the switching from the 3D mode to the 2D mode does not occur, photometric area determiner 281 determines an area used for deriving parameters (for example, brightness or light amount) of the signal processing (for example, automatic exposure processing, such as AE) with respect to the left eye image and the right eye image (for example, video data of 4K pixels generated by 4K video processor 264) which are imaged by camera head 21.

Figure 11A:
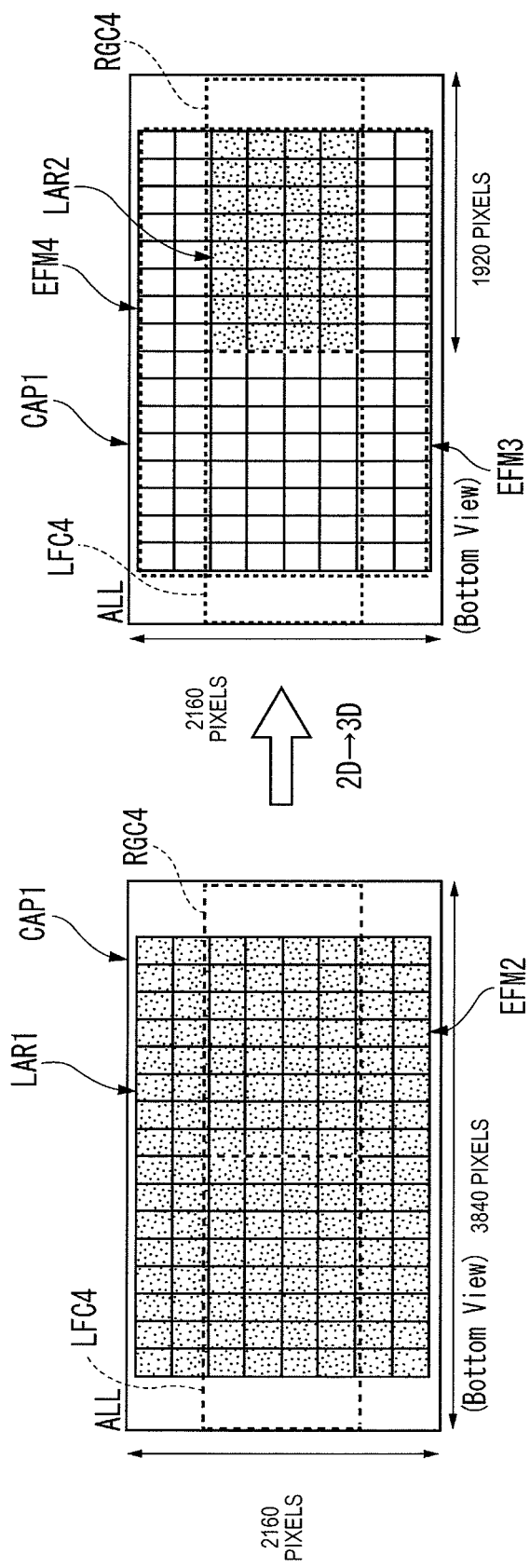
FIG. 11A is an explanatory view illustrating an adjustment example of a photometric area of automatic exposure with respect to a first subject in accordance with switching from a 2D mode to a 3D mode.
Figure 11B:
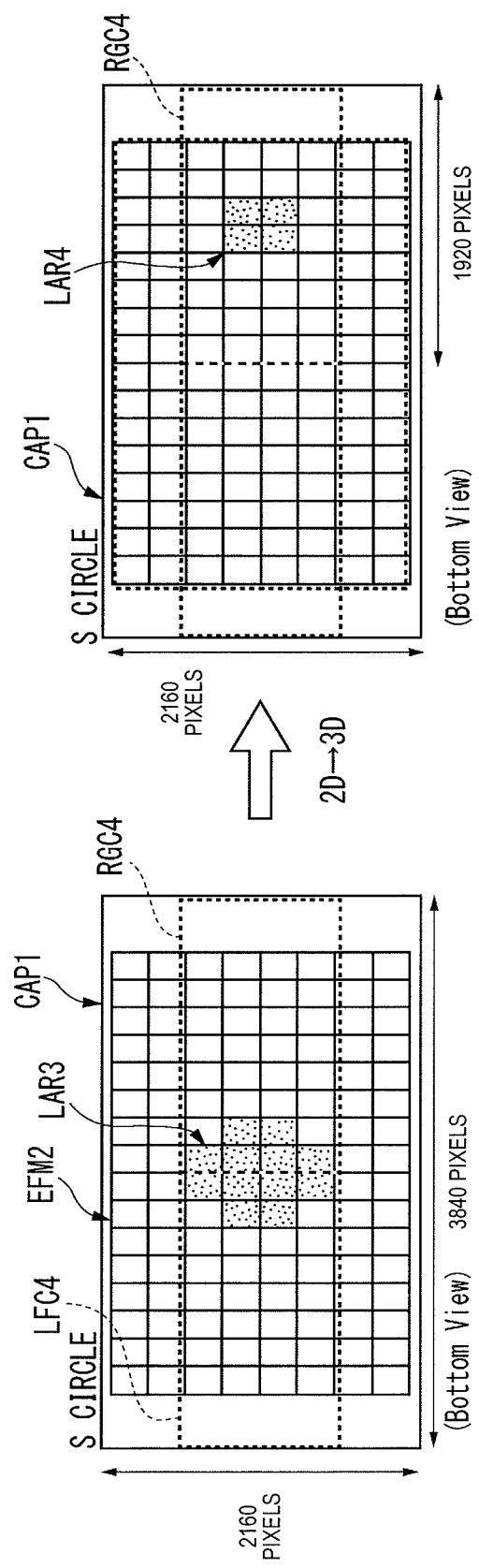
FIG. 11B is an explanatory view illustrating an adjustment example of a photometric area of automatic exposure with respect to a second subject in accordance with switching from the 2D mode to the 3D mode.
Figure 11D:
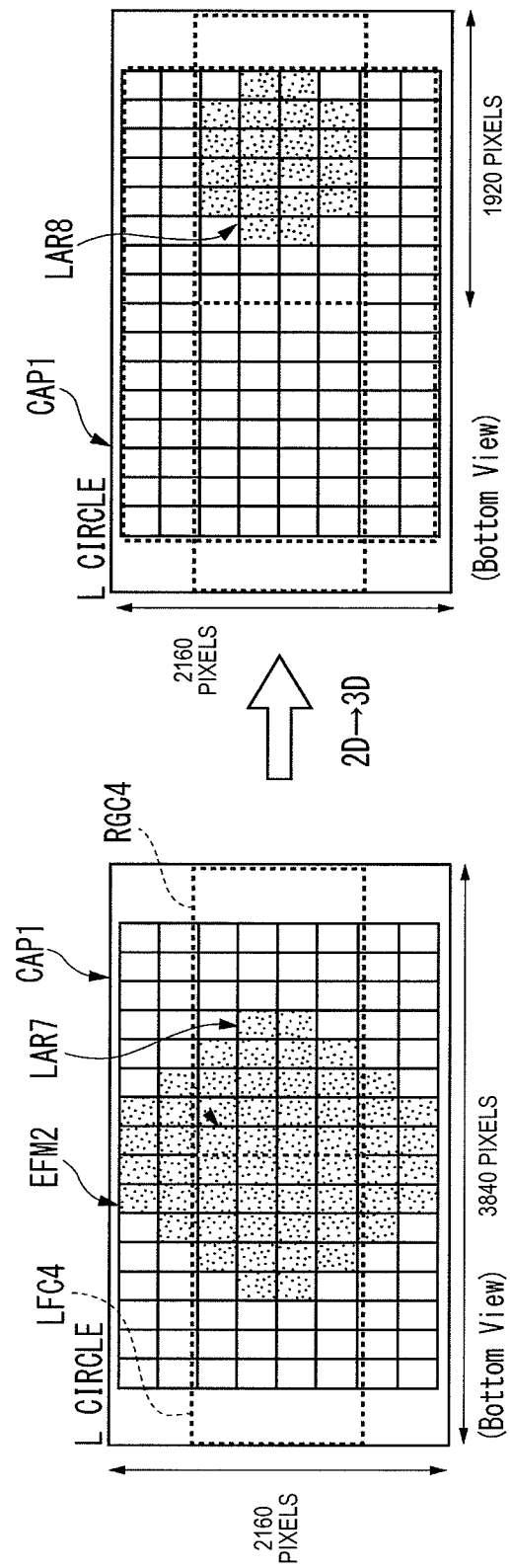
FIG. 11D is an explanatory view illustrating an adjustment example of a photometric area of automatic exposure with respect to a fourth subject in accordance with switching from the 2D mode to the 3D mode.

FIG. 11A is an explanatory view illustrating an adjustment example of a photometric area of automatic exposure with respect to a first subject in accordance with the switching from the 2D mode to the 3D mode. FIG. 11B is an explanatory view illustrating an adjustment example of a photometric area of automatic exposure with respect to a second subject in accordance with the switching from the 2D mode to the 3D mode. FIG. 11C is an explanatory view illustrating an adjustment example of a photometric area of automatic exposure with respect to a third subject in accordance with the switching from the 2D mode to the 3D mode. FIG. 11D is an explanatory view illustrating an adjustment example of a photometric area of automatic exposure with respect to a fourth subject in accordance with the switching from the 2D mode to the 3D mode.

In FIGS. 11A to 11D, in imaging surface CAP1 of the image sensor in camera head 21 (for example, the size of "2160 pixels×3840 pixels" that corresponds to 4K pixels), sensor effective pixel region EFM2 which corresponds to the largest pixel region used in imaging the video is provided. In FIGS. 11A to 11D, imaging surface CAP1 is an imaging surface of a so-called bottom view (that is, when the object side is viewed from the imaging surface side). In addition, here, in order to simplify the description of FIGS. 11A to 11D, extraction range LFC4 of the 2D left parallax video which configures the 3D video and extraction range RGC4 of the 2D right parallax video which configures the same 3D video, are set in a state where there is no shift in the vertical direction of imaging surface CAP1 and of being horizontally aligned in the horizontal direction. Extraction range LFC4 is an extraction range of the 2K left parallax video (left eye image) in sensor effective pixel area EFM3 for the 2K left parallax video (left eye image). Similarly, extraction range RGC4 is the extraction range of the 2K right parallax video (right eye image) in sensor effective pixel area EFM4 for the 2K right parallax video (right eye image). In addition, in the description of FIGS. 11A to 11D, sensor effective pixel region EFM2 is assumed to be configured with a total of 128 regions divided by 8 in the vertical direction×16 in the horizontal direction.

On the left side of the page of FIG. 11A, a case where the imaging of the 2D video is performed over the entire sensor effective pixel region EFM2 in the 2D mode, is illustrated. As illustrated in FIG. 11A, in a case where the imaging of the 2D video is performed over the entire sensor effective pixel region EFM2, the entire sensor effective pixel region EFM2 is used for deriving (calculating) parameters (for example, brightness or light amount) of the automatic exposure processing (one example of the signal processing) of the 2D video (refer to photometric area LAR1 indicated by the dot hatch in FIG. 11A). In accordance with the operation of the user for the switching from the 2D mode to the 3D mode (that is, the switching signal from the 2D mode to the 3D mode), as illustrated on the right side of the page of FIG. 11A, photometric area determiner 281 determines, for example, the size of extraction range RGC4 of 2K right parallax video LAR2 which configures the 3D video as the photometric area used for deriving parameters (for example, brightness or light amount) of the signal processing (for example, automatic exposure processing, such as AE) with respect to the video data (that is, 2K left parallax video and 2K right parallax video) of 4K pixels generated by 4K video processor 264. In addition, photometric area determiner 281 may determine, for example, the size of extraction range LFC4 of the 2K left parallax video which configures the 3D video as the photometric area.

On the left side of the page of FIG. 11B, a case where the imaging of 2D video LAR3 is performed over a small area (for example, 12 squares) including the center of sensor effective pixel region EFM2 in the 2D mode, is illustrated. As illustrated in FIG. 11B, in a case where the imaging of 2D video LAR3 is performed over a small area including the center of sensor effective pixel region EFM2, the entire sensor effective pixel region EFM2 is used for deriving (calculating) the parameters (for example, brightness or light amount) of the automatic exposure processing (one example of the signal processing) of the 2D video (refer to photometric area LAR1 indicated by the dot hatch of FIG. 11A). Here, in accordance with the operation of the user for switching from the 2D mode to the 3D mode (that is, the switching signal from the 2D mode to the 3D mode), as illustrated on the right side of the page of FIG. 11B, photometric area determiner 281 determines, for example, the size of extraction range RGC4 of 2K right parallax video LAR4 which configures the 3D video as the photometric area used for deriving the parameters (for example, brightness or light amount) of the signal processing (for example, automatic exposure processing, such as AE) with respect to the video data (that is, 2K left parallax video and 2K right parallax video) of 4K pixels generated by 4K video processor 264. In addition, photometric area determiner 281 may determine, for example, the size of extraction range LFC4 of the 2K left parallax video which configures the 3D video as the photometric area.

On the left side of the page of FIG. 11C, a case where the imaging of 2D video LAR5 is performed over a medium area (for example, 24 squares) including the center of sensor effective pixel region EFM2 in the 2D mode, is illustrated. As illustrated in FIG. 11C, in a case where the imaging of 2D video LAR5 is performed over a medium area including the center of sensor effective pixel region EFM2, the entire sensor effective pixel region EFM2 is used for deriving (calculating) parameters (for example, brightness or light amount) of the automatic exposure processing (one example of the signal processing) of the 2D video (refer to photometric area LAR1 indicated by the dot hatch of FIG. 11A). Here, in accordance with the operation of the user for switching from the 2D mode to the 3D mode (that is, the switching signal from the 2D mode to the 3D mode), as illustrated on the right side of the page of FIG. 11C, photometric area determiner 281 determines, for example, the size of extraction range RGC4 of 2K right parallax video LAR6 which configures the 3D video as the photometric area used for deriving parameters (for example, brightness or light amount) of the signal processing (for example, automatic exposure processing, such as AE) with respect to the video data (that is, 2K left parallax video and 2K right parallax video) of 4K pixels generated by 4K video processor 264. In addition, photometric area determiner 281 may determine, for example, the size of extraction range LFC4 of the 2K left parallax video which configures the 3D video as the photometric area.

On the left side of the page of FIG. 11D, a case where the imaging of 2D video LAR7 is performed over a large area (for example, 56 squares) including the center of sensor effective pixel region EFM2 in the 2D mode, is illustrated. As illustrated in FIG. 11D, in a case where the imaging of 2D video LAR7 is performed over a medium area including the center of sensor effective pixel region EFM2, the entire sensor effective pixel region EFM2 is used for deriving (calculating) parameters (for example, brightness or light amount) of the automatic exposure processing (one example of the signal processing) of the 2D video (refer to photometric area LAR1 indicated by the dot hatch of FIG. 11A). Here, in accordance with the operation of the user for switching from the 2D mode to the 3D mode (that is, the switching signal from the 2D mode to the 3D mode), as illustrated on the right side of the page of FIG. 11D, photometric area determiner 281 determines, for example, the size of extraction range RGC4 of 2K right parallax video LAR8 which configures the 3D video as the photometric area used for deriving parameters (for example, brightness or light amount) of the signal processing (for example, automatic exposure processing, such as AE) with respect to the video data (that is, 2K left parallax video and 2K right parallax video) of 4K pixels generated by 4K video processor 264. In addition, photometric area determiner 281 may determine, for example, the size of extraction range LFC4 of the 2K left parallax video which configures the 3D video as the photometric area.

Exposure calculator 282 (one example of a deriver) calculates an exposure amount (that is, brightness or light amount) in the photometric area of the data of the 2D video of 4K pixels generated by 4K video processor 264 considering the photometric area determined by photometric area determiner 281 as a target, and outputs the calculation result to luminance controller 283. In addition, exposure calculator 282 may not be provided in image processor 261A, or may be provided in CPU 262.

By using the calculation result of exposure calculator 282, luminance controller 283 (one example of the image processor) performs the automatic exposure processing, such as AE, with respect to the 2D video of 4K pixels generated by 4K video processor 264. In other words, luminance controller 283 performs processing of increasing the brightness for setting appropriate brightness in a case where the 2D video of 4K pixels in the photometric area is excessively dark (for example, the exposure amount is less than the predetermined first threshold value, and the first threshold value is the predetermined value). Meanwhile, luminance controller 283 performs processing of reducing the brightness for setting appropriate brightness in a case where the 2D video of 4K pixels in the photometric area is excessively bright (for example, the exposure amount is equal to or greater than the predetermined second threshold value, and the second threshold value is the predetermined value that satisfies first threshold value<second threshold value). In addition, luminance controller 283 may not be provided in image processor 261A, or may be provided in CPU 262. Luminance controller 283 outputs data of the 2D video of 4K pixels which is the processing result of the automatic exposure processing, such as AE, to 2K right parallax video extractor 265 and 2K left parallax video extractor 266, respectively.

Since the processing contents of 2K right parallax video extractor 265, 2K left parallax video extractor 266, and video output switchers 267 and 268 are the same as those in Embodiment 1, the description thereof will be omitted here.

Figure 12:
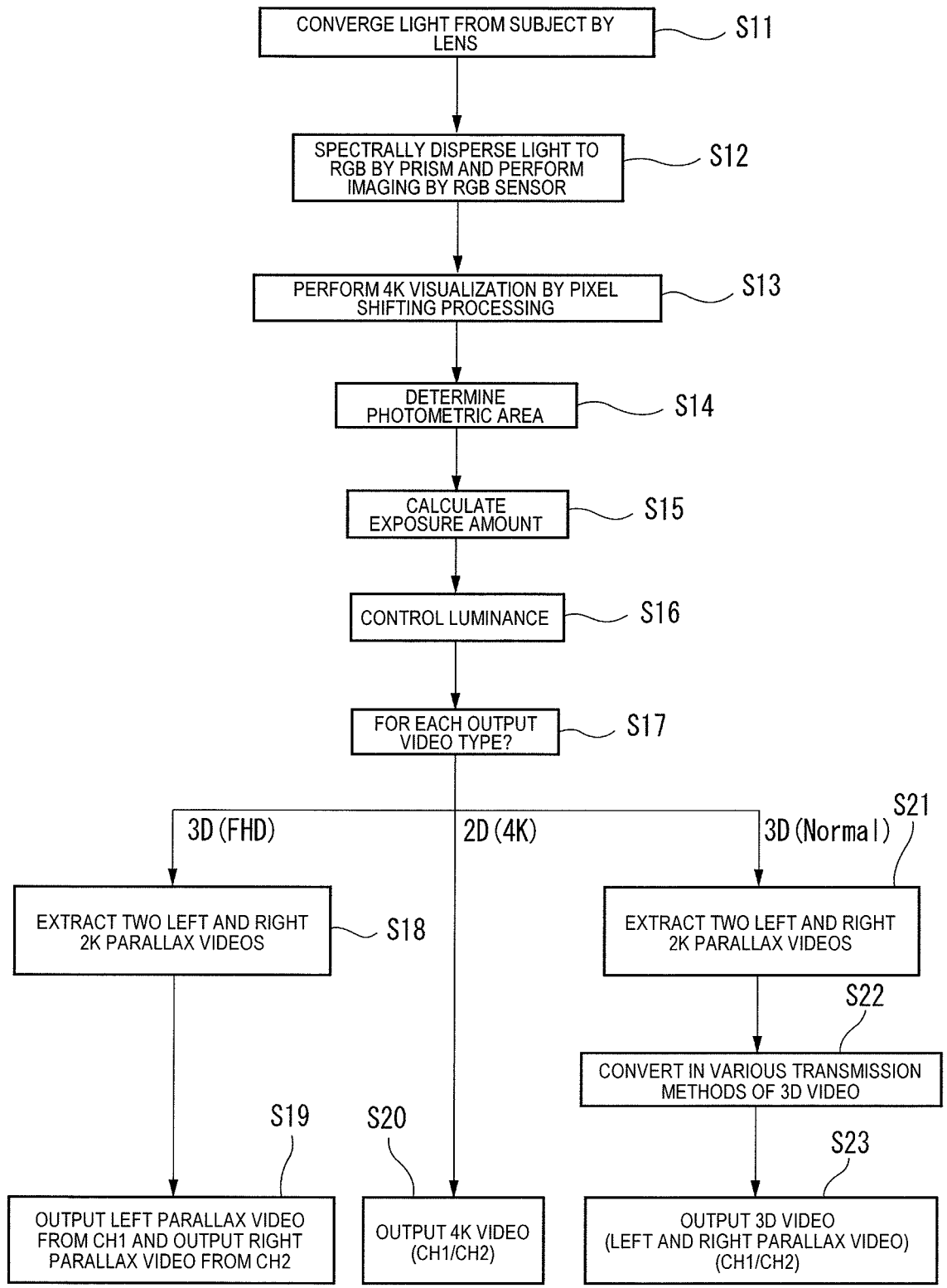
FIG. 12 is a flowchart for describing an operational procedure example of the camera apparatus of Embodiment 2.

FIG. 12 is a flowchart for describing an operational procedure example of camera apparatus 20 of Embodiment 2. In addition, in the description of FIG. 12, during the processing of steps S11 to S23, the processing in steps S11 and S12 is performed in camera head 21 of camera apparatus 20, and the processing after step S13 is performed in CCU 22 of camera apparatus 20. Further, it is needless to say that the operation in FIG. 12 is not the contents dedicated to Embodiment 2, but can be applied as a processing procedure for the video after the extraction range is set in Embodiment 1.

In FIG. 12, camera apparatus 20 converges the light from subject 40 acquired by surgical microscope 10 with the lens of imaging lens portion 23 (S11). In three-plate type capture 213 of camera head 21, camera apparatus 20 spectrally disperses the light to the subject image of each color of RGB by a spectroscopic prism, forms an image on the imaging surfaces of the three image sensors of RGB, respectively, and images subject images of RGB of 2K pixels (S12).

In image processor 261A of CCU 22, camera apparatus 20 generates 4K video (video of 4K pixels) by 4K visualization by the processing of pixel shifting the imaged 2K videos R, G, and B of each color of R, G, and B (S13). In image processor 261A of the CCU 22, camera apparatus 20 determines an area used for deriving parameters (for example, brightness or light amount) of the signal processing (for example, automatic exposure processing, such as AE) with respect to the video of 4K pixels generated in step S13 (S14).

In image processor 261A of CCU 22, camera apparatus 20 calculates the exposure amount (that is, brightness or light amount) in the photometric area of the data of the 2D video of 4K pixels generated in step S13, considering the photometric area determined in step S14 as a target (S15). In image processor 261A of CCU 22, camera apparatus 20 performs the automatic exposure processing, such as AE, with respect to the data of 2D video of 4K pixels generated in step S13 by using the calculation result of the exposure amount in step S15 (S16).

Camera apparatus 20 determines the output video type in CPU 262 of CCU 22. In addition, CPU 262 controls the imaging by capture 213 and can determine the output video type of the video imaged by the capture 213. Camera apparatus 20 sets the operation of image processor 261A and switches the video output for each output video type of 3D video of 2K pixels (3D (FHD)), 2D video of 4K pixels (2D(4K)), and 3D video of HD resolution (3D (normal)) (S17).

In a case of outputting the 3D video (3D (FHD)) of 2K pixels, image processor 261A of CCU 22 performs the extraction processing of two left and right 2K parallax videos (2K left parallax video and 2K right parallax video) (S18). Image processor 261A of CCU 22 outputs the 3D left parallax video from channel CH1 as a 3D video output of 2K pixels for 3D display and outputs the 3D right parallax video from channel CH2 (S19).

In a case of outputting the 2D video (2D (4K)) of 4K pixels, image processor 261A of CCU 22 outputs the 4K video as a 2D video output of 4K pixels from either or both of channel CH1 and channel CH2 (S20).

In a case of outputting the 3D video (3D (normal)) of HD resolution, image processor 261A of CCU 22 performs the extraction processing of two left and right 2K parallax videos (2K left parallax video and 2K right parallax video) (S21). In the processing of the step S21, as described in Embodiment 1, at least one extraction region of the 2K left parallax video and the 2K right parallax video may be extracted individually after being adjusted, in accordance with the operation of the user (for example, an observer, such as a doctor). Image processor 261A combines the two left and right 2K parallax videos and performs video conversion processing (3D image visualization processing) that corresponds to various transmission methods of the 3D video (S22). Image processor 261A outputs the 3D video (left and right parallax video) as the 3D video output of HD resolution (S23).

Figure 21:
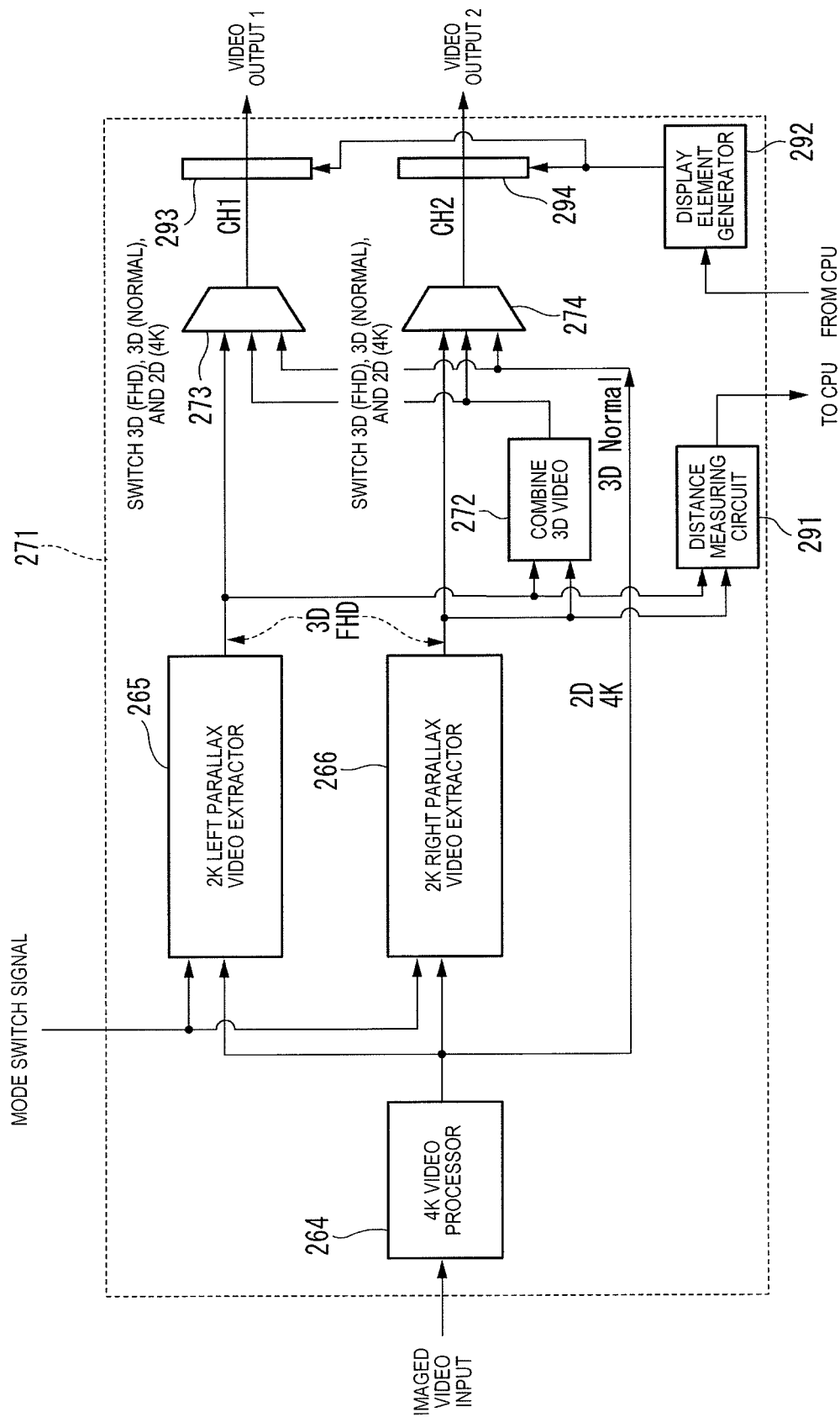
FIG. 21 is a block diagram illustrating a functional configuration example of an image processor of a camera apparatus of Embodiment 4.

Here, in a case where the processing of step S22 is performed, image processor 261A includes 3D video combiner 272 illustrated in FIG. 21. 3D video combiner 272 performs combining processing of the 2D left parallax video from 2K left parallax video extractor 265 and the 2D right parallax video from 2K right parallax video extractor 266, and generates a 3D video of HD resolution (3D (normal)). The combining processing of the 3D video can be performed by using video conversion processing (3D visualization processing) that corresponds to various transmission methods of the 3D video, such as a side-by-side method in which the left parallax video and the right parallax video are adjacent to each other in the horizontal direction, or a line by line method in which the left parallax video and the right parallax video are disposed for each line.

Figure 13:
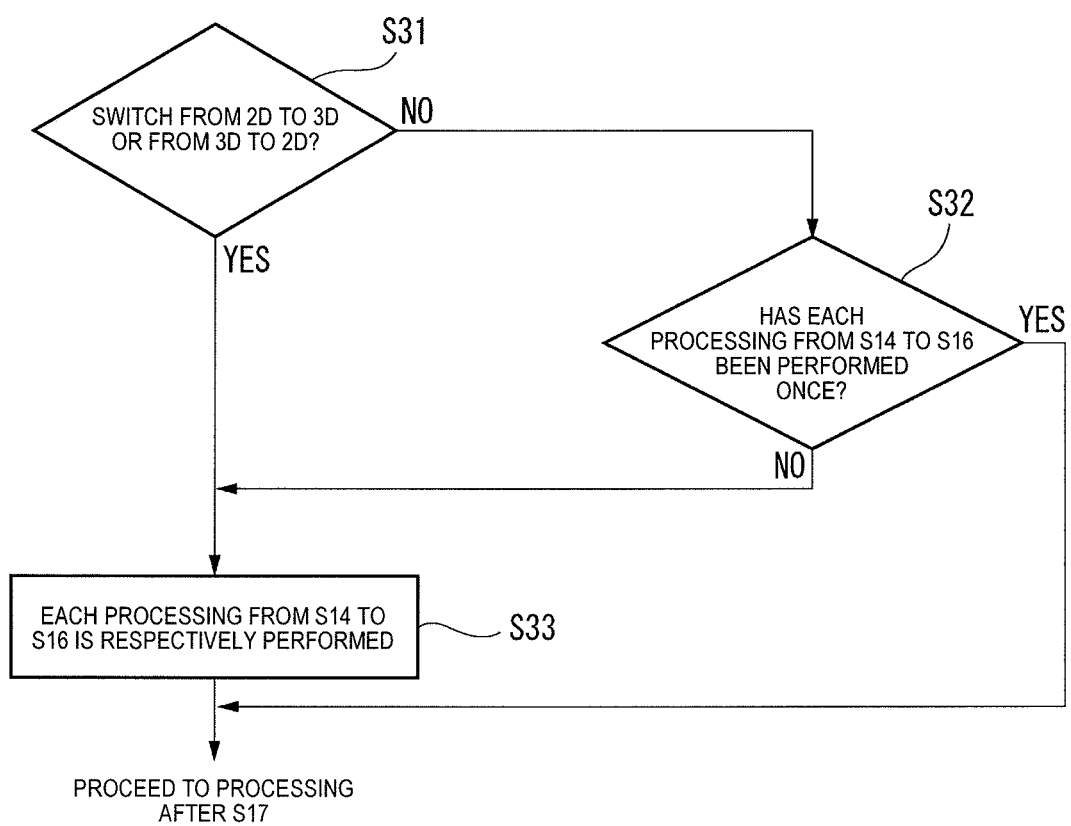
FIG. 13 is a flowchart for describing an operational procedure example at the time of interruption processing of mode switching.

FIG. 13 is a flowchart for describing an operational procedure example at the time of interruption processing of mode switching. The processing in FIG. 13 is started at the time when the processing of step S31 (that is, the processing of switching from the 2D mode to the 3D mode or from the 3D mode to the 2D mode) occurs interruptively.

In FIG. 13, CPU 262 of CCU 22 determines whether or not a switching signal for switching from the 2D mode to the 3D mode or from the 3D mode to the 2D mode has been acquired (S31). In a case where the switching signal has not been acquired (S31, NO), the current mode (for example, the 2D mode or the 3D mode) is maintained. CPU 262 determines whether or not the processing of steps S14 to S16 of FIG. 12 has been performed once (S32). In a case where the processing of steps S14 to S16 of FIG. 12 is performed once, CPU 262 holds information (flags and the like) having the effect in the internal memory (not illustrated) or the like, and can determine whether or not the processing of steps S14 to S16 in FIG. 12 has been performed once. In a case where it is determined that the processing of steps S14 to S16 of FIG. 12 has been performed once (S32, YES), the processing proceeds to the processing after step S17 of FIG. 12. This means that it is not necessary to change the photometric area since the current mode is not changed and the determination of the photometric area has already been completed and the processing of steps S14 to S16 is not necessary, and the processing of image processor 261A may be ended without proceeding to the processing after step S17 in FIG. 12.

Meanwhile, in a case where the switching signal has been acquired (S31, YES), or in a case where it is determined that the processing of steps S14 to S16 of FIG. 12 has never been performed (S32, NO), image processor 261A performs the processing of steps S14 to S16 illustrated in FIG. 12 (S33).

After step S33, the processing of image processor 261A proceeds to the processing following the step S17.

Next, in Embodiment 2, as an example of the signal processing performed with respect to the imaged video in order to improve the image quality of the video, an adjustment processing of white balance (WB) is exemplified, and an example in which, in a case of switching from the 2D mode to the 3D mode, an area used for deriving parameters (for example, WB adjustment value) of WB adjustment processing is determined, will be described.

Figure 14:
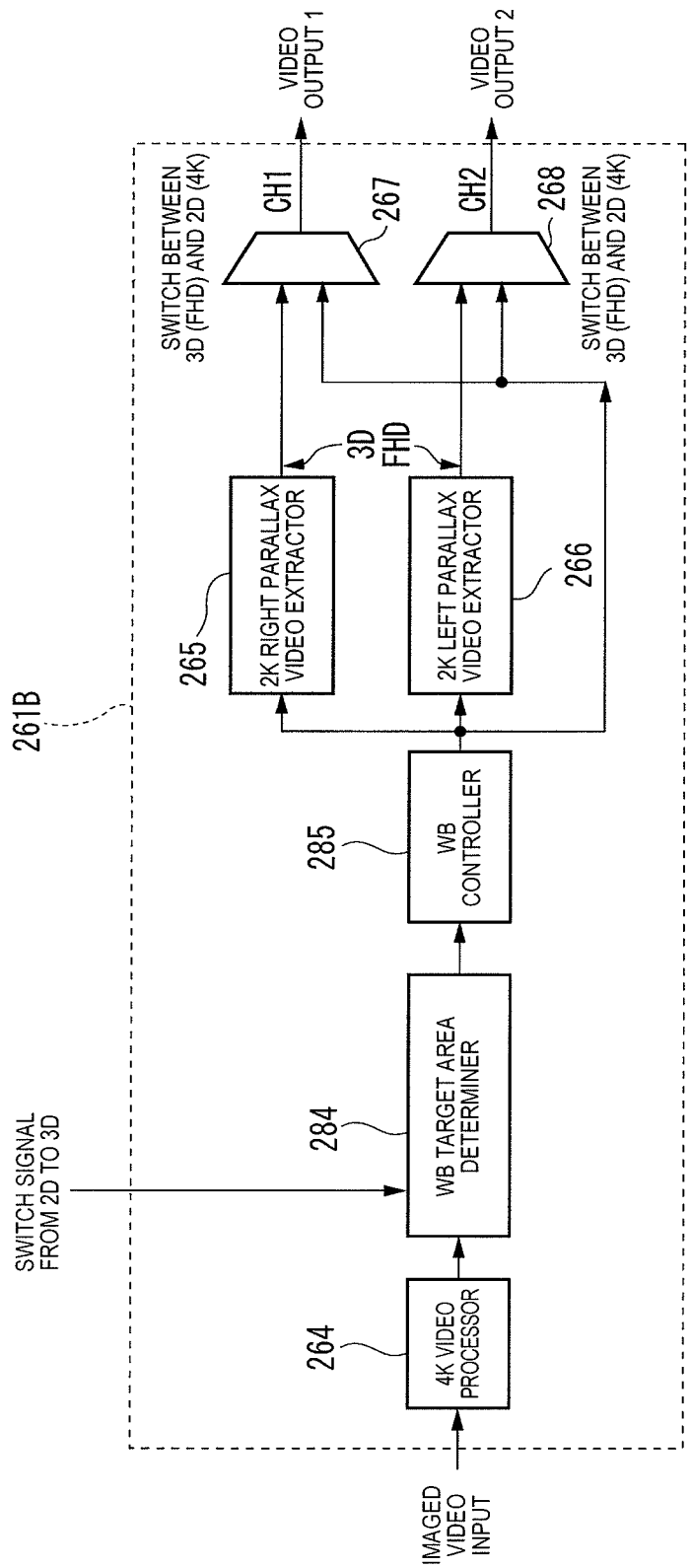
FIG. 14 is a block diagram illustrating a second example of the functional configuration of the image processor of the camera apparatus of Embodiment 2.

FIG. 14 is a block diagram illustrating a second example of a functional configuration of the image processor of camera apparatus 20 of Embodiment 2. Image processor 261B includes 4K video processor 264, WB target area determiner 284, WB controller 285, 2K left parallax video extractor 265, 2K right parallax video extractor 266, and video output switchers 267 and 268. In addition, although frame buffer FB1 (memory) is not illustrated and omitted in FIG. 14, when frame buffer FB1 is provided in CCU 22, frame buffer FB1 may be provided either on the inside or on the outside of image processor 261B. In addition, WB target area determiner 284 and WB controller 285 illustrated in FIG. 14 may be included being combined in image processor 261A illustrated in FIG. 10.

Since the internal configuration of image processor 261B in FIG. 14 includes the same internal configurations as each of those of the image processor 261A in FIG. 10, the same reference numerals are given to the same configurations and the description is simplified or omitted, and different contents will be described.

The video data of 4K pixels generated by 4K video processor 264 is input to WB target area determiner 284.

Figure 15:
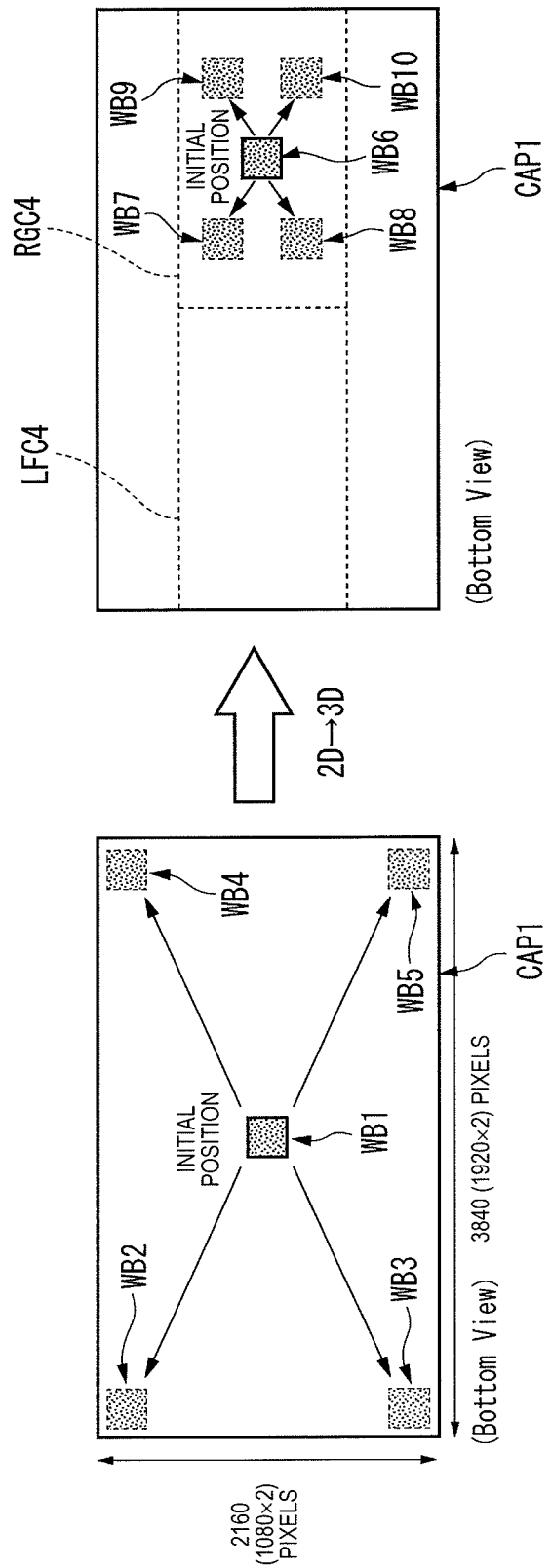
FIG. 15 is an explanatory view illustrating an adjustment example of a target area of WB with respect to the subject in accordance with switching from the 2D mode to the 3D mode.

In accordance with the switching signal from the 2D mode to the 3D mode, WB target area determiner 284 (one example of the determiner) determines an area used for deriving parameters (for example, WB adjustment value) of the signal processing (for example, WB adjustment processing) with respect to the left eye image and the right eye image (for example, video data of 4K pixels generated by 4K video processor 264) which are imaged by camera head 21 (refer to FIG. 15). In addition, in accordance with the switching signal from the 3D mode to the 2D mode, WB target area determiner 284 determines an area used for deriving parameters (for example, WB adjustment value) of the signal processing (for example, WB adjustment processing) with respect to the left eye image and the right eye image (for example, video data of 4K pixels generated by 4K video processor 264) which are imaged by camera head 21. In addition, even when the switching from the 2D mode to the 3D mode or the switching from the 3D mode to the 2D mode does not occur, WB target area determiner 284 determines an area used for deriving parameters (for example, WB adjustment value) of the signal processing (for example, WB adjustment processing) with respect to the left eye image and the right eye image (for example, video data of 4K pixels generated by 4K video processor 264) which are imaged by camera head 21.

FIG. 15 is an explanatory view illustrating an adjustment example of the target area of WB with respect to the subject in accordance with switching from the 2D mode to the 3D mode. In FIG. 15, the imaging surface CAP1 is the imaging surface of a so-called bottom view (that is, when the object side is viewed from the imaging surface side). In order to simplify the description of FIG. 15, extraction range LFC4 of the 2D left parallax video which configures the 3D video and extraction range RGC4 of the 2D right parallax video which configures the same 3D video, are set in a state where there is no shift in the vertical direction of imaging surface CAP1 and of being horizontally aligned in the horizontal direction. Extraction range LFC4 is the extraction range of the 2K left parallax video (left eye image). Similarly, extraction range RGC4 is the extraction range of the 2K right parallax video (right eye image).

On the left side of the page of FIG. 15, in the 2D mode, in imaging surface CAP1 (for example, the size of "2160 pixels×3840 pixels" that corresponds to 4K pixels) of the image sensor in camera head 21, as the area used for deriving the WB adjustment value, small area WB1 including the center of imaging surface CAP1 is illustrated as an initial position. In other words, based on the WB adjustment value in small area WB1, WB target area determiner 284 performs the WB adjustment processing with respect to the left eye image and the right eye image (for example, the video data of 4K pixels generated by 4K video processor 264) which are imaged by camera head 21. Similarly to Embodiment 1, WB target area determiner 284 may move and change the area used for deriving the WB adjustment value to any of other small areas WB2, WB3, WB4, and WB5 which have the same area as that of small area WB1 from small area WB1 in accordance with the operation of the user (for example, an observer, such as a doctor) who reads the 2D left parallax video and the 2D right parallax video which configure the 3D video projected to monitor 30.

Here, it is assumed that the operation (that is, the switching signal from the 2D mode to the 3D mode) of the user for switching from the 2D mode to the 3D mode is performed. In accordance with the operation, as illustrated on the right side of the page of FIG. 15, WB target area determiner 284 determines, for example, small area WB6 including the center of extraction range RGC4 of the 2K right parallax video which configures the 3D video, as the initial position of the area used for deriving parameters (for example, WB adjustment value) of the WB adjustment processing with respect to the video data of 4K pixels (that is, 2K left parallax video and 2K right parallax video) which are generated by 4K video processor 264. In addition, WB target area determiner 284 may determine, for example, the small area including the center of extraction range LFC4 of the 2K left parallax video which configures the 3D video as the area used for deriving the WB adjustment value. Similarly to Embodiment 1, WB target area determiner 284 may move and change the area used for deriving the WB adjustment value to any of other small areas WB7, WB8, WB9, and WB10 which have the same area as that of small area WB6 in extraction range RGC4 from small area WB6 in accordance with the operation of the user (for example, an observer, such as a doctor) who reads the 2D left parallax video and the 2D right parallax video which configure the 3D video projected to monitor 30.

In addition, WB target area determiner 284 (one example of the deriver) calculates the WB adjustment value in the area of the data of the 2D video of 4K pixels generated by 4K video processor 264 considering the area determined by WB target area determiner 284 as a target, and outputs the calculation result to WB controller 285.

By sampling the color of the area that corresponds to the calculation result of WB target area determiner 284, WB controller 285 (one example of the image processor) performs the WB adjustment processing with respect to the data of the 2D video of 4K pixels generated by 4K video processor 264. In addition, WB controller 285 may not be provided in image processor 261B, or may be provided in CPU 262. WB controller 285 outputs data of the 2D video of 4K pixels which is the processing result of the WB adjustment processing, to 2K right parallax video extractor 265 and 2K left parallax video extractor 266, respectively.

The flowchart illustrated in FIG. 12 can be similarly applied in a case where image processor 261B of CCU 22 is used. For example, instead of steps S14 to S16 in FIG. 12, processing of determining the parameter (WB adjustment value) of the WB adjustment processing, processing of adjusting the WB using the WB adjustment in the area determined based on the determination processing may be performed. Further, CCU 22 may have a configuration which is combined with image processors 261A and 261B, and in this case, between step S16 and step S17 in FIG. 12 or between step S13 and step S14, the processing of determining the parameter (WB adjustment value) of the WB adjustment processing and the WB adjustment processing in which the WB adjustment is used in the area determined based on the determination processing may be performed. Further, in a case where CCU 22 has a configuration which is combined with image processors 261A and 261B, the processing of steps S14 to S16, the processing of determining the parameter (WB adjustment value) of the WB adjustment processing, and the WB adjustment processing in which the WB adjustment is used in the area determined based on the determination processing may be performed.

Above, in the medical camera system of Embodiment 2, CCU 22 is connected to camera head 21 which can perform the imaging on the imaging surface of one screen of the 2K left parallax video (one example of the left eye image) and 2K right parallax video (one example of the right eye image) having parallax based on the light of the target site incident on surgical microscope 10 (one example of the optical instrument). In accordance with the switching from the 2D mode to the 3D mode, CCU 22 or camera apparatus 20 including CCU 22 derives (for example, calculates) the parameters (for example, brightness or light amount, and WB adjustment value) of the signal processing with respect to the left eye image and the right eye image which are imaged by camera head 21. In addition, based on the derived parameters (for example, brightness or light amount, and WB adjustment value), CCU 22 or camera apparatus 20 including CCU 22 performs the signal processing of the left eye image and the right eye image which are imaged by camera head 21, and outputs the left eye image and the right eye image to which the signal processing is performed to monitor 30.

Accordingly, when switching from the display of the 2D video to the display of the 3D video, CCU 22 or camera apparatus 20 including CCU 22 can adaptively adjust the area on the imaging surface used for deriving parameters of the signal processing for the imaged 3D video, and to image and output a high-definition 3D video with one camera. In other words, in the 3D mode, since the parameters of the signal processing are derived considering the extraction range of the 2K left parallax video or the 2K right parallax video which configures the 3D video as a target, it is possible to suppress deterioration of image quality of the 3D video due to the influence of the parameters of a part (for example, a peripheral portion of the imaging surface) of the imaging surface of the image sensor in the 2D mode which is not essentially required in the 3D mode. In addition, it is possible to image and output a high definition 3D video of 2K pixels with one camera head 21 and CCU 22, and to project the target site stereographically and with high definition. In particular, for surgical applications, clearer 3D video can be acquired, and operability at the time of surgery and visibility of the target site can be improved.

In addition, since one CCU 22 can cope with imaging output of 2D video of 4K pixels and imaging output of 3D video of 2K pixels, the disclosure can be applied to various observation video applications.

In addition, CCU 22 or camera apparatus 20 including CCU 22 determines an area used for deriving parameters of the signal processing from an imaging area of one of the left eye image and the right eye image which are imaged by camera head 21. Accordingly, CCU 22 or camera apparatus 20 including CCU 22 can appropriately determine the parameters when performing necessary signal processing with respect to the 2K left parallax video and the 2K right parallax video which configure the 3D video in the 3D mode, and can improve the image quality of the 3D video projected to monitor 30.

In addition, CCU 22 or camera apparatus 20 including CCU 22 determines an area used for deriving parameters of the signal processing based on the shape of the subject appearing in the left eye image and the right eye image which are imaged by camera head 21. Accordingly, since CCU 22 or camera apparatus 20 including CCU 22 can generate the 2K left parallax video and 2K right parallax video having high image quality that conforms to the shape of the subject imaged in the 3D mode, it is possible to appropriately improve the image quality of the 3D video projected to monitor 30.

In addition, the parameters for the signal processing is the exposure amount of at least one of the left eye image and the right eye image of the area used for deriving the parameters of the signal processing. CCU 22 or camera apparatus 20 including CCU 22 adjusts brightness of the left eye image and the right eye image which are imaged by camera head 21 based on the exposure amount. Accordingly, in the 3D mode, CCU 22 or camera apparatus 20 including CCU 22 can suppress deterioration of the image quality of the 3D video without becoming excessively dark or excessively bright due to the influence of the exposure amount of a part (for example, the peripheral portion of the imaging surface) of the imaging surface of the image sensor in the 2D mode which is not essentially required in the 3D mode.

In addition, the parameters for the signal processing is the white balance adjustment value of at least one of the left eye image and the right eye image of the area used for deriving the parameters of the signal processing. CCU 22 or camera apparatus 20 including CCU 22 adjusts white balance of the left eye image and the right eye image which are imaged by camera head 21 based on the white balance adjustment value. Accordingly, in CCU 22 or camera apparatus 20 including CCU 22, in the 3D mode, the 3D video of which the white balance is appropriately adjusted is obtained without becoming excessively bluish white or excessively reddish white due to the influence of the WB adjustment value of a part (for example, an external peripheral portion of imaging surface CAP1) of the imaging surface of the image sensor in the 2D mode which is not essentially required in the 3D mode.

Further, in the 3D mode, CCU 22 or camera apparatus 20 including CCU 22 includes distance measuring circuit 291 (one example of distance measurer) which measures distance L (refer to FIG. 19) from surgical endoscope 110 (one example of optical instrument) to an observation target site based on the parallax Δ (refer to FIG. 23) appearing in the left eye image and the right eye image which are imaged by camera head 21. CCU 22 or camera apparatus 20 outputs the result measured by distance measuring circuit 291 (that is, information on the distance) to monitor 130 (refer to FIG. 19) together with the left eye image and the right eye image to which the signal processing is performed. Accordingly, the user (for example, an observer, such as a doctor) can visually grasp the situation of the observation target site projected to monitor 130, can grasp the specific distance information from surgical endoscope 110 (refer to FIG. 19) to the observation target site, and can support the guidance of the next medical practice by the user at the time of surgery or examination.

In addition, in response to the switching from the 3D mode to the 2D mode, CCU 22 or camera apparatus 20 including CCU 22 interrupts the output of the information on the distance to monitor 130. Accordingly, in the 2D mode, neither the left and right 2K left parallax video having parallax nor the 2K right parallax video is input to distance measuring circuit 291, and thus, the information on the distance is not displayed on monitor 130. Therefore, the user (for example, an observer, such as a doctor) can easily recognize that the present is the 2D mode by the fact that the information on the distance is not displayed on monitor 130, and on the other hand, the user can easily recognize that the present is the 3D mode by the fact that the information on the distance is displayed on monitor 130.

(Background of Contents of Embodiment 3)

In the above-described medical camera system, in order to ensure a clear field of view of a target site at which surgery or treatment is performed, a display video with high definition and excellent visibility is desired. In addition, since the size or state of an observation target can be grasped more accurately and easily by stereoscopic viewing of a target site, there is an increasing demand for a 3D video that provides a stereoscopic observed video to the observer. Particularly, in a surgical application of a fine site, a high-definition 3D video is required, but in the related art, such as PTL 1, there was a problem that it is difficult to visually recognize the details of the observed video clearly. In addition, in order to generate a high-definition 3D video required in the medical field, it is necessary to use two different cameras for imaging an image for a left eye (left eye image) and an image for a right eye (right eye image) which have parallax.

Further, for example, in the medical camera system, when a display mode is switched such that the 2D video is displayed from a state where the 3D video is displayed, it is required that the display of video is smoothly switched such that a doctor or the like continuously grasps the details of the situation of the target site (for example, an affected part of a human body). However, in reality, due to factors, such as the following, delay time (that is, non-display time of the video) in units of several seconds occurs when switching from the display of the 3D video to the display of the 2D video, and there was a case where it is difficult to grasp the details of the situation of the target site (for example, the affected part of the human body) for a certain period of time or more. Specifically, in order to switch from the 3D mode of the video to the 2D mode, an operation for changing the display mode on the monitor side from the 3D mode to the 2D mode was necessary. Since the operation is usually performed by a person, it takes a certain period of time, and in accordance with the transmission format of the 3D video, for example, a delay time (that is, non-display time of the video) in units of several seconds has occurred. Therefore, there was a case where it is difficult to grasp the details of the situation of the target site (for example, the affected part of the human body) for a certain period of time or more, and the convenience of the user (for example, an observer, such as a doctor) is impaired. Factors to switch from the display of the 3D video to the display of the 2D image are, for example, that the eyes become tired when viewing the 3D video all the time during surgery or examination, that the details of the affected part that can be sufficiently grasped by the 2D video without the 3D video during surgery or examination is desired to be seen, and that it is desired to change the setting to 2D rather than 3D after surgery or examination. Even with the related art as in PTL 1, in a case of switching from the display of the 3D video to the display of the 2D video, it is still necessary to change the display mode on the monitor side from the 3D mode to the 2D mode, and there is no consideration for technical measures against the problem of impairing the convenience of the user (for example, an observer, such as a doctor) described above.

Here, in Embodiment 3 described below, in view of the above-described situation of the related art, an example of the image processing apparatus, the camera apparatus, and the output control method for suppressing the deterioration of the convenience of the user generated in accordance with the switching from the display of the 3D video to the display of the 2D video and the switching of the display mode of the video in a state of maintaining the display mode of the 3D video without changing the display mode on the monitor side from the 3D mode to the 2D mode, will be described.

Embodiment 3

Since the internal configuration of each of the medical camera system and the camera apparatus or the CCU of Embodiment 3 is the same as the internal configuration of each of the medical camera system and camera apparatus 20 or CCU 22 of Embodiment 1, the same configuration will be given the same reference numerals and the description thereof will be simplified or omitted, and different contents will be described.

Figure 16:
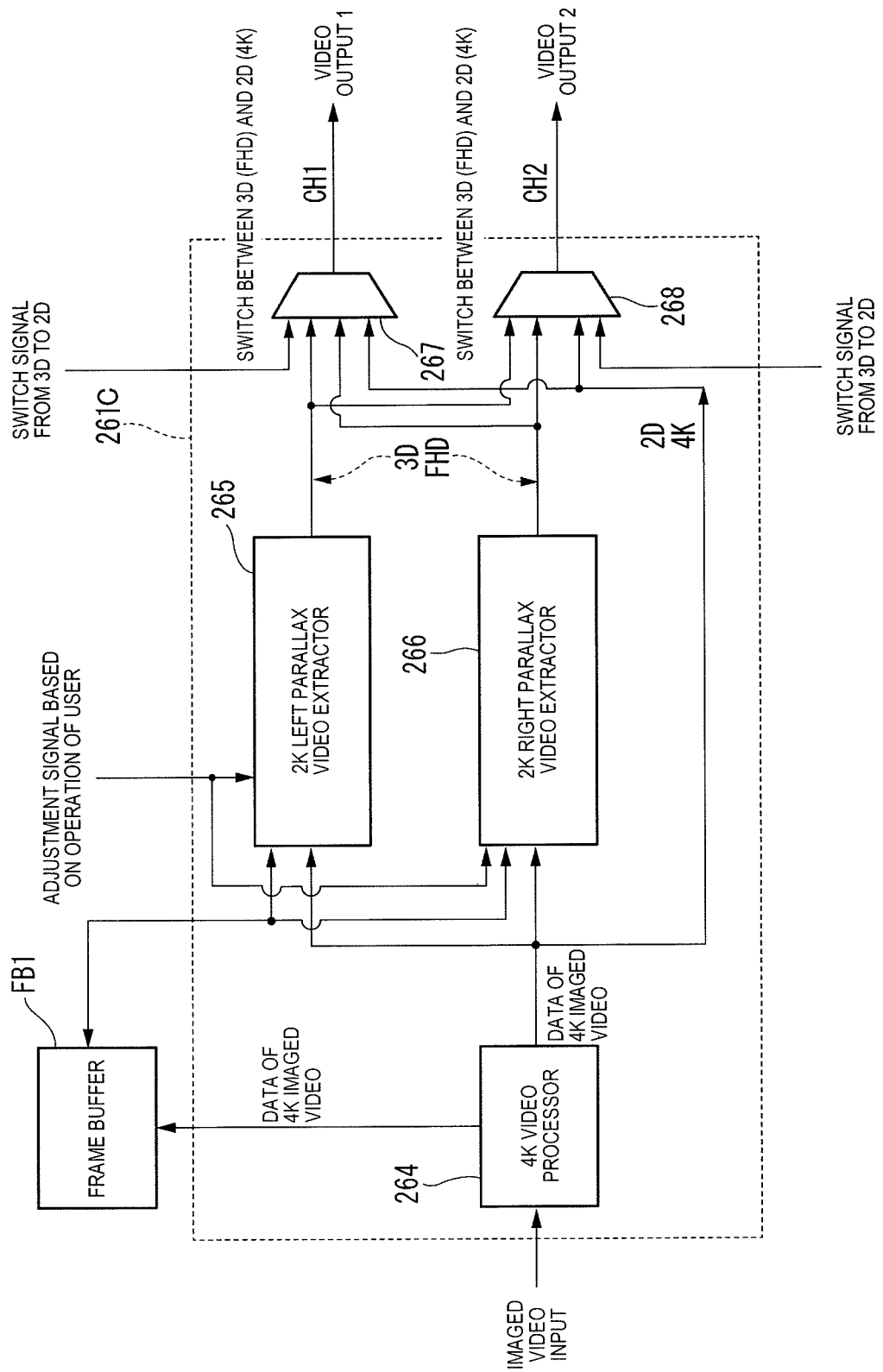
FIG. 16 is a block diagram illustrating a functional configuration example of an image processor of a camera apparatus of Embodiment 3.

FIG. 16 is a block diagram illustrating a functional configuration example of image processor 261C of camera apparatus 20 of Embodiment 3. Image processor 261C includes 4K video processor 264, 2K left parallax video extractor 265, 2K right parallax video extractor 266, and video output switchers 267 and 268. In addition, when frame buffer FB1 (memory) is provided in CCU 22, frame buffer FB1 (memory) may be provided either on the inside or on the outside of image processor 261.

Since the internal configuration of image processor 261C in FIG. 16 includes the same internal configurations as each of those of image processor 261 in FIG. 6, the same reference numerals are given to the same configurations and the description is simplified or omitted, and different contents will be described.

Data of the 2K left parallax video generated by 2K left parallax video extractor 265 is input to both of video output switchers 267 and 268. In addition, data of the 2K right parallax video generated by 2K right parallax video extractor 266 is input to both of video output switchers 267 and 268.

Here, as described above, when the display mode is switched such that the 2D video is displayed from the state where the 3D image is displayed, it is required that the display of video is smoothly switched such that the user (for example, an observer, such as a doctor) continuously grasps the details of the situation of the target site (for example, an affected part of a human body). However, in reality, delay time (that is, non-display time of the video) in units of several seconds occurs when switching from the display of the 3D video to the display of the 2D video, and there was a case where it is difficult to grasp the details of the situation of the target site (for example, the affected part of the human body) for a certain period of time or more. Specifically, in order to switch from the 3D mode of the video to the 2D mode, an operation for changing the display mode on the monitor side from the 3D mode to the 2D mode was necessary. Since the operation is usually performed by a person, it takes a certain period of time, and in accordance with the transmission format of the 3D video (for example, HDMI (registered trademark) or SDI), for example, a delay time (that is, non-display time of the video) in units of several seconds has occurred. Therefore, there was a case where it is difficult to grasp the details of the situation of the target site (for example, the affected part of the human body) for a certain period of time or more, and the convenience of the user (for example, an observer, such as a doctor) is impaired. Therefore, as a result of the temporary interruption of the display of the video by the user (for example, an observer, such as a doctor) during surgery or examination, there is a time zone in which the state of the affected part cannot be grasped, and since it was necessary to perform the operation of changing the display mode of the monitor, usability is not excellent.

Here, in Embodiment 3, for example, when switching from the 3D mode to the 2D mode, image processor 261C of CCU 22 does not change and maintains the transmission format at the time of transmitting (outputting) the 3D video to monitor 30, and changes the data of the transmission target from the 2K left parallax video and the 2K right parallax video which configure the 3D video to only one of the 2K left parallax video and the 2K right parallax video that become the 2D video. Accordingly, since there is no need to change the transmission format, it is unnecessary to change the display mode on monitor 30 side from the 3D mode to the 2D mode, and in a state where the display mode on monitor 30 side is maintained in the 3D mode, a pseudo 2D video can be displayed. Therefore, a problem that it becomes impossible to grasp the details of the situation of the target site (for example, the affected part of the human body) for a certain period of time or more, which occurred in accordance with the switching of the display mode of the video, is eliminated, and the above-described usability of the user (for example, an observer, such as a doctor) is improved.

Video output switcher 267 (one example of the output controller) switches the video signal output and outputs the 2D left parallax video of 2K pixels from the 2K left parallax video extractor 265, the 2D right parallax video of 2K pixels from the 2K right parallax video extractor 266, or the video signal of the 2D video of 4K pixels from 4K video processor 264 via channel CH1 (one example of the first channel). In a case of switching from the 2D mode to the 3D mode, the video output switcher 267 outputs the 2D left parallax video of 2K pixels from the 2K left parallax video extractor 265. In a case of switching from the 3D mode to the 2D mode, video output switcher 267 outputs the 2D left parallax video of 2K pixels from the 2K left parallax video extractor 265 or the 2D right parallax video of 2K pixels from 2K right parallax video extractor 266. In addition, in the output mode of the 2D video of 4K pixels, video output switcher 267 outputs the video signal of the 2D video of 4K pixels from 4K video processor 264.

Video output switcher 268 (one example of the output controller) switches the video signal output and outputs the 2D left parallax video of 2K pixels from the 2K left parallax video extractor 265, the 2D right parallax video of 2K pixels from the 2K right parallax video extractor 266, or the video signal of the 2D video of 4K pixels from 4K video processor 264 via channel CH2 (one example of the second channel).

In a case of switching from the 2D mode to the 3D mode, the video output switcher 268 outputs the 2D right parallax video of 2K pixels from the 2K right parallax video extractor 266. In a case of switching from the 3D mode to the 2D mode, video output switcher 268 outputs the 2D left parallax video of 2K pixels from the 2K left parallax video extractor 265 or the 2D right parallax video of 2K pixels from 2K right parallax video extractor 266. In addition, in the output mode of the 2D video of 4K pixels, video output switcher 268 outputs the video signal of the 2D video of 4K pixels from 4K video processor 264.

In addition, in a case of outputting the 2D video of 4K pixels in the output mode of the 2D video of 4K pixels, the video signal may be output to both of video output 1 of channel CH1 and video output 2 of channel CH2, or the video signal may be output to only one of video output 1 and video output 2. Further, the 2D video of 4K pixels may be output to either one of channel CH1 and channel CH2, and 2D video of 2K pixels may be output to the other.

Figure 17A:
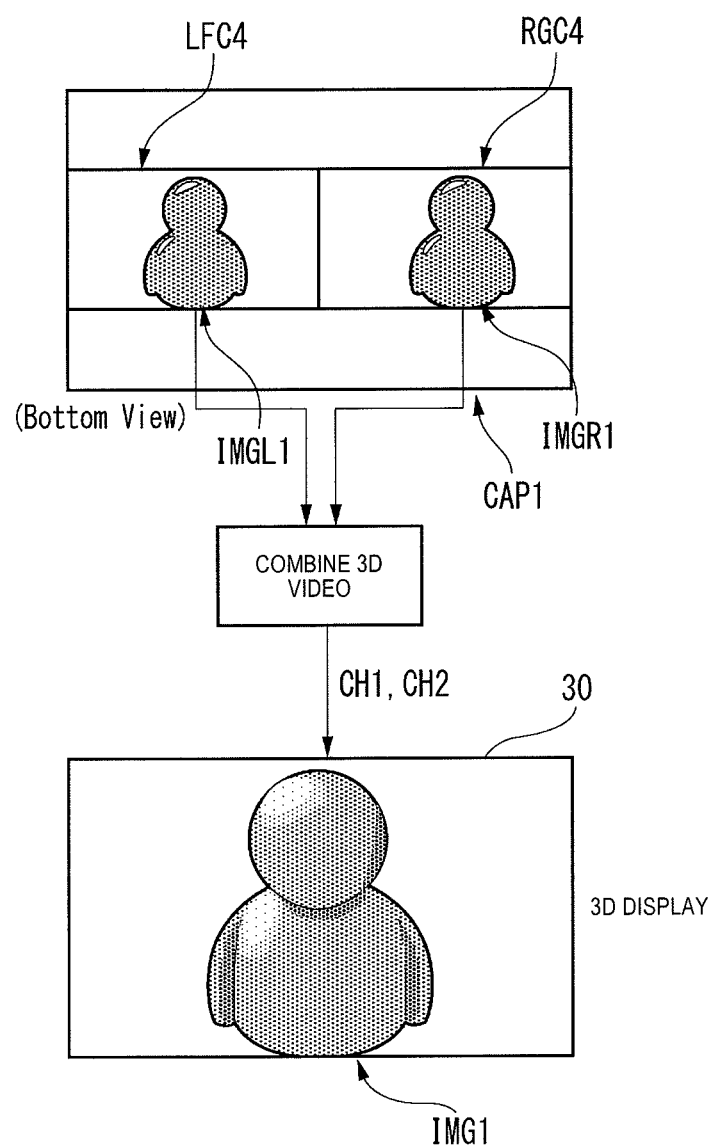
FIG. 17A is an explanatory view illustrating a transmission example of the left eye image and the right eye image in the 3D mode.
Figure 17B:
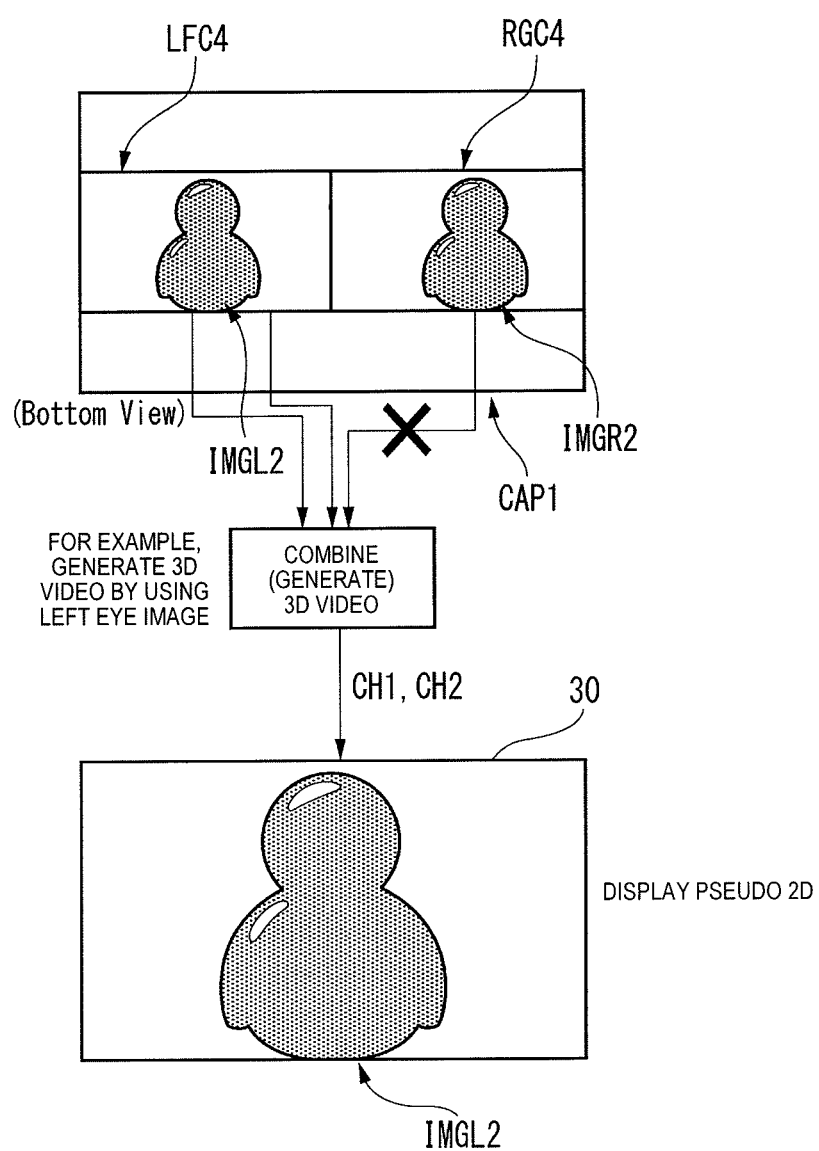
FIG. 17B is an explanatory view illustrating a transmission example of the left eye image and the right eye image after switching from the 3D mode to the 2D mode.

FIG. 17A is an explanatory view illustrating a transmission example of the left eye image and the right eye image in the 3D mode. FIG. 17B is an explanatory view illustrating a transmission example of the left eye image and the right eye image after switching from the 3D mode to the 2D mode. In FIGS. 17A and 17B, imaging surface CAP1 is an imaging surface of a so-called bottom view (that is, when the object side is viewed from the imaging surface side).

In FIG. 17A, image processor 261C of CCU 22 outputs 2K left parallax video IMGL1 of extraction range LFC4 imaged on imaging surface CAP1 of the image sensor (capture 213) of camera head 21 to monitor 30 via channel CH1. In addition, image processor 261C of CCU 22 outputs 2K right parallax video IMGR1 of extraction range RGC4 imaged on imaging surface CAP1 of the image sensor (capture 213) of camera head 21 to monitor 30 via channel CH2. Accordingly, when 2K left parallax video IMGL1 and 2K right parallax video IMGR1 are projected to monitor 30, the videos are combined with each other and displayed as 3D video IMG1.

Meanwhile, in FIG. 17B, when switching from the 3D mode to the 2D mode, image processor 261C of CCU 22 outputs 2K left parallax video IMGL2 of extraction range LFC4 imaged on imaging surface CAP1 of the image sensor (capture 213) of camera head 21 to monitor 30 via both of channel CH1 and channel CH2. Accordingly, both of 2K left parallax video IMGL2 and 2K right parallax video IMGR2 having parallax on the left and right sides are not output to monitor 30, and only one (in this case, 2K left parallax video IMGL2) is projected to monitor 30, and thus, 2D video IMG2 is displayed in a pseudo manner while the transmission format of the 3D video is not changed. In addition, in FIG. 17B, an example in which 2K left parallax video IMGL2 is output to monitor 30 via both of channel CH1 and channel CH2 has been described, but it is needless to say that 2K right parallax video IMGR2 may be output to monitor 30 via both of channel CH1 and channel CH2.

Figure 18:
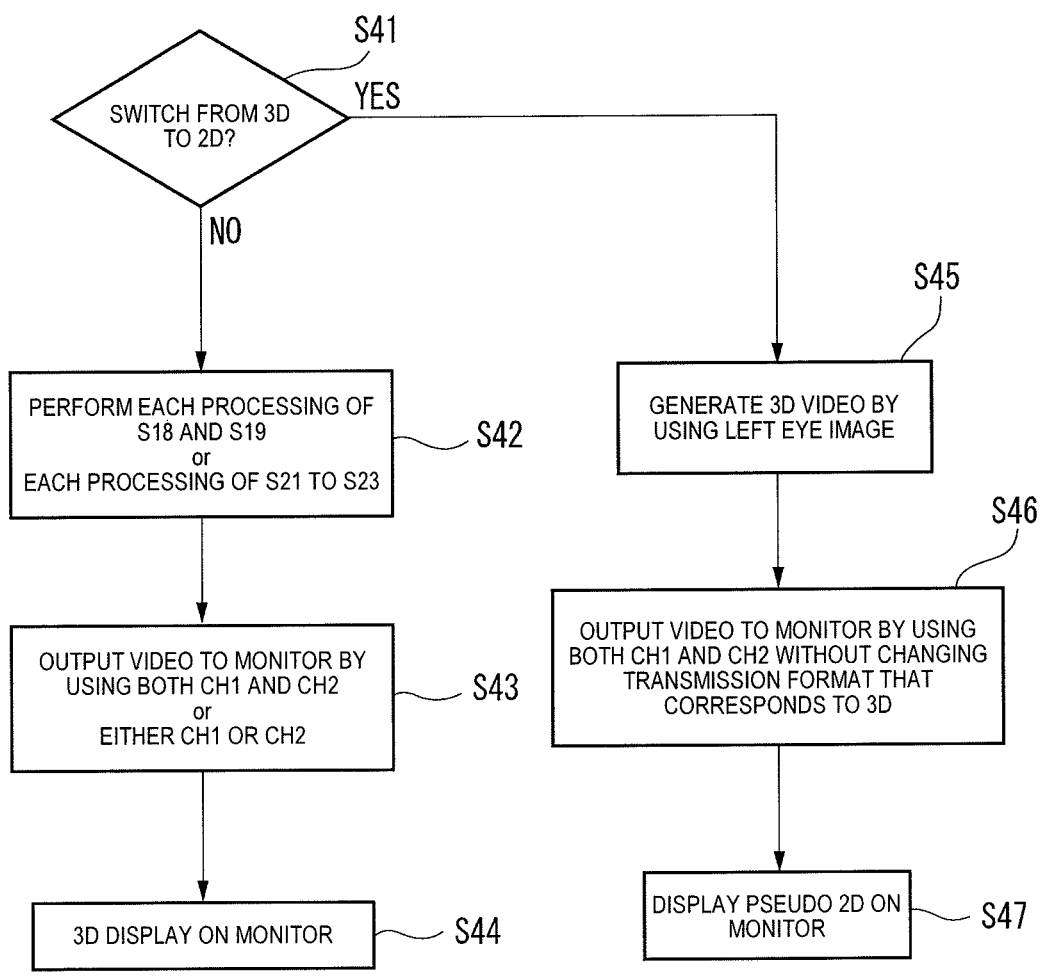
FIG. 18 is a flowchart for describing an operational procedure example of the camera apparatus of Embodiment 3.

FIG. 18 is a flowchart for describing an operational procedure example of camera apparatus 20 of Embodiment 3. The processing in FIG. 18 is started at the time when the processing of step S41 (that is, the processing of switching from the 3D mode to the 2D mode) occurs interruptively.

In FIG. 18, CPU 262 of CCU 22 determines whether or not the switching signal from the 3D mode to the 2D mode has been acquired (S41). In a case where the switching signal has not been acquired (S41, NO), the current mode (for example, the 3D mode) is maintained. In response to the signal that notifies the current mode from CPU 262, image processor 261C performs each processing of steps S18 and S19 of FIG. 12 or each processing of steps S21 to S23 (S42).

Image processor 261C outputs the 2K left parallax video from channel CH1 and outputs the 2K right parallax video from channel CH2 or outputs the 3D video combined in step S22 from either channel CH1 or channel CH2 or from both of channel CH1 and channel CH2 (S43). In step S43, the video output via each of the channels is projected to monitor 30 (S44), and the 3D video is read by the user (for example, an observer, such as a doctor).

Meanwhile, in a case where the switching signal has been acquired (S41, YES), by using, for example, the 2K left parallax video (one example of the left eye image), image processor 261C generates the data (specifically, two 2K left parallax videos) of the 3D video that conforms to the 3D transmission format and be transmitted (S45). Without changing the 3D transmission format, image processor 261C outputs the data of the 3D video generated in step S45 to monitor 30 by using both of channel CH1 and channel CH2 (S46). In step S46, the video output via each of the channels is projected to monitor 30 (S47), and the 3D video that conforms to the 3D transmission format and is sent is read by the user as a pseudo 2D video (for example, an observer, such as a doctor).

Above, in the medical camera system of Embodiment 3, CCU 22 is connected to camera head 21 which can perform the imaging on the imaging surface of one screen of the 2K left parallax video (one example of the left eye image) and 2K right parallax video (one example of the right eye image) having parallax based on the light of the target site incident on surgical microscope 10 (one example of the optical instrument). In addition, CCU 22 or camera apparatus 20 including CCU 22 performs the signal processing of the left eye image and the right eye image which are imaged by camera head 21, and outputs the left eye image and the right eye image to which the signal processing is performed to monitor 30 via each of channel CH1 (one example of the first channel) and channel CH2 (one example of the second channel). In addition, in response to the switching from the 3D mode to the 2D mode, CCU 22 or camera apparatus 20 including CCU 22 outputs one of the left eye image and the right eye image to which the signal processing is performed to monitor 30 via each of channel CH1 and channel CH2.

Accordingly, when changing from the display of the 3D video to the display of the 2D video, CCU 22 or camera apparatus 20 including CCU 22 does not change and maintains the transmission format of the 3D video, and transmits at least one of the 2K left parallax video and 2K left parallax video which configures the 3D video to monitor 30. In other words, since there is no need to change the transmission format, it is unnecessary to perform an operation of changing the display mode on monitor 30 side from the 3D mode to the 2D mode, and in a state where the display mode on monitor 30 side is maintained in the 3D mode, a pseudo 2D video can be displayed. Therefore, CCU 22 or camera apparatus 20 including CCU 22 can eliminate a problem that it becomes impossible to grasp the details of the situation of the target site (for example, the affected part of the human body) for a certain period of time or more, which occurred in accordance with the switching of the display mode of the video, and the above-described usability of the user (for example, an observer, such as a doctor) is improved. In addition, it is possible to image and output a high definition 3D video of 2K pixels with one camera head 21 and CCU 22, and to project the target site stereographically and with high definition.

In addition, since one CCU 22 can cope with imaging output of 2D video of 4K pixels and imaging output of 3D video of 2K pixels, the disclosure can be applied to various observation video applications.

Further, CCU 22 or camera apparatus 20 including CCU 22 displays the 2D video on monitor 30 in a pseudo manner in the 2D mode based on one of the left eye image and the right eye image output to monitor 30 via both of channel CH1 and channel CH2. Accordingly, only by displaying any one of the 2K left parallax video or the 2K right parallax video on monitor 30, CCU 22 or camera apparatus 20 including CCU 22 can suppress the generation of display delay time that is supposed to be generated when switching from the 3D mode to the 2D mode as much as possible, and can simply display the 2D video in the 2D mode.

In addition, the switching from the 3D mode to the 2D mode is input by the operation of the user. Accordingly, CCU 22 or camera apparatus 20 including CCU 22 can easily detect the switching from the 3D mode to the 2D mode by a simple operation of the user.

Further, in the 3D mode, CCU 22 or camera apparatus 20 including CCU 22 includes distance measuring circuit 291 (one example of distance measurer) which measures distance L (refer to FIG. 19) from surgical endoscope 110 (one example of optical instrument) to an observation target site based on the parallax Δ (refer to FIG. 23) appearing in the left eye image and the right eye image which are imaged by camera head 21. CCU 22 or camera apparatus 20 outputs the result measured by distance measuring circuit 291 (that is, information on the distance) to monitor 130 (refer to FIG. 19) together with the left eye image and the right eye image to which the signal processing is performed. Accordingly, the user (for example, an observer, such as a doctor) can visually grasp the situation of the observation target site projected to monitor 130, can grasp the specific distance information from surgical endoscope 110 (refer to FIG. 19) to the observation target site, and can support the guidance of the next medical practice by the user at the time of surgery or examination.

In addition, in response to the switching from the 3D mode to the 2D mode, CCU 22 or camera apparatus 20 including CCU 22 interrupts the output of the information on the distance to monitor 130. Accordingly, in the 2D mode, neither the left and right 2K left parallax video having parallax nor the 2K right parallax video is input to distance measuring circuit 291, and thus, the information on the distance is not displayed on monitor 130. Therefore, the user (for example, an observer, such as a doctor) can easily recognize that the present is the 2D mode by the fact that the information on the distance is not displayed on monitor 130, and on the other hand, the user can easily recognize that the present is the 3D mode by the fact that the information on the distance is displayed on monitor 130.

In addition, in the above-described embodiment, surgical microscope 10 is exemplified as an example of the optical instrument, but surgical endoscope 110 may be applied. Next, a configuration of the surgical endoscope system to which operation endoscope 110 is applied will be described as an example of an optical instrument with reference to FIGS. 19 and 20.

Figure 19:
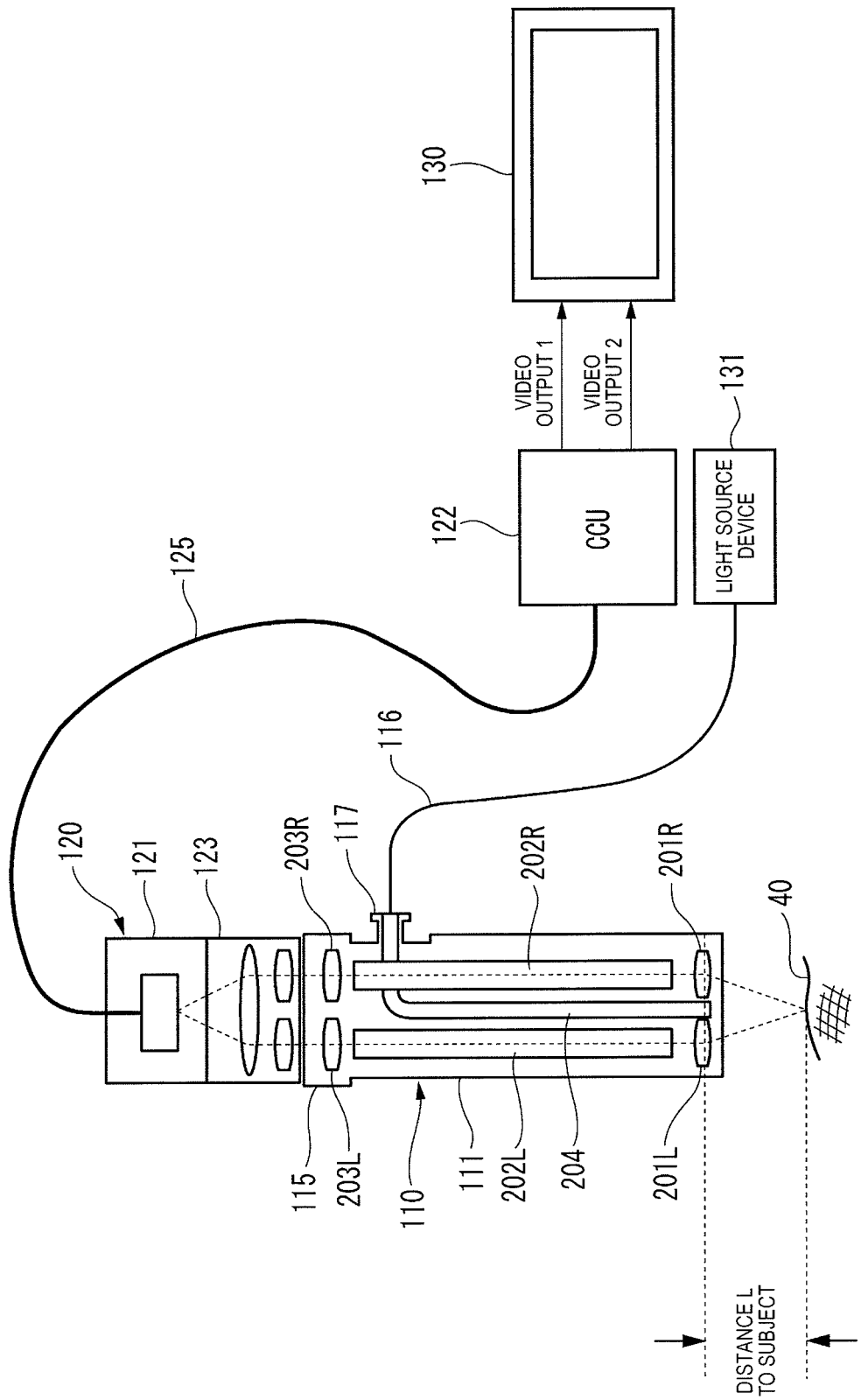
FIG. 19 is a system configuration view illustrating a configuration example in which the medical camera system including the camera apparatus of each of the embodiments is applied to a surgical endoscope system.

FIG. 19 is a system configuration view illustrating a configuration example in which the medical camera system including the camera apparatus of each of the embodiments is applied to the surgical endoscope system. The surgical endoscope system includes surgical endoscope 110, camera apparatus 120, monitor 130, and light source device 131. Camera apparatus 120 is similar to camera apparatus 20 illustrated in FIGS. 1 to 5, and is configured to include camera head 121 and CCU 122.

Surgical endoscope 110 is a stereoscopic endoscope, and includes objective lenses 201 R and 201 L, relay lenses 202R and 202L, and imaging lenses 203R and 203L, as an observation optical system provided in elongated insertion portion 111 so as to correspond to the left and right eyes of the observer. Surgical endoscope 110 includes camera installer 115 provided on the proximal side of the observation optical system and light source installer 117, and is provided with light guide 204 that guides the illumination light from light source installer 117 to the distal end portion of insertion portion 111. By installing imaging lens portion 123 of camera head 121 to camera installer 115 and performing the imaging, it is possible to acquire an observation video for stereoscopic vision in camera apparatus 120. Light guide cable 116 is connected to light source installer 117, and light source device 131 is connected via light guide cable 116.

Camera head 121 and CCU 122 are connected to each other by signal cable 125, and video signal for the 3D video of the subject imaged by camera head 121 is transmitted to CCU 122 via signal cable 125. Monitor 130 is connected to the output terminal of CCU 122, and two left and right video outputs 1 and 2 for the 3D display are output. On monitor 130, the 3D video of 2K pixels is displayed as an observation video of the target site.

Figure 20:
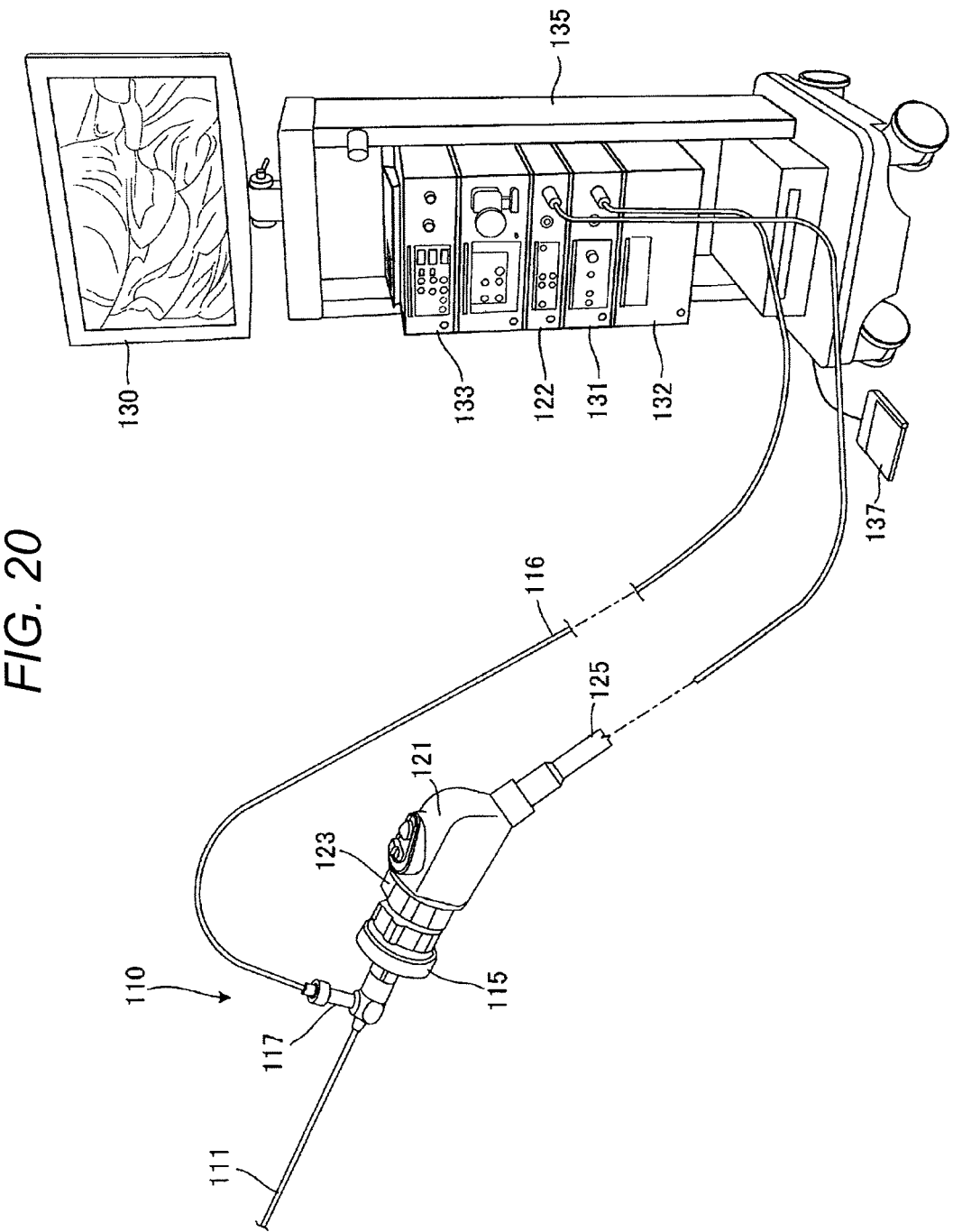
FIG. 20 is a view illustrating an external appearance example of the surgical endoscope system of each of the embodiments.

FIG. 20 is a view illustrating an external appearance example of the surgical endoscope system of each of the embodiments. In surgical endoscope 110, camera installer 115 is provided on the proximal side of insertion portion 111, and imaging lens portion 123 of camera head 121 is installed. Light source installer 117 is provided on the proximal side portion of insertion portion 111, and light guide cable 116 is connected thereto. An operation switch is provided in camera head 121, and it is possible to perform an operation (freeze, release, image scan, and the like) of the observed video to be imaged at the hand of the user. The surgical endoscope system includes recorder 132 for recording the observed video imaged by camera apparatus 120, operation unit 133 for operating the surgical endoscope system, and foot switch 137 for performing the operation input by the foot of the observer, and operation unit 133, CCU 122, light source device 131, and recorder 132 are stored in control unit housing 135. Monitor 130 is disposed above control unit housing 135.

In this manner, in the configuration of the surgical endoscope system illustrated in FIGS. 19 and 20, similar to the configuration of the above-described medical camera system, from the left and right parallax images of the target site acquired by surgical endoscope 110, it is possible to generate and output each of the left parallax video and the right parallax video of 2K pixels, and to display the 3D video of 2K pixels on monitor 130.

Embodiment 4

In Embodiment 4, an example of the surgical endoscope system which is capable of measuring distance L from the optical instrument (for example, the distal end of the insertion portion of surgical endoscope 110 illustrated in FIG. 19) to the observation target site (that is, subject 40) and displaying the distance measurement result on monitor 130, in the 3D mode, will be described. Since the configuration of the surgical endoscope system has been described with reference to FIGS. 19 and 20, the description of the same contents will be simplified or omitted, and different contents will be described.

FIG. 21 is a block diagram illustrating a functional configuration example of image processor 271 of camera apparatus 20 of Embodiment 4. Similar to image processor 261 illustrated in FIG. 6, image processor 271 includes 4K video processor 264, 2K left parallax video extractor 265, and 2K right parallax video extractor 266, and includes 3D video combiner 272, distance measuring circuit 291, video output switchers 273 and 274, display element generator 292, and superimposition controllers 293 and 294.

In response to the switching signal from the 2D mode to the 3D mode, 2K left parallax video extractor 265 outputs the 2K left parallax video which configures the 3D video to 3D video combiner 272, video output switcher 273, and distance measuring circuit 291, respectively. In response to the switching signal from the 3D mode to the 2D mode, the 2K left parallax video extractor 265 interrupts the output of at least the 2K left parallax video which configures the 3D video to distance measuring circuit 291.

In response to the switching signal from the 2D mode to the 3D mode, 2K right parallax video extractor 266 outputs the 2K right parallax video which configures the 3D video to 3D video combiner 272, video output switcher 274, and distance measuring circuit 291, respectively. In response to the switching signal from the 3D mode to the 2D mode, the 2K right parallax video extractor 266 interrupts the output of at least the 2K right parallax video which configures the 3D video to distance measuring circuit 291.

3D image combiner 272 performs combining processing of the 3D left parallax video from the output of 2K left parallax video extractor 265 and the 3D right parallax video from the output of 2K right parallax video extractor 266, and generates the 3D video of HD resolution (3D (normal)). The combining processing of the 3D video can be performed by using video conversion processing (3D visualization processing) that corresponds to various transmission methods of the 3D video, such as a side-by-side method in which the left parallax video and the right parallax video are adjacent to each other in the horizontal direction, or a line by line method in which the left parallax video and the right parallax video are disposed for each line.

The video output switchers 273 and 274 switch the output of the video signal, and outputs the video signal of the 3D video (3D (FHD)) of 2K pixels, the 3D video of HD resolution (3D (normal)), or the 2D video of 4K pixels (2D (4K)). In a case of outputting the 3D video (3D (FHD)) of 2K pixels, the video signal of the 3D left parallax video is output as video output 1 of channel CH1 and the video signal of the 3D right parallax video is output as video output 2 of channel CH2. In a case of outputting the 2D video (2D (4K)) of 4K pixels or the 3D video (3D (normal)) of HD resolution, the video signal may be output to both of video output 1 of channel CH1 and video output 2 of channel CH2, or the video signal may be output to only one of video output 1 of channel CH1 and video output 2 of channel CH2.

In the 3D mode, distance measuring circuit 291 (one example of the distance measurer) measures distance L (refer to FIG. 19) from surgical endoscope 110 to the observation target site based on the parallax $\Delta$ (refer to FIG. 23) appearing in the 2K left parallax video from 2K left parallax video extractor 265 and the 2K right parallax video from 2K right parallax video extractor 266. Distance measuring circuit 291 outputs the measurement result (that is, information on distance L from surgical endoscope 110 to the observation target site) to CPU 262.

Figure 22:
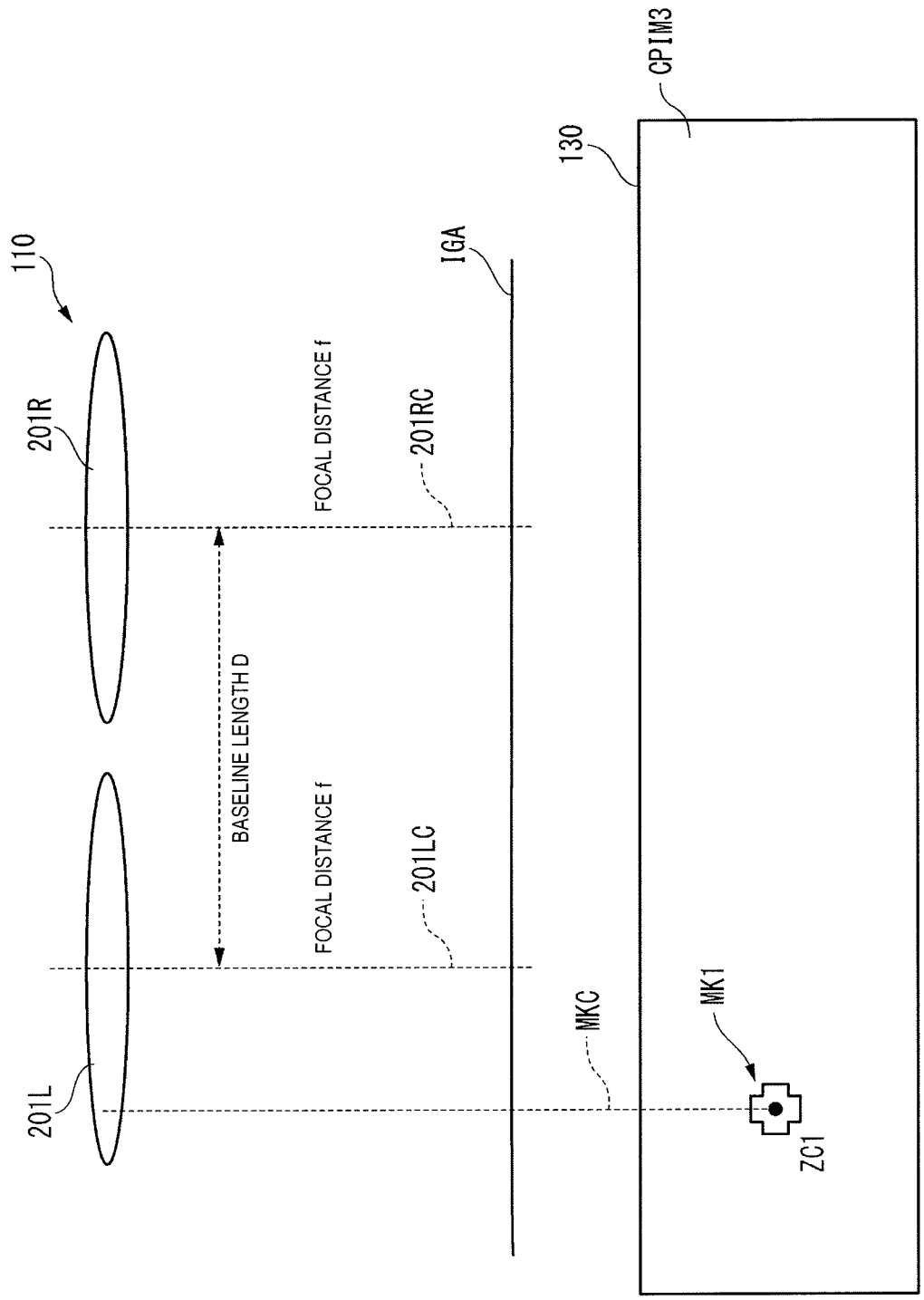
FIG. 22 is illustrating each of an arrangement example of an objective lens for a left eye image and an objective lens for a right eye image and an example of a marker designated on the 3D image displayed on a monitor.
Figure 23:
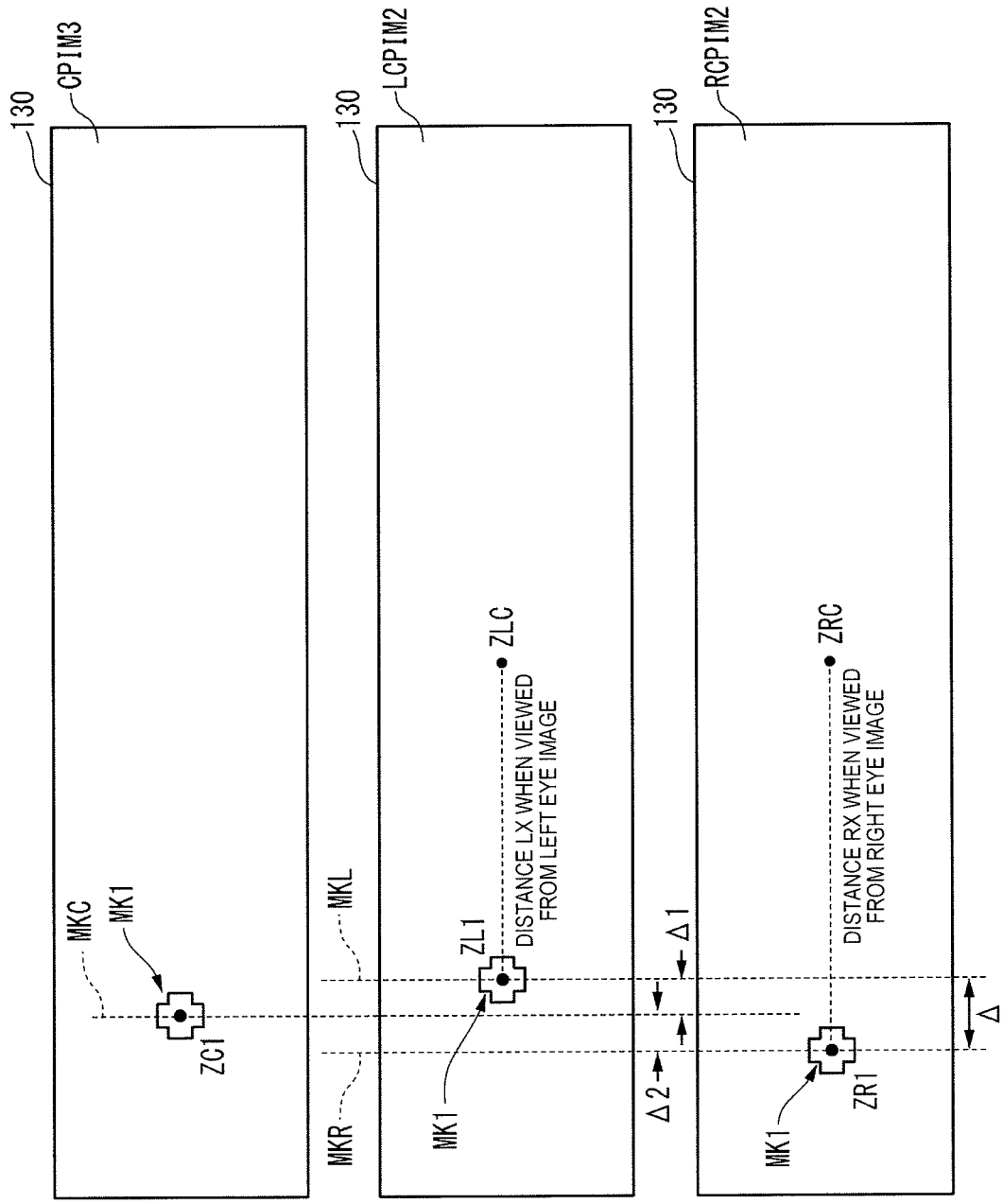
FIG. 23 is an explanatory view of parallax appearing in the left eye image and the right eye image in accordance with the position of a designated marker.

FIG. 22 is an explanatory view illustrating each of an arrangement example of objective lens 201L for the left eye image and objective lens 201R for the right eye image and an example of marker MK1 designated on 3D image CPIM3 displayed on monitor 130. FIG. 23 is an explanatory view of the parallax $\Delta$ appearing in the left eye image and the right eye image in accordance with the position of designated marker MK1.

In FIG. 22, baseline length D between objective lens 201L for forming an image of the subject light on imaging surface IGA of the image sensor (capture 213) of camera head 121 for imaging the left eye image (that is, the 2K left parallax video) and objective lens 201R for forming an image of the subject light on the imaging surface of the image sensor (capture 213) of camera head 121 for imaging the right eye image (that is, the 2K right parallax video) is a default value. The baseline length D corresponds to the distance between axial line 201LC that passes through the lens center of objective lens 201L and axial line 201RC that passes through the lens center of objective lens 201R. In addition, in order to simplify the description of Embodiment 4, focal length f of objective lenses 201L and 201R will be described as the distance from the principal points (not illustrated) of each of objective lenses 201L and 201R to imaging surface IGA.

Here, it is assumed that marker MK1 is displayed at the position designated by the operation of the user (for example, an observer, such as a doctor) on 3D image CPIM3 which configures the 3D video projected to monitor 130. Position ZC1 indicates the center position of marker MK1, and dotted line MKC is a line that passes through the center position of marker MK1 and is provided for describing parallax $\Delta$.

In the uppermost stage of FIG. 23, 3D image CPIM3 is illustrated, the middle stage of FIG. 23 illustrates left eye image LCPIM2 which configures the 2K left parallax video, and the lowermost stage of FIG. 23 illustrates right eye image RCPIM2 which configures the 2K right parallax video. 3D image CPIM3 is stereoscopically displayed as left eye image LCPIM2 and right eye image RCPIM2 which have the parallax $\Delta$ and are obtained by the imaging of the same subject are projected to monitor 130. In addition, dotted lines MKL and MKR are lines that pass through each of the center positions of marker MK1 on left eye image LCPIM2 and marker MK1 on right eye image RCIPM2, and are provided for the description of the parallax $\Delta$.

Here, in a case where marker MK1 is displayed at the position designated by the operation of the user (for example, an observer, such as a doctor), the parallax $\Delta$ between left eye image LCPIM2 and right eye image RCPIM2 corresponds to the sum of distance $\Delta 1$ from position ZC1 indicating the center of marker MK1 on 3D image CPIM3 to position ZL1 indicating the center of marker MK1 on left eye image LCPIM2 and distance $\Delta 2$ from position ZC1 indicating the center of marker MK1 on 3D image CPIM3 and position ZR1 indicating the center of marker MK1 on right eye image RCPIM2. In other words, the equation (1) is established.

Equation 1

$$\Delta = \Delta 1 + \Delta 2 \quad (1)$$

In other words, parallax $\Delta$ corresponds to a difference between distance LX from center position ZLC of left eye image LCPIM2 to the position ZL1 indicating the center of marker MK1 and distance RX from center position ZRC of right eye image RCPIM2 to position ZR1 indicating the center of marker MK1.

Therefore, in the 3D mode, distance measuring circuit 291 derives distance L (refer to FIG. 19) from surgical endoscope 110 to the observation target site based on the parallax Δ (refer to FIG. 23) appearing in the 2K left parallax video from 2K left parallax video extractor 265 and the 2K right parallax video from 2K right parallax video extractor 266, in accordance with the equation (2).

Equation 2

$$L = f \times D / \Delta \qquad (2)$$

Figure 24:
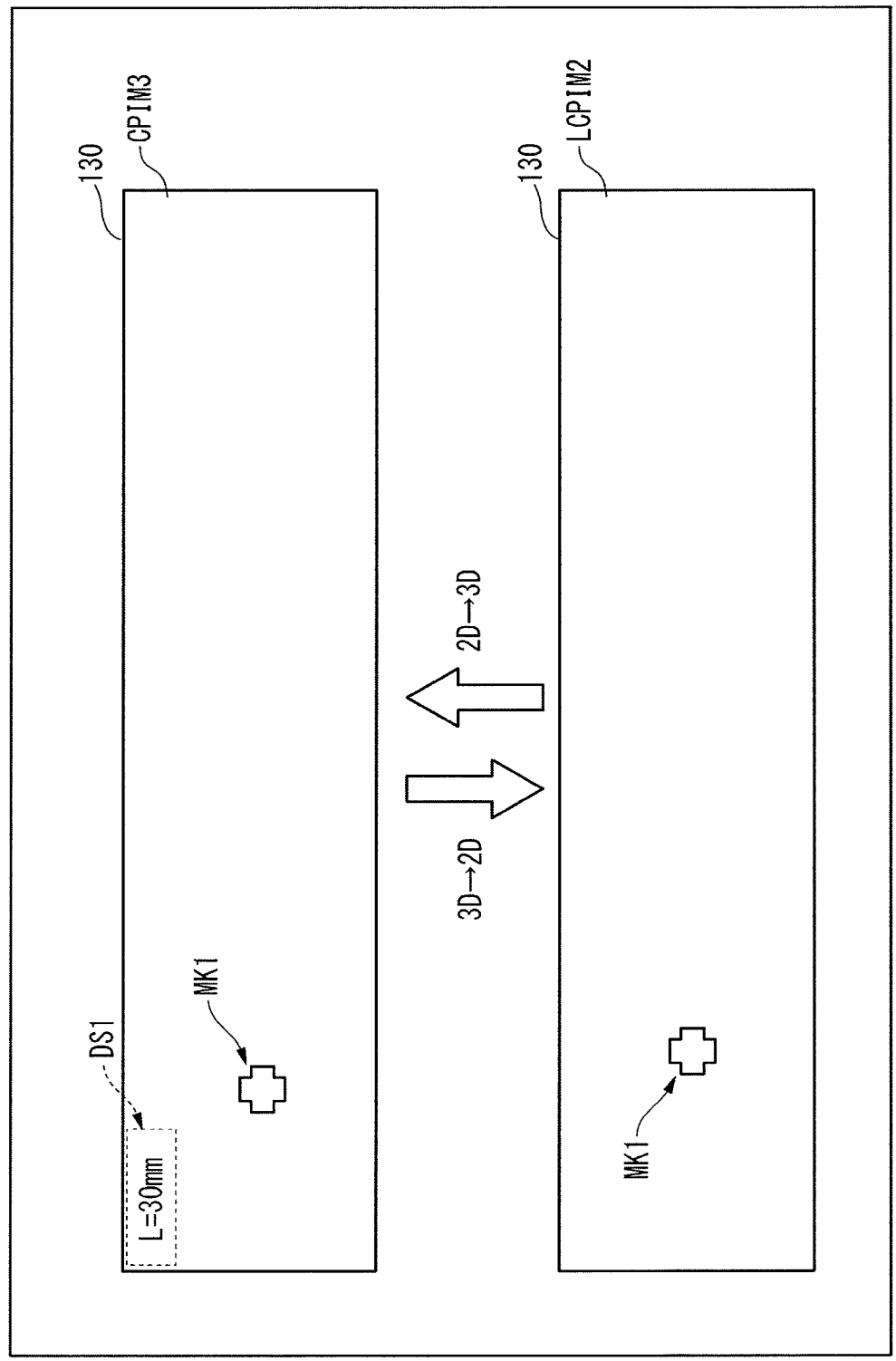
FIG. 24 is an explanatory view illustrating a display example of a distance from a distal end of a surgical endoscope to the subject.

In the 3D mode, when display element generator 292 acquires an instruction to display the measurement result of distance measuring circuit 291 on monitor 130 by CPU 262, display element generator 292 generates the data of a display element (for example, refer to icon DSI of the distance result illustrated in FIG. 24) that corresponds to the measurement result of distance measuring circuit 291, and outputs the generated data to superimposition controllers 293 and 294, respectively.

In the 3D mode, superimposition controller 293 (one example of the output controller) outputs the data of the display element from the display element generator 292 on monitor 130 via channel CH1 after performing superimposition processing with respect to the output video (output image) from video output switcher 273.

In the 3D mode, superimposition controller 294 (one example of the output controller) outputs the data of the display element from display element generator 292 on monitor 130 via channel CH1 after performing superimposition processing with respect to the output video (output image) from video output switcher 274.

FIG. 24 is an explanatory view illustrating a display example of distance L from the distal end of surgical endoscope 110 to subject 40. In the upper stage of FIG. 24, 3D image CPIM3 displayed on monitor 130 is illustrated in the 3D mode, and the 2D image (for example, left eye image LCPIM2) displayed on monitor 130 in the 2D mode is illustrated in the lower stage of FIG. 24.

In the 2D mode, when switching from the 2D mode to the 3D mode by the operation of the user (for example, an observer, such as a doctor), CCU 22 or camera apparatus 20 including CCU 22 measures distance L from surgical endoscope 110 to subject 40 indicated by marker MK1. As a result, icon DS1 indicating the distance measurement result of distance L (for example, L=30 mm) is displayed at a predetermined position on monitor 130 (for example, the upper left end portion of monitor 130).

Meanwhile, in the 3D mode, when switching from the 2D mode to the 3D mode by the operation of the user (for example, an observer, such as a doctor), CCU 22 or camera apparatus 20 including CCU 22 does not display icon DS1 indicating the distance measurement result of distance L (for example L=30 mm). This is because, in the 2D mode, since neither left eye image LCPIM2 nor right eye image is input to distance measuring circuit 291, it is not possible to derive the distance to subject 40.

Above, in the surgical endoscope system of Embodiment 4, in the 3D mode, CCU 22 or camera apparatus 20 including CCU 22 includes distance measuring circuit 291 (one example of distance measurer) which measures distance L (refer to FIG. 19) from surgical endoscope 110 (one example of optical instrument) to the observation target site based on the parallax Δ (refer to FIG. 23) appearing in the left eye image and the right eye image which are imaged by camera head 21. CCU 22 or camera apparatus 20 outputs the result measured by distance measuring circuit 291 (that is, information on the distance) to monitor 130 (refer to FIG. 19) together with the left eye image and the right eye image to which the signal processing is performed. Accordingly, the user (for example, an observer, such as a doctor) can visually grasp the situation of the observation target site projected to monitor 130, can grasp the specific distance information from surgical endoscope 110 (refer to FIG. 19) to the observation target site, and can support the guidance of the next medical practice by the user at the time of surgery or examination.

In addition, in response to the switching from the 3D mode to the 2D mode, CCU 22 or camera apparatus 20 including CCU 22 interrupts the output of the information on the distance to monitor 130. Accordingly, in the 2D mode, neither the left and right 2K left parallax video having parallax nor the 2K right parallax video is input to distance measuring circuit 291, and thus, the information on the distance is not displayed on monitor 130. Therefore, the user (for example, an observer, such as a doctor) can easily recognize that the present is the 2D mode by the fact that the information on the distance is not displayed on monitor 130, and on the other hand, the user can easily recognize that the present is the 3D mode by the fact that the information on the distance is displayed on monitor 130.

Above, while various embodiments have been described with reference to the drawings, it is needless to say that the disclosure is not limited to the examples. Those skilled in the art will appreciate that various modification examples or modification examples can be conceived within the scope described in the claims and understand that the examples naturally fall within the technical scope of the disclosure. Further, within the scope not departing from the gist of the disclosure, each of the configuration elements in the above-described embodiment may be combined in any manner.

In addition, in Embodiment 4, according to the equation (1), regarding distance L from surgical endoscope 110 to the observation target site (that is, subject 40), the distance measurement of the same distance L can be realized when fixing and imaging an angle of view (that is, zooming magnification in the observation optical system in surgical endoscope 110) of surgical endoscope 110. Here, the correspondence relationship between the distance to subject 40 that serves as a reference and the angle of view (that is, zoom magnification) of surgical endoscope 110 that serves as a reference is prepared in advance as a table and stored in image processor 271 or CPU 262 in advance. In a case where the value of the distance derived according to the equation (1) is different from the distance that serves as the reference, image processor 271 corrects derived distance L by using a coefficient that corresponds to a ratio between the current zoom magnification and the reference angle of view (zoom magnification that serves as the reference) defined in the table. When the zoom magnification is changed, focal length f is changed, and according to the equation (1), distance L also changes. For example, in a case where the zoom magnification is 1 and distance L is 2 cm, when the zoom magnification is doubled, focal length f doubles and distance L also doubles to 4 cm. However, since distance L measured in Embodiment 4 is the distance from the distal end of the insertion portion of surgical endoscope 110 to subject 40, practically, distance L becomes wrong when the distance reaches 4 cm. Therefore, in a case where the zoom magnification is changed, it is necessary to correct distance L obtained by the equation (1) by using the coefficient that corresponds to the change ratio of the zoom magnification described above.

In addition, in each of the above-described embodiments, a case where the 2K left parallax video and the 2K right parallax video which configure the 3D video are extracted and output from the 2D image having 4K resolution has been described, but it is needless to say that CCU 22 may extract and output, for example, the 4K left parallax video and the 4K right parallax video which configure the 3D video from the 2D video having the pixel number that corresponds to 8K resolution.

The disclosure is advantageous as an image processing apparatus, a camera apparatus, and an image processing method which are capable of electronically extracting a part with excellent image quality from each of the left eye image and the right eye image which configure the 3D video by a simple user operation, and imaging and outputting a high-definition 3D video with one camera.

What is claimed is:

1. An image processing apparatus which is connected to a camera head, the camera head being capable of imaging a left eye image and a right eye image the left eye image and the right eye image having parallax on one screen based on light at a target site incident on an optical instrument, the image processing apparatus comprising:
    a processor that performs the signal processing of the left eye image and the right eye image which are imaged by the camera head; and
    an output that outputs the left eye image and the right eye image on which the signal processing is performed to a monitor, the left eye image and the right eye image being misaligned when projecting a three-dimensional image on the monitor,
    wherein the processor adjusts an extraction position of at least one of the left eye image and the right eye image in accordance with a user operation based on the left eye image and the right eye image which are displayed on the monitor, to correct a projection of the three-dimensional image on the monitor,
    the processor saves an adjustment result of the extraction position of the at least one of the left eye image and the right eye image in a memory, and
    the processor is configured to adjust an extraction position of both of the left eye image and the right eye image which are imaged by the camera head in at least one of a horizontal direction or a vertical direction in accordance with the user operation.

2. The image processing apparatus of claim 1, wherein the processor adjusts the extraction position in the horizontal direction of at least one of the left eye image and the right eye image which are imaged by the camera head in accordance with the user operation.

3. The image processing apparatus of claim 1, wherein the processor adjusts the extraction position in the vertical direction of at least one of the left eye image and the right eye image which are imaged by the camera head in accordance with the user operation.

4. The image processing apparatus of claim 1, wherein the processor adjusts the extraction position both in the horizontal direction or in the vertical direction of the left eye image and the right eye image which are imaged by the camera head in accordance with the user operation.

5. The image processing apparatus of claim 1, wherein the processor determines a distance from the optical instrument to the target site based on the parallax appearing in the left eye image and the right eye image which are imaged by the camera head in a 3D mode, and
    the output outputs information on the distance to the monitor together with the left eye image and the right eye image on which the signal processing is performed.

6. The image processing apparatus of claim 5, wherein the output interrupts the output of the information on the distance to the monitor in response to switching from the 3D mode to a 2D mode.

7. A camera apparatus comprising:
    a camera head that is capable of imaging a left eye image and a right eye image, the left eye image and the right eye image having parallax on one screen based on light at a target site incident on an optical instrument;
    a processor that performs the signal processing of the left eye image and the right eye image which are imaged by the camera head; and
    an output that outputs the left eye image and the right eye image on which the signal processing is performed to a monitor, the left eye image and the right eye image being misaligned when projecting a three-dimensional image on the monitor,
    wherein the processor adjusts an extraction position of at least one of the left eye image and the right eye image in accordance with a user operation based on the left eye image and the right eye image which are displayed on the monitor, to correct a projection of the three-dimensional image on the monitor,
    the processor saves an adjustment result of the extraction position of the at least one of the left eye image and the right eye image in a memory, and
    the processor is configured to adjust the extraction position of both of the left eye image and the right eye image which are imaged by the camera head in at least one of a horizontal direction or a vertical direction in accordance with the user operation.

8. An image processing method in which an image processing apparatus is connected to a camera head, the camera head being capable of imaging a left eye image and a right eye image, the left eye image and the right eye image having parallax on one screen based on light at a target site incident on an optical instrument is used, the image processing method comprising:
    performing, by a processor, signal processing of the left eye image and the right eye image which are imaged by the camera head;
    outputting the left eye image and the right eye image on which the signal processing is performed to a monitor, the left eye image and the right eye image being misaligned when projecting a three-dimensional image on the monitor; and
    adjusting, by the processor, an extraction position of at least one of the left eye image and the right eye image in accordance with a user operation based on the left eye image and the right eye image which are displayed on the monitor, to correct a projection of the three-dimensional image on the monitor,
    wherein the processor saves an adjustment result of the extraction position of the at least one of the left eye image and the right eye image in a memory, and
    the processor is configured to adjust the extraction position of both of the left eye image and the right eye image which are imaged by the camera head in at least one of a horizontal direction or a vertical direction in accordance with the user operation.

* * * * *